(12) United States Patent
Jepson et al.

(10) Patent No.: US 8,394,080 B2
(45) Date of Patent: Mar. 12, 2013

(54) NEEDLELESS CONNECTOR WITH SLIDER

(75) Inventors: Steven C. Jepson, Vernon Hills, IL (US); Alice M. Jandrisits, Des Plaines, IL (US); Kent L. Lurvey, Grayslake, IL (US)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 461 days.

(21) Appl. No.: 12/775,148

(22) Filed: May 6, 2010

(65) Prior Publication Data

US 2010/0292674 A1  Nov. 18, 2010

Related U.S. Application Data

(60) Provisional application No. 61/178,229, filed on May 14, 2009.

(51) Int. Cl.
  *A61M 25/16* (2006.01)
(52) U.S. Cl. ....................................................... 604/537
(58) Field of Classification Search .................. 604/537
  See application file for complete search history.

(56) References Cited

U.S. PATENT DOCUMENTS

| | | | |
|---|---|---|---|
| 3,368,560 A | 2/1968 | Gewecke | |
| 3,509,879 A | 5/1970 | Bathish et al. | |
| 3,915,212 A | 10/1975 | Bujan et al. | |
| 3,977,555 A | 8/1976 | Larson | |
| 4,181,140 A | 1/1980 | Bayham et al. | |
| 4,187,893 A | 2/1980 | Bujan | |
| 4,270,534 A | 6/1981 | Adams | |
| 4,294,247 A | 10/1981 | Carter et al. | |
| 4,340,049 A | 7/1982 | Munsch | |
| 4,386,622 A | 6/1983 | Munsch | |
| 4,410,321 A | 10/1983 | Pearson et al. | |
| 4,411,662 A | 10/1983 | Pearson | |
| 4,432,755 A | 2/1984 | Pearson | |
| 4,435,179 A | 3/1984 | Walker | |
| 4,458,733 A | 7/1984 | Lyons | |
| 4,479,989 A | 10/1984 | Mahal | |
| 4,484,351 A | 11/1984 | de Leeuwe et al. | |
| 4,507,114 A | 3/1985 | Bohman et al. | |
| 4,583,971 A | 4/1986 | Bocquet et al. | |

(Continued)

FOREIGN PATENT DOCUMENTS

| | | |
|---|---|---|
| CA | 2386830 | 9/2009 |
| DE | 29800107 | 3/1998 |

(Continued)

OTHER PUBLICATIONS

Baxter Healthcare Corporation, Clearlink Brochure (Aug. 2007) (2 pages).

(Continued)

*Primary Examiner* — Nicholas Lucchesi
*Assistant Examiner* — Diva K Chander
(74) *Attorney, Agent, or Firm* — Marshall, Gerstein & Borun LLP

(57) ABSTRACT

A needleless connector includes a housing having a housing passage with an open end, a slider disposed in the housing passage, and a mechanism to bias the slider toward the open end of the housing passage. The connector may also include a seal at the open end of the housing passage, the seal either cooperating with the slider to seal the open end of the connector, or sealing the open end of the connector without interaction with the slider, for example taking the form of a slit septum.

13 Claims, 29 Drawing Sheets

U.S. PATENT DOCUMENTS

| | | | |
|---|---|---|---|
| 4,586,928 | A | 5/1986 | Barnes et al. |
| 4,589,879 | A | 5/1986 | Pearson |
| 4,637,934 | A | 1/1987 | White |
| 4,722,727 | A | 2/1988 | Ogden et al. |
| 4,785,859 | A | 11/1988 | Gustavsson et al. |
| 4,846,795 | A | 7/1989 | Minagawa et al. |
| 5,006,114 | A | 4/1991 | Rogers et al. |
| 5,065,783 | A | 11/1991 | Ogle, II |
| 5,122,123 | A | 6/1992 | Vaillancourt |
| 5,269,771 | A * | 12/1993 | Thomas et al. ............... 604/539 |
| 5,304,163 | A | 4/1994 | Bonnici et al. |
| 5,308,347 | A | 5/1994 | Sunago et al. |
| 5,330,464 | A | 7/1994 | Mathias et al. |
| 5,334,180 | A | 8/1994 | Adolf et al. |
| 5,380,315 | A | 1/1995 | Isono et al. |
| 5,391,150 | A | 2/1995 | Richmond |
| 5,514,123 | A | 5/1996 | Adolf et al. |
| 5,533,994 | A | 7/1996 | Meyer et al. |
| 5,540,674 | A | 7/1996 | Karas et al. |
| 5,685,866 | A | 11/1997 | Lopez |
| 5,700,248 | A | 12/1997 | Lopez |
| 5,730,418 | A | 3/1998 | Feith et al. |
| 5,738,663 | A | 4/1998 | Lopez |
| 5,782,816 | A | 7/1998 | Werschmidt et al. |
| 5,785,693 | A * | 7/1998 | Haining ............... 604/249 |
| 5,810,398 | A | 9/1998 | Matkovich |
| 5,873,862 | A | 2/1999 | Lopez |
| 5,901,942 | A | 5/1999 | Lopez |
| 5,902,298 | A | 5/1999 | Niedospial, Jr. et al. |
| 5,928,204 | A | 7/1999 | Lopez |
| 6,019,748 | A | 2/2000 | Lopez |
| 6,029,946 | A | 2/2000 | Doyle |
| 6,032,926 | A | 3/2000 | Fuchs |
| 6,050,978 | A | 4/2000 | Orr et al. |
| 6,063,062 | A * | 5/2000 | Paradis ............... 604/249 |
| 6,113,068 | A | 9/2000 | Ryan |
| 6,113,583 | A | 9/2000 | Fowles et al. |
| 6,126,618 | A | 10/2000 | Bischof |
| 6,132,403 | A | 10/2000 | Lopez |
| 6,132,404 | A | 10/2000 | Lopez |
| 6,132,413 | A | 10/2000 | Mathias et al. |
| 6,152,900 | A * | 11/2000 | Mayer ............... 604/167.02 |
| 6,156,025 | A * | 12/2000 | Niedospial et al. ............ 604/408 |
| 6,179,821 | B1 | 1/2001 | Caspary et al. |
| 6,245,048 | B1 | 6/2001 | Fangrow, Jr. et al. |
| 6,261,282 | B1 * | 7/2001 | Jepson et al. ............... 604/533 |
| 6,280,431 | B1 | 8/2001 | Domkowski et al. |
| 6,290,206 | B1 | 9/2001 | Doyle |
| 6,299,131 | B1 | 10/2001 | Ryan |
| 6,325,782 | B1 | 12/2001 | Lopez |
| 6,344,033 | B1 * | 2/2002 | Jepson et al. ............... 604/256 |
| 6,394,992 | B1 | 5/2002 | Sjoholm et al. |
| 6,428,520 | B1 | 8/2002 | Lopez et al. |
| 6,447,498 | B1 * | 9/2002 | Jepson et al. ............... 604/411 |
| 6,485,479 | B1 | 11/2002 | Knierbein et al. |
| 6,491,679 | B1 | 12/2002 | Okamoto et al. |
| 6,541,802 | B2 | 4/2003 | Doyle |
| 6,572,592 | B1 | 6/2003 | Lopez |
| 6,585,229 | B2 | 7/2003 | Cote, Sr. et al. |
| 6,599,273 | B1 | 7/2003 | Lopez |
| 6,635,044 | B2 | 10/2003 | Lopez |
| 6,651,956 | B2 | 11/2003 | Miller |
| 6,655,655 | B1 | 12/2003 | Matkovich et al. |
| 6,681,946 | B1 | 1/2004 | Jansen et al. |
| 6,745,998 | B2 | 6/2004 | Doyle |
| 6,758,833 | B2 | 7/2004 | Lopez |
| 6,840,501 | B2 | 1/2005 | Doyle |
| 6,869,426 | B2 | 3/2005 | Ganem |
| 6,875,203 | B1 | 4/2005 | Fowles et al. |
| 6,932,795 | B2 | 8/2005 | Lopez et al. |
| 6,945,417 | B2 | 9/2005 | Jansen et al. |
| 6,955,669 | B2 | 10/2005 | Curutcharry et al. |
| 7,004,934 | B2 | 2/2006 | Vaillancourt |
| 7,025,389 | B2 | 4/2006 | Cuschieri et al. |
| 7,037,302 | B2 | 5/2006 | Vaillancourt et al. |
| 7,074,216 | B2 | 7/2006 | Fowles et al. |
| 7,100,890 | B2 * | 9/2006 | Cote et al. ............... 251/149.1 |
| 7,118,560 | B2 * | 10/2006 | Bonaldo ............... 604/537 |
| 7,350,669 | B2 | 4/2008 | Rani |
| 7,350,764 | B2 | 4/2008 | Raybuck |
| 7,396,051 | B2 | 7/2008 | Baldwin et al. |
| 7,396,348 | B2 | 7/2008 | Newton et al. |
| 7,425,209 | B2 | 9/2008 | Fowles et al. |
| 7,503,908 | B2 * | 3/2009 | Bartholomew ............... 604/249 |
| 7,753,892 | B2 * | 7/2010 | Newton et al. ............... 604/236 |
| 7,789,864 | B2 * | 9/2010 | Cote et al. ............... 604/256 |
| 7,981,090 | B2 * | 7/2011 | Plishka et al. ............... 604/249 |
| 8,062,280 | B2 * | 11/2011 | Jepson et al. ............... 604/415 |
| 8,172,823 | B2 * | 5/2012 | Rondeau et al. ............... 604/407 |
| 8,177,760 | B2 * | 5/2012 | Rome et al. ............... 604/247 |
| 8,221,391 | B2 * | 7/2012 | Fangrow, Jr. ............... 604/539 |
| 2001/0047154 | A1 * | 11/2001 | Jepson et al. ............ 604/167.01 |
| 2002/0024036 | A1 | 2/2002 | Rohrbough et al. |
| 2003/0093061 | A1 * | 5/2003 | Ganem ............... 604/533 |
| 2004/0073174 | A1 | 4/2004 | Lopez |
| 2004/0122414 | A9 | 6/2004 | Hurst et al. |
| 2004/0186458 | A1 | 9/2004 | Hiejima et al. |
| 2004/0199139 | A1 | 10/2004 | Fowles et al. |
| 2004/0206924 | A1 | 10/2004 | Newton et al. |
| 2004/0243070 | A1 | 12/2004 | Lopez |
| 2005/0090805 | A1 | 4/2005 | Shaw et al. |
| 2005/0137566 | A1 | 6/2005 | Fowles et al. |
| 2005/0222541 | A1 | 10/2005 | Lopez et al. |
| 2006/0200087 | A1 | 9/2006 | Lopez |
| 2006/0200091 | A1 | 9/2006 | Lopez |
| 2006/0200092 | A1 | 9/2006 | Lopez |
| 2006/0200093 | A1 | 9/2006 | Lopez |
| 2006/0206058 | A1 | 9/2006 | Lopez |
| 2006/0206059 | A1 | 9/2006 | Lopez |
| 2006/0206060 | A1 | 9/2006 | Lopez |
| 2006/0206061 | A1 | 9/2006 | Lopez et al. |
| 2006/0229572 | A1 | 10/2006 | Lopez |
| 2006/0264845 | A1 | 11/2006 | Lopez |
| 2006/0264846 | A1 | 11/2006 | Lopez |
| 2006/0264847 | A1 | 11/2006 | Lopez |
| 2006/0264849 | A1 | 11/2006 | Lopez et al. |
| 2006/0287638 | A1 | 12/2006 | Aneas |
| 2007/0007478 | A1 | 1/2007 | Leinsing et al. |
| 2007/0012893 | A1 | 1/2007 | Lee et al. |
| 2007/0021721 | A1 | 1/2007 | Lopez |
| 2007/0038189 | A1 | 2/2007 | Bartholomew |
| 2007/0066965 | A1 | 3/2007 | Coambs et al. |
| 2007/0173783 | A1 | 7/2007 | Haindl |
| 2007/0299419 | A1 | 12/2007 | Vancaillie et al. |
| 2008/0140021 | A1 | 6/2008 | Richmond |
| 2008/0172003 | A1 * | 7/2008 | Plishka et al. ............... 604/249 |
| 2008/0172005 | A1 * | 7/2008 | Jepson ............... 604/249 |
| 2008/0172024 | A1 | 7/2008 | Yow |
| 2008/0190485 | A1 | 8/2008 | Guala |
| 2008/0228163 | A1 | 9/2008 | Smith |
| 2009/0270832 | A1 | 10/2009 | Vancaillie et al. |
| 2010/0049160 | A1 | 2/2010 | Jepson et al. |
| 2010/0108681 | A1 | 5/2010 | Jepson et al. |

FOREIGN PATENT DOCUMENTS

| | | |
|---|---|---|
| EP | 0811797 | 12/1997 |
| WO | WO 97/43573 | 11/1997 |
| WO | WO 01/32524 | 5/2001 |
| WO | WO 2006/062912 | 6/2006 |

OTHER PUBLICATIONS

Edwards Lifesciences LLC, VAMP and VAMP Jr. System Brochure (2002) (4 pages).

ICU Medical, Inc., CLC2000® Brochure (circa Jun. 2007) (2 pages).

I-Flow Corporation, One Step KVO™ Brochure (Jan. 1999) (2 pages).

Maximus Medical, MaxPlus Brochure (circa Apr. 2007) (2 pages).

* cited by examiner

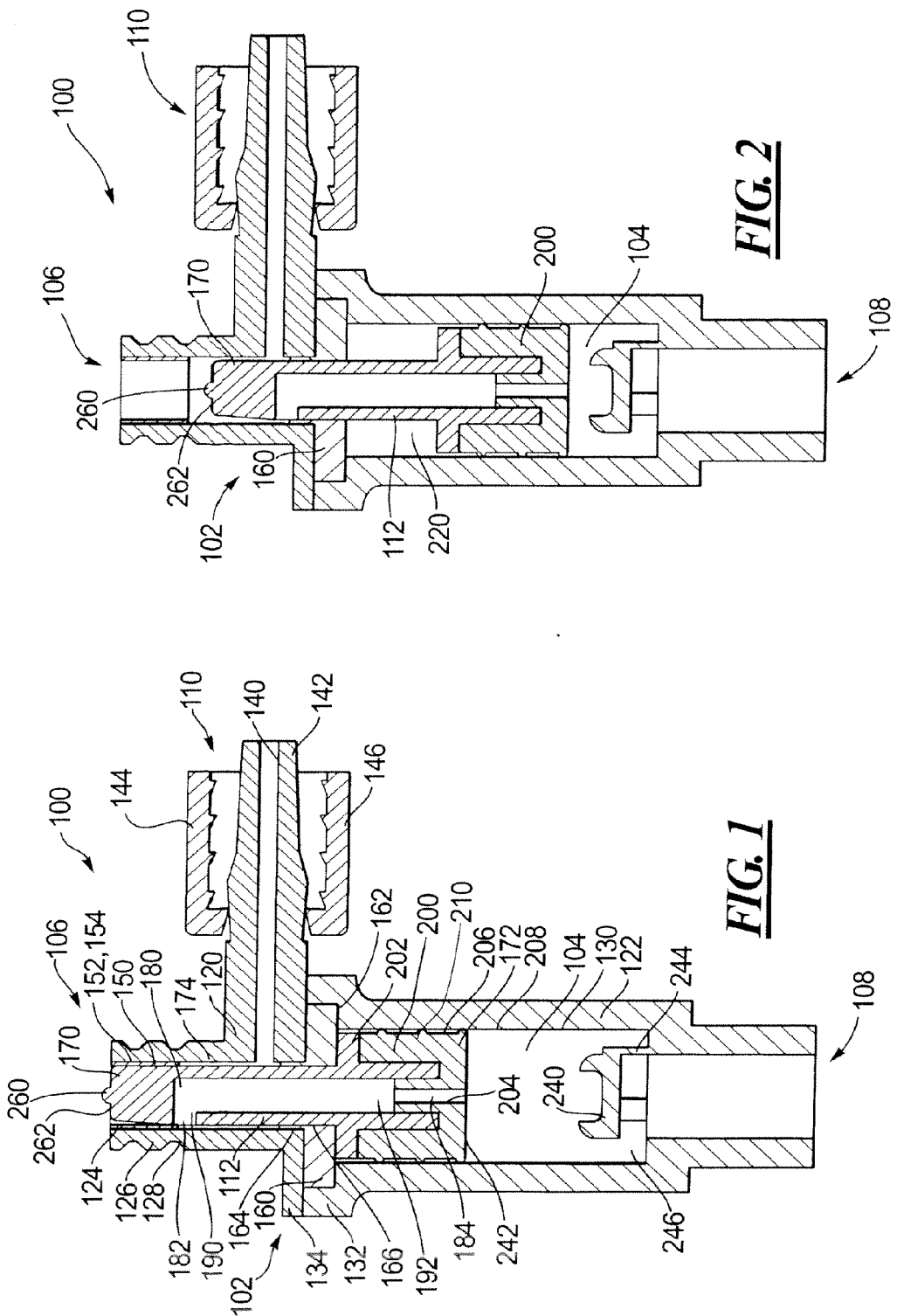

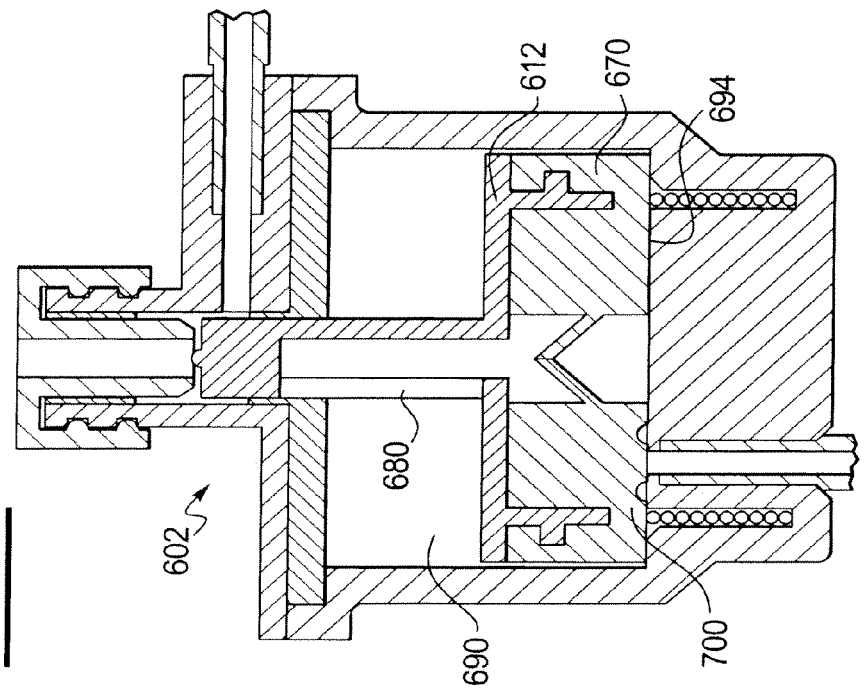
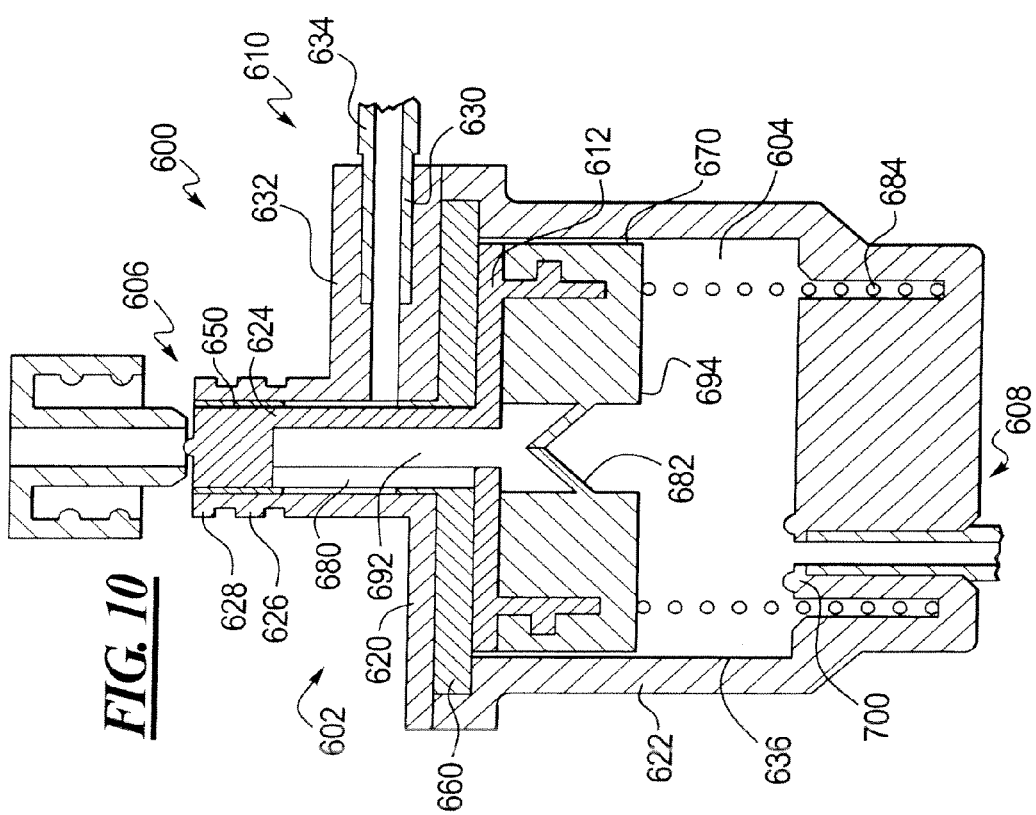

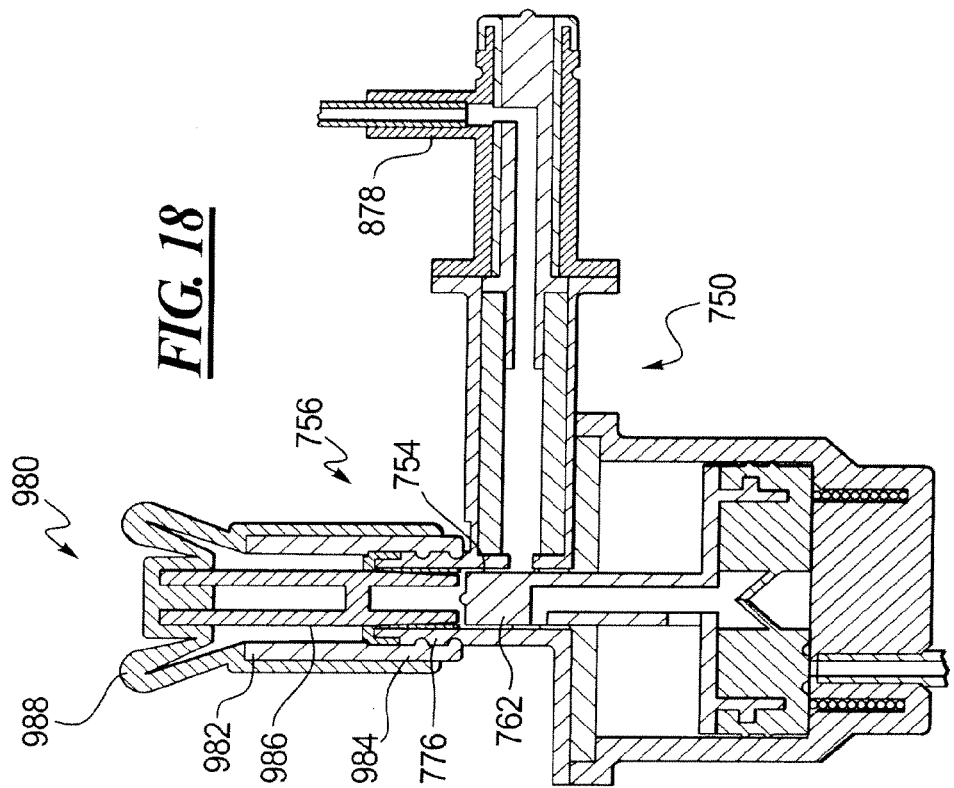
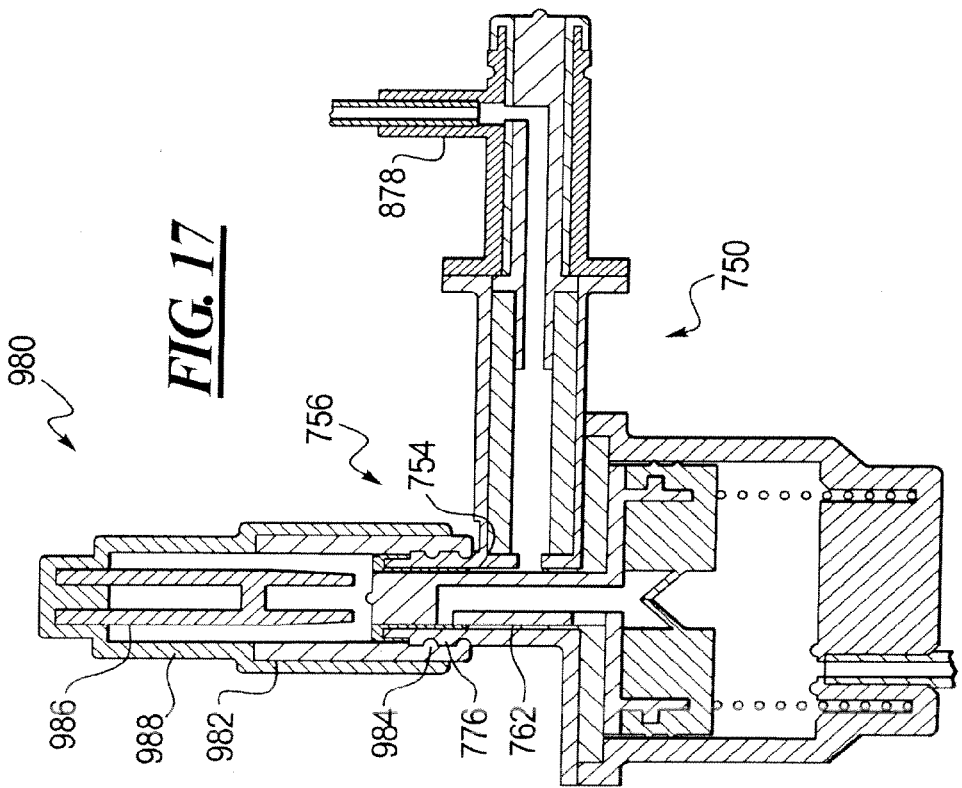

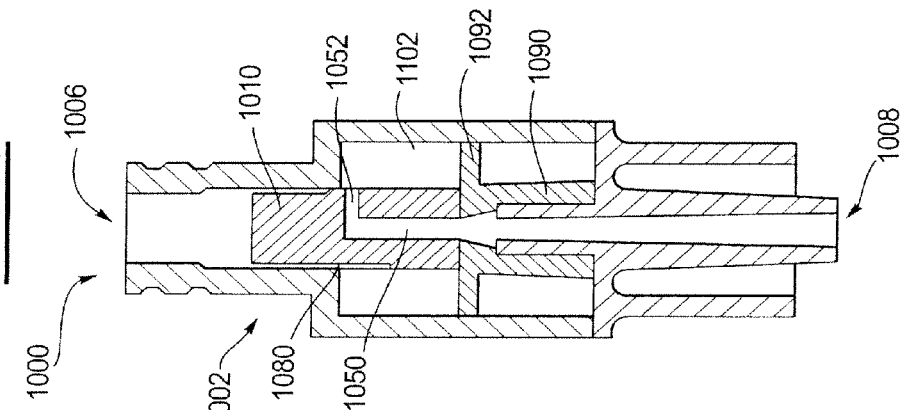
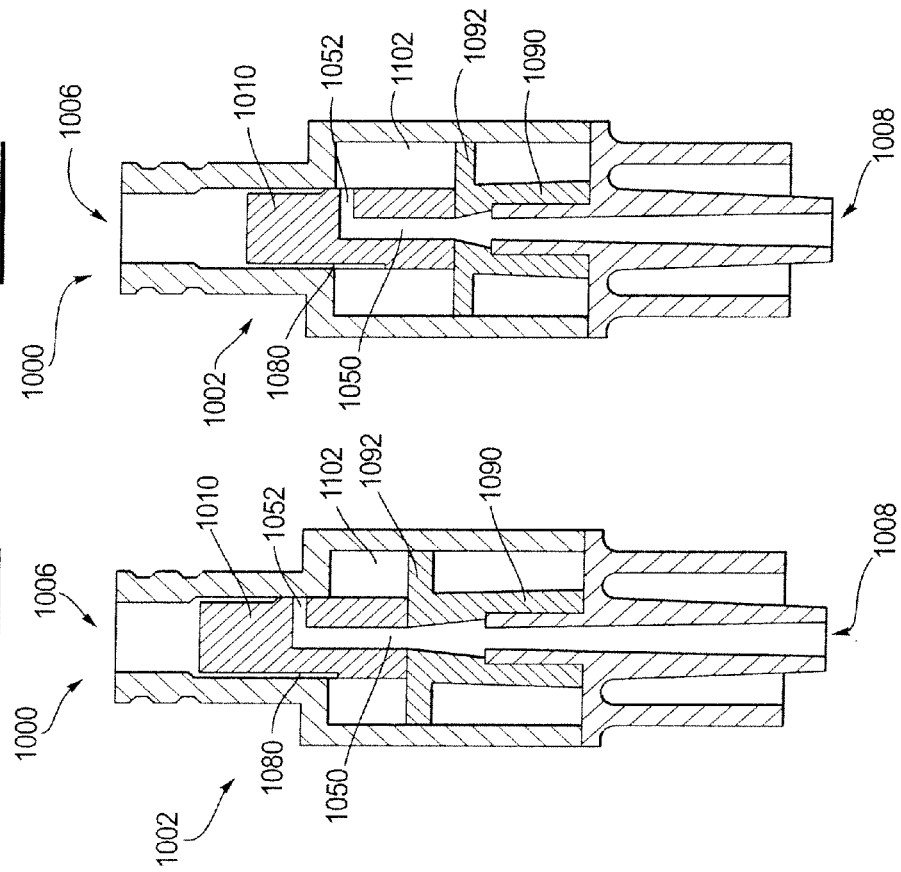
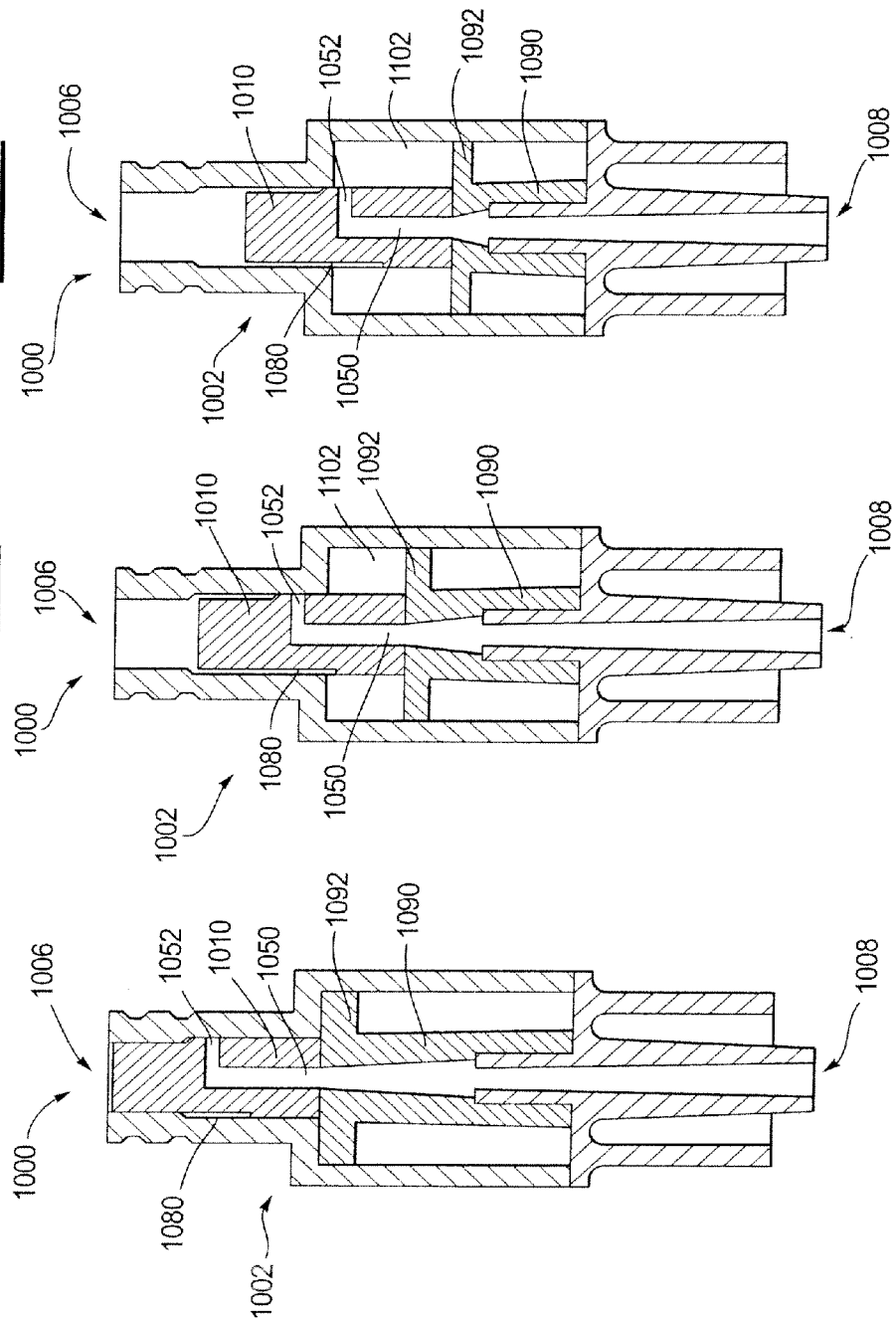

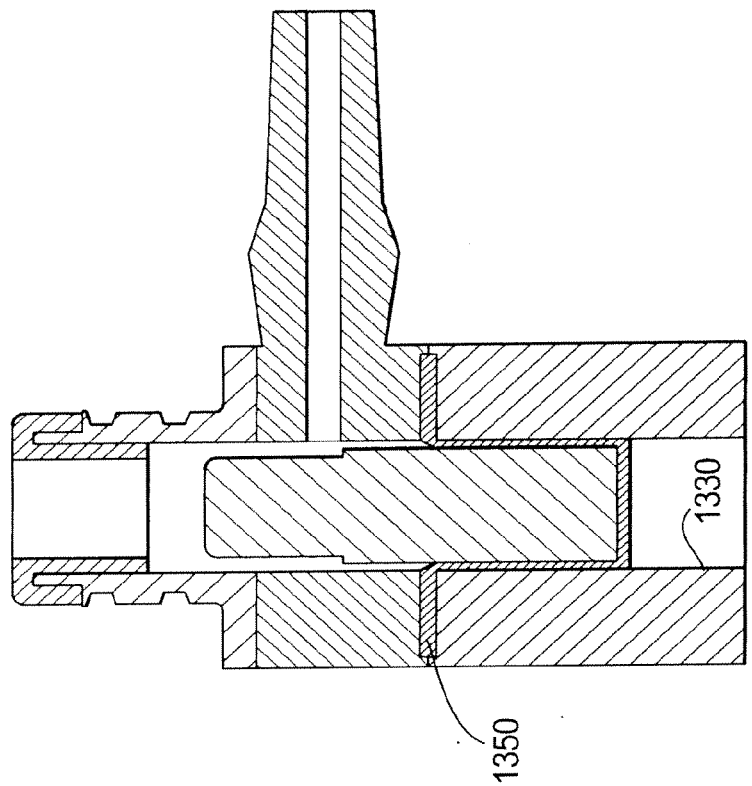
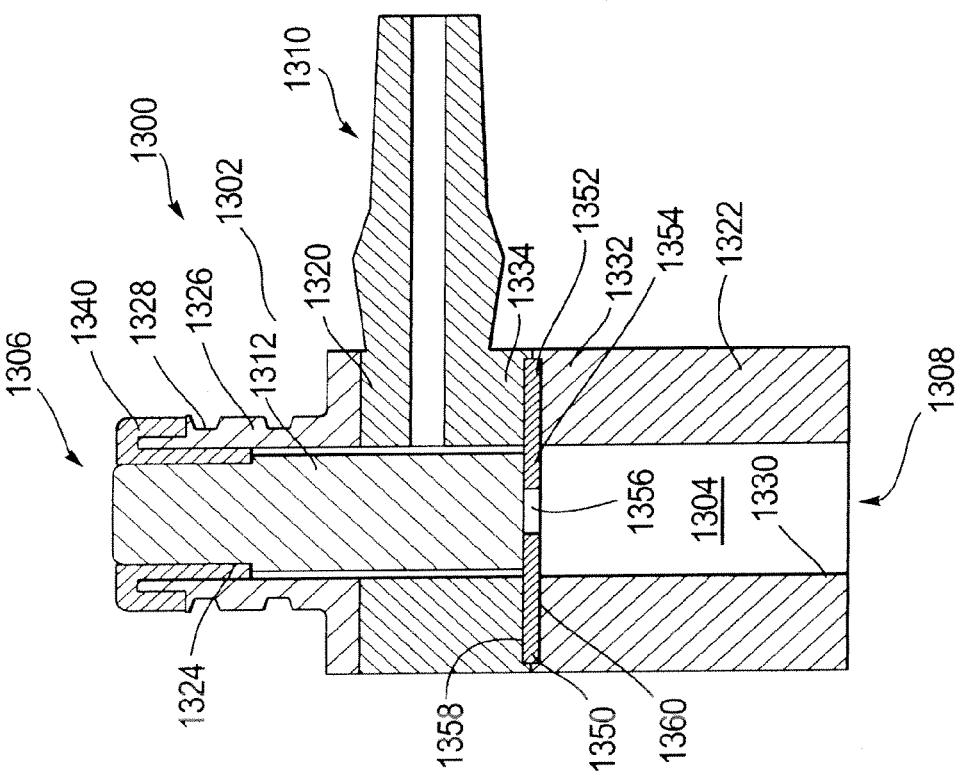

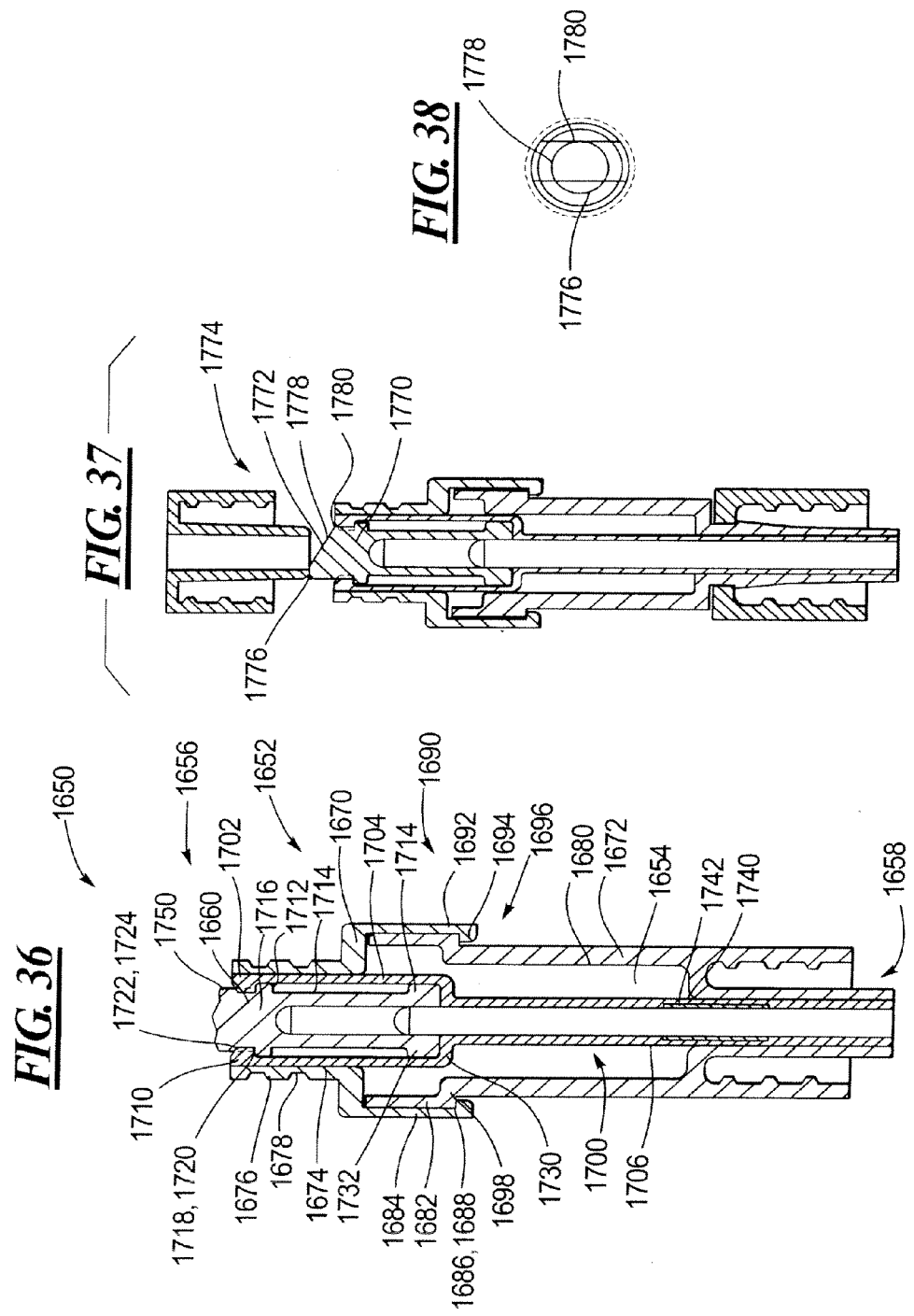

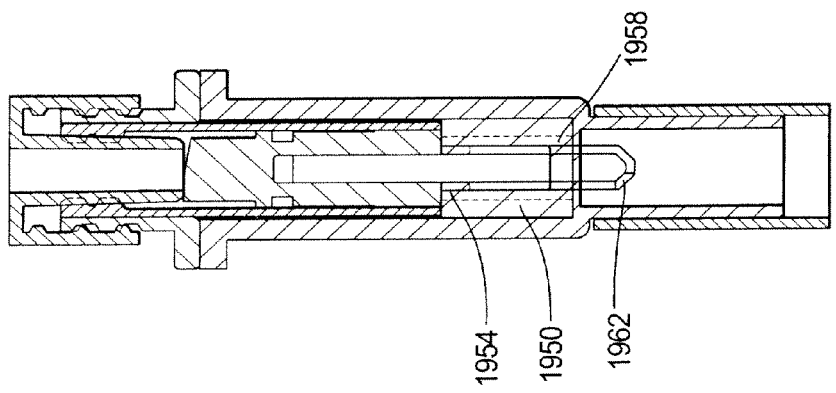
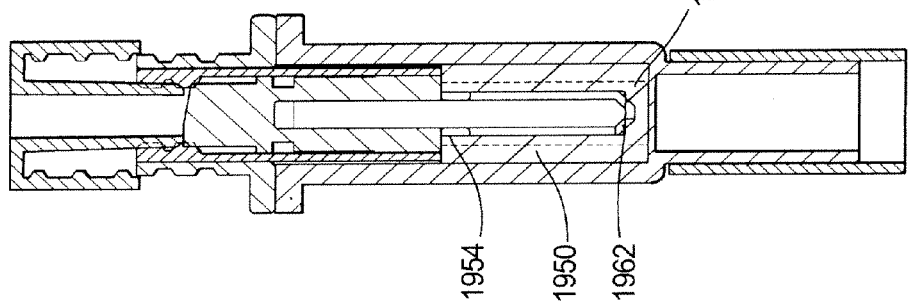
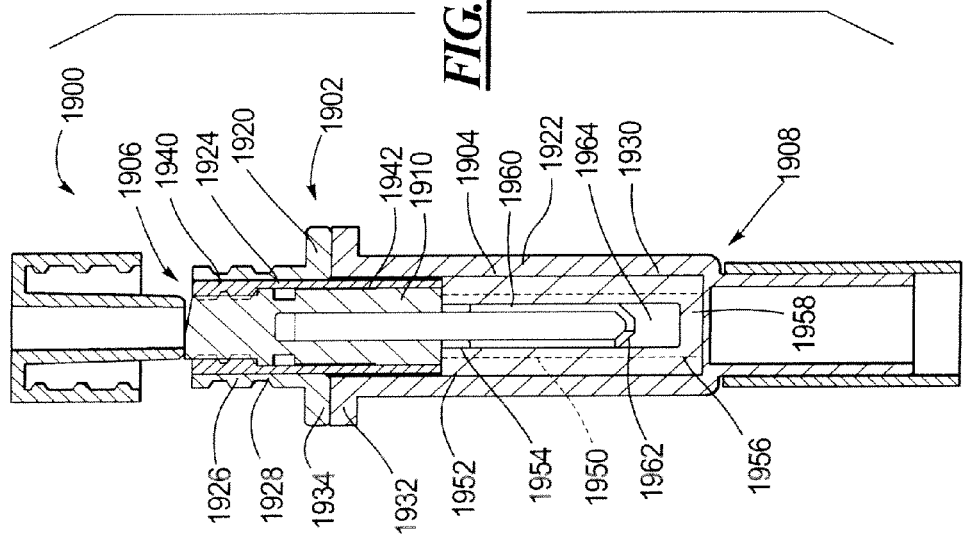

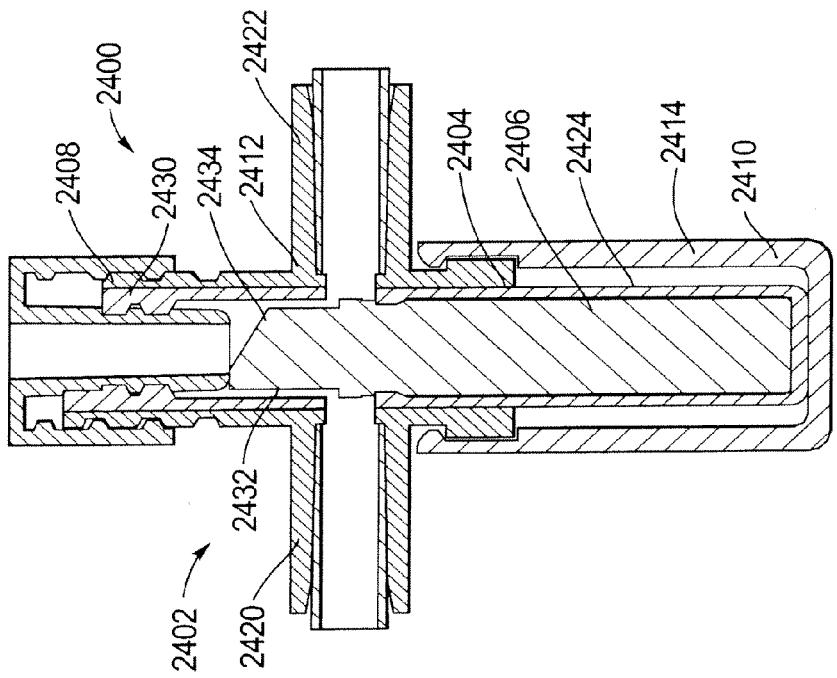
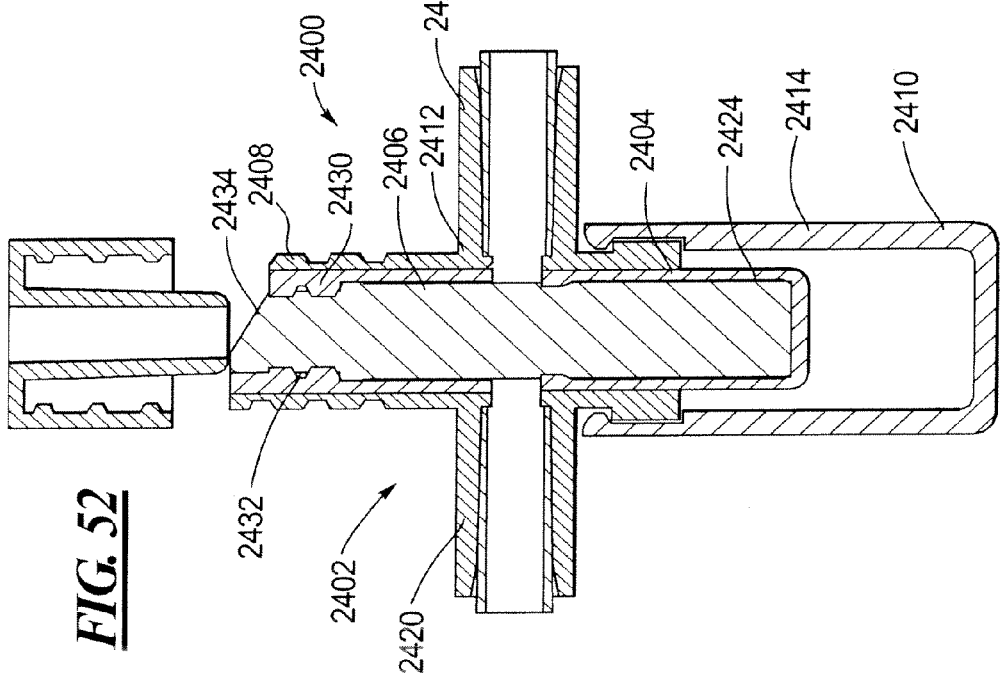

NEEDLELESS CONNECTOR WITH SLIDER

This patent claims the benefit of U.S. Application No. 61/178,229, filed May 14, 2009, which is hereby incorporated by reference in its entirety in the present application.

BACKGROUND

This patent is directed to a needleless connector, and, in particular, to a needleless connector with a slider moveable within the housing.

Needleless connectors have come into widespread use in intravenous (I.V.) administration sets. These needleless connectors replace more traditional technologies, where a needle is used to puncture an elastomeric diaphragm or septum. The use of needles and other pointed instruments presents hazards to the equipment, the patients and the healthcare personnel. For example, accidental needle sticks may permit infectious diseases to be transferred from the patient to the healthcare worker.

One particular form of the needleless connector is the T-site connector, which connector may also be used as a stopcock. The T-site connector has three legs: the patient (or catheter) leg, the flush reservoir leg, and the medication (or med)/sample port leg. Because a Luer lock or similar device is typically used with the med/sample port leg, this leg may also be referred to as the Luer-activated device (or LAD) leg.

Conventionally, when the med/sample port is accessed using a Luer to administer medication to the patient or to withdraw a blood (or other body fluid) sample, the med/sample port must be manually flushed using a syringe. This manual flushing occurs both before and after access to ensure that all unwanted material is removed from the connector. The manual flushing usually involves a multi-step process, passing several different fluids through the med/sample port. For example, according to one conventional administration therapy, the flush is performed with a sequence of saline, administer, saline and heparin, or S-A-S-H. An abbreviated form of the therapy is also known, using the sequence of saline, administer, and saline, or SAS. In the case of blood sampling, if the "clearing sample" or "discard sample" is re-infused (to minimize risk of "nosocomial anemia"), additional steps (manual connections by syringe) are required.

It will be recognized that this multi-step process has its challenges. For example, the process adds to the time demands (for obtaining or filling the flush syringes, swabbing the med/sample port, attaching the syringes, etc.) placed on the healthcare professional during his or her daily routine. Further, the SASH or SAS therapies are material-intensive as well, requiring the use of multiple flush syringes and fluids (saline, antibiotic and heparin). Moreover, any time the med/sample port is accessed, there is a risk of infection, however competent the healthcare professional or thorough the procedure followed. If the healthcare professional is distracted, the risks increase due to human error.

It will also be recognized that a need may exist to clear material from in-line needleless connectors as well. For example, certain in-line needleless connectors have net negative displacement, wherein fluid from the patient will be drawn into the connector (reflux) after the Luer or other instrument has been removed from the connector (disconnect), where the material then remains. Other needleless connectors have been designed to have net positive displacement; the connector actually discharges fluid into the patient after the Luer has been disconnected. However, the net positive displacement is typically associated with a reflux of material into the connector upon attachment of the Luer to the connector. Where the infusion of fluids through the connector is a low flow rates, some of the material may be maintained in the connector, even if a positive displacement later occurs upon removal of the Luer.

As set forth in more detail below, the present disclosure sets forth an improved assembly embodying advantageous alternatives to the conventional devices and methods discussed above.

SUMMARY

According to an aspect of the present disclosure, a needleless connector includes a housing having a housing passage with first and second open ends and a side port, a first stationary seal disposed between the first end of the housing passage and the side port, and a second stationary seal disposed between the side port and the second end of the housing passage. The connector also includes a slider that is disposed in the passage and that has a first and second opposing ends and a side between the first and second ends. The slider also has a slider passage with first and second open ends, the first end of the slider passage disposed along the side of the slider and the second end of the slider passage disposed at the second end of the slider. The slider has a first state wherein the first end of the slider abuts the first stationary seal and the first end of the slider passage is unsealed, a second state wherein the first end of the slider is spaced from the first stationary seal and the first end of the slider passage is unsealed, and a third state wherein the first end of the slider is spaced from the first stationary seal and the first end of the slider passage abuts the second stationary seal.

According to another aspect of the present disclosure, a needleless connector includes a housing having a housing passage with first and second open ends and a side port, a first stationary seal disposed between the first end of the housing passage and the side port, and a second stationary seal disposed between the side port and the second end of the housing passage. A slider is disposed in the passage and has first and second opposing ends and a side between the first and second ends. The slider also has a slider passage with a first and second open ends, the first end of the slider passage disposed along the side of the slider and the second end of the slider passage disposed at the second end of the slider. The slider has a first state wherein the first end of the slider abuts the first stationary seal and the first end of the slider passage is sealed, a second state wherein the first end of the slider is spaced from the first stationary seal and the first end of the slider passage is unsealed, and a third state wherein the first end of the slider is spaced from the first stationary seal and the first end of the slider passage abuts by the second stationary seal.

According to a further aspect of the present disclosure, a needleless connector includes a housing having a housing passage with first and second open ends. A slider is disposed in the passage and has first and second opposing ends and a side between the first and second ends. The slider has a slider passage with a first and second open ends, the first end of the slider passage disposed along the side of the slider and the second end of the slider passage disposed at the second end of the slider. The slider has a moveable seal depending from the side thereof, the moveable seal abutting an interior wall of the housing that defines the passage between the stationary seal and the second end of the housing passage. The housing, the slider, the stationary seal and the moveable seal define an expandable chamber, the volume of the chamber increasing as the slider is moved along the housing passage toward the second end. The slider has a bypass in fluid communication with the expandable chamber to permit flow around the stationary seal and into the chamber until the first end of the slider passage abuts the stationary seal.

According to an additional aspect of the present disclosure, a needleless connector includes a housing having a housing passage with first and second open ends, a slider disposed in the passage and having a first and second opposing ends and a side between the first and second ends, and a resilient member disposed between the slider and the housing to bias the slider toward the first end of the housing passage. A movable seal depends from the side of one of the slider and the resilient member and abuts an inner surface of the housing that defines the housing passage. The housing, the slider and the moveable seal define an expandable chamber, the volume of the chamber increasing as the slider is moved along the housing passage toward the second end.

According to a still further aspect of the present disclosure, a needleless connector includes a housing having a housing passage with first and second open ends, a seal disposed at the first end of the housing passage, a slider disposed in the passage and having a first and second opposing ends and a side between the first and second ends, and a resilient member having a first end mounted on the housing and the slider being at least partially disposed in the resilient member. The slider has a slider passage with a first and second open ends, the first end of the slider passage disposed along the side of the slider and the second end of the slider passage disposed at the second end of the slider. The slider has a first state wherein the first end of the slider abuts the seal, and a second state wherein the first end of the slider is spaced from the seal.

According to yet another aspect of the present disclosure, a needleless connector includes a housing having a housing passage with an open end, a slit septum disposed at the open end of the housing passage, a slider disposed in the housing passage and having a first and second opposing ends and a slider passage with first and second open ends, and a resilient member disposed in the housing and biasing the slider toward the open end of the housing passage.

Additional aspects of the disclosure are defined by the claims of this patent.

BRIEF DESCRIPTION OF THE DRAWINGS

It is believed that the disclosure will be more fully understood from the following description taken in conjunction with the accompanying drawings. Some of the figures may have been simplified by the omission of selected elements for the purpose of more clearly showing other elements. Such omissions of elements in some figures are not necessarily indicative of the presence or absence of particular elements in any of the exemplary embodiments, except as may be explicitly delineated in the corresponding written description. None of the drawings are necessarily to scale.

FIG. 1 is a cross-sectional view of a T-site needleless connector according to the present disclosure in a first state;

FIG. 2 is a cross-sectional view of the needleless connector of FIG. 1 in a second state;

FIG. 10 is a cross-sectional view of a T-site needleless connector in a first state;

FIG. 11 is a cross-sectional view of the needleless connector of FIG. 10 in a second state;

FIG. 17 is a cross-sectional view of the needleless connector of FIG. 13 with a priming cap attached;

FIG. 18 is a cross-sectional view of the needleless connector of FIG. 13 with the priming cap attached and depressed to prime the connector;

FIG. 21 is a cross-sectional view of the in-line connector of FIG. 19 in a second state;

FIG. 22 is a cross-sectional view of the in-line connector of FIG. 19 in a third state;

FIG. 23 is a cross-sectional view of the in-line connector of FIG. 19 in a fourth state;

FIG. 28 is a cross-sectional view of a T-site connector in a first state;

FIG. 29 is a cross-sectional view of the in-line connector of FIG. 28 in a second state;

FIG. 36 is a cross-sectional view of a straight in-line connector with an integrated seal/biasing element/tube in a first state;

FIG. 37 is a cross-sectional view of a straight in-line connector with an integrated seal/biasing element/tube in a first state;

FIG. 38 is an end view of the slider used in the connector of FIG. 37;

FIG. 41 is a cross-sectional view of a straight in-line connector with a tension spring and a compression spring in a first state;

FIG. 42 is a cross-sectional view of the connector of FIG. 41 in a second state;

FIG. 43 is a cross-sectional view of the connector of FIG. 41 in a third state;

FIG. 52 is a cross-sectional view of a T-site connector with a tension spring in a first state; and FIG. 53 is a cross-sectional view of the connector of FIG. 52 in a second state.

DETAILED DESCRIPTION OF VARIOUS EMBODIMENTS

Figure 3:
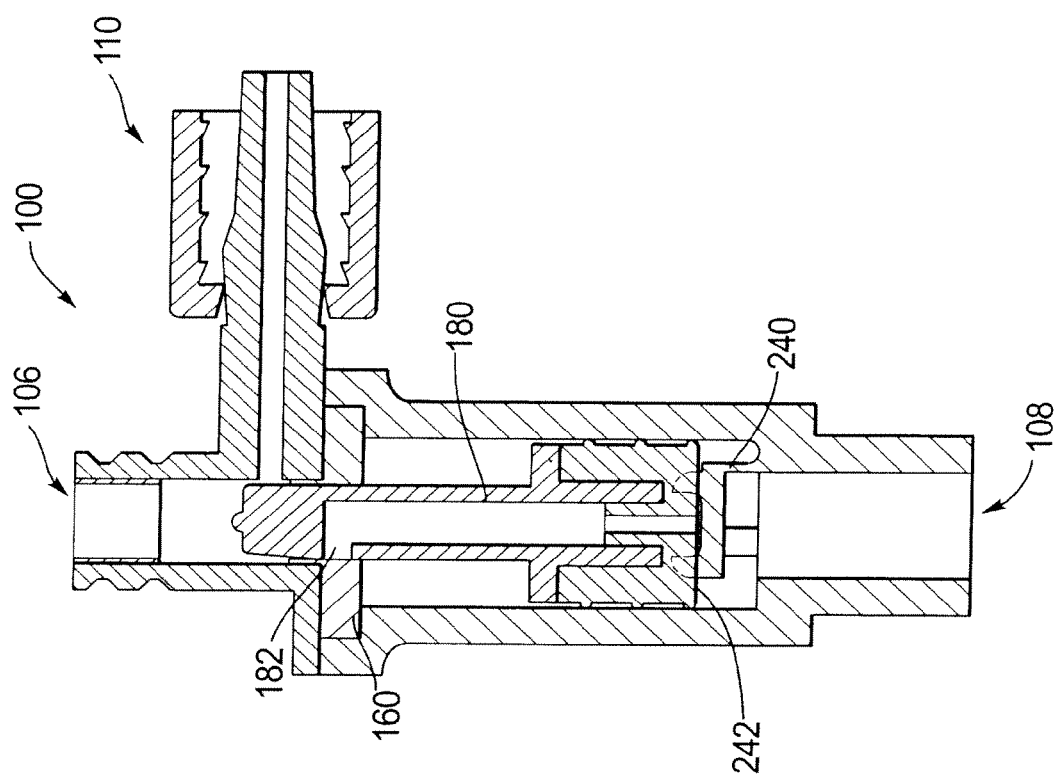
FIG. 3 is a cross-sectional view of the needleless connector of FIG. 1 in a third state.

Although the following text sets forth a detailed description of different embodiments of the invention, it should be understood that the legal scope of the invention is defined by the words of the claims set forth at the end of this patent. The detailed description is to be construed as exemplary only and does not describe every possible embodiment of the invention since describing every possible embodiment would be impractical, if not impossible. Numerous alternative embodiments could be implemented, using either current technology or technology developed after the filing date of this patent, which would still fall within the scope of the claims defining the invention.

It should also be understood that, unless a term is expressly defined in this patent using the sentence "As used herein, the term '_____' is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to in this patent in a manner consistent with a single meaning, that is done for sake of clarity only so as to not confuse the reader, and it is not intended that such claim term be limited, by implication or otherwise, to that single meaning. Finally, unless a claim element is defined by reciting the word "means" and a function without the recital of any structure, it is not intended that the scope of any claim element be interpreted based on the application of 35 U.S.C. §112, sixth paragraph Embodiments of a needleless connector according to the present disclosure are discussed herein. A convention has been used where the direction towards the top of the page is generally referred to as "distal," and the direction towards the bottom of the page is generally referred to as "proximal." It will be recognized that use of this convention is intended to simplify reference to the features as illustrated, not to limit the features to a particular orientation in use, for example.

FIG. 1 illustrates an embodiment of a needleless connector 100. The connector 100 may be used to provide multiple fluid connections with a Luer syringe, a blunt cannula or other instrument. The connector 100 may be attached to a conduit in fluid communication with a patient. The conduit may be a peripheral or central catheter, medical tubing (such as may be used in an intravenous (I.V.) administration set), etc. to form a passageway in fluid communication with the patient for the flow of fluid to the patient. The connector 100 may be used in or connected to other items as well, for example, a vial or vial adapter.

As seen in FIG. 1, the needleless connector 100 includes a housing 102 having a housing passage 104 with first and second open ends 106, 108 and a side port 110. Where the connector 100 is used in place of a conventional T-site, the end 106 may be referred to as the med/sample port leg, the end 108 may be referred to as the flush reservoir leg, and the port 110 may be referred to as the patient leg. A slider 112 (which may also be referred to as a rigid spool) is disposed in the passage 104 and moveable between the first and second ends 106, 108 of the housing passage 104.

As will be noted, the housing 102 is formed of two pieces: the cap 120 and the body 122. The cap 120 includes a first passage 124 that defines a distal section of the passage 104. The first passage 124 is defined in a tubular extension 126 of the cap 120 that has threads 128 formed therein, permitting use of the extension 126 as a female Luer of a Luer-lock type arrangement. The generally cylindrical body 122 includes a passage 130 that defines a proximal section of the passage 104. A distal end 132 of the body 122 is joined to a proximal surface 134 of the cap 120 through the use of ultrasonic welding, for example, to attach the two sections 120, 122 of the housing 102 together.

The cap 120 also includes a second passage 140 that is at right angles relative to the first passage 124, and that defines the port 110. In particular, the second passage 140 may be defined by a tubular extension 142, about which a collar 144 may be disposed. The collar 144 may have threads 146, and may permit the extension 142 to be used as a male Luer in a Luer-lock type arrangement.

A first stationary seal 150 is disposed between the first end 106 of the housing passage 104 and the side port 110. In particular, the first stationary seal 150 may be overmolded to the tubular extension 126 of the cap 120. The seal 150 provides a compression seal against the slider 112. The seal 150 also provides a compression seal against the outer surface of a male Luer disposed into the first end 106 of the housing passage 104; preferably, the seal 150 is sized to provide a compression seal against the male Luer during the entire movement of male Luer into and out of the end 106 of the passage 104. Where a compression seal is provided during the entire stroke length, fluid leakage and/or air aspiration during connection/disconnection may be avoided.

While not illustrated, the opposing surfaces 152, 154 of the seal 150 and slider 112 may have features that provide a fluid-tight closure against even higher pressures than may be resisted by the arrangement illustrated. For example, an annular ring may depend from the surface 154 of the slider 112, which ring further deforms the seal 150. Alternatively, the surface 154 may have a groove or step formed therein, and the surface 152 of the seal may have an inwardly-depending flange or step that is received in the groove or step in the surface 154. Either arrangement may provide further assurance against fluid loss at higher pressures.

A second stationary seal 160 is disposed between the side port 110 and the second end 108 of the housing passage 104. The second stationary seal 160 is in the form of a bushing, which bushing may be formed separately from the housing 102 and held in place through the cooperation of the cap 120 and body 122, or may be overmolded to the cap 120 or the body 122. The seal 160 is formed of an elastomeric material that is stiff enough to resist excessive deflection during movement of the slider 112. The seal 160 has an annular base 162 from which depends a cylindrical extension 164, and a passage 166 passing through the base 162 and the extension 164 and in which is received the slider 112.

The slider 112 has first and second opposing ends 170, 172 and a side 174 between the first and second ends 170, 172. As will be recognized, the side 174 of the slider 112 defines the surface 154 referred to above relative to the seal 150. The side 174 abuts the seal 160 as well.

The slider 112 has a slider passage 180 with a first and second open ends 182, 184. The first end 182 of the slider passage 180 is disposed along the side 174 of the slider 112 and the second end 184 of the slider passage 180 is disposed at the second end 172 of the slider 112. The first end 182 of the passage 180 may be oriented relative to the port 110 so that the end 182 is 180 degrees from the port 110 to facilitate the flushing feature described below.

It will be recognized that the slider passage 180 may have a number of open first ends 182. For example, other embodiments of the slider 112 may include two, three or more openings 182 in the side 174 of the slider 112. The number of openings 182 may be selected to optimize the flushing of the passage 104, as is explained in greater detail below.

The first end 182 of the slider passage 180 is associated with a first section 190 of the slider passage 180, while the second end 184 is associated with a second section 192 of the slider passage 180. While the first and second sections 190, 192 of the passage 180 are illustrated at right angles to each other, this orientation need not be same in all embodiments.

The slider 112 also includes a movable seal 200 disposed on the end 172 of the slider 112. In particular, the seal 200 is defined by a piston, which may be an elastomeric piston. The piston/seal 200 may be formed separately from the slider 112 and then attached to the second end 172 of the slider 112, or the seal 200 may be overmolded thereto. In either event, the slider 112 may have a flange 202 or step that is used to seat the seal 200 onto the second end 172 of the slider 112.

The seal 200 has a passage 204 therethrough which mates with the slider passage 180. The seal 200 also has a surface 206 that abuts an interior wall 208 of the housing 102 that defines the passage 104. To this end, the surface 206 may have a series of outwardly-depending rings 210 to former a more fluid-tight closure between the seal 200 and the housing 102. The seal 200 is disposed between the second stationary seal 160 and the second end 108 of the passage 104.

The housing 102, the slider 112, the second seal 160 and the moveable seal 200 may define an expandable chamber 220. The volume of the chamber 220 increases as the slider 112 is moved along the housing passage 104. Because of the presence of the seals 160, 200, the chamber 220 acts as a vacuum chamber, which may assist in the biasing of the slider 112 toward the state illustrated in FIG. 1. However, according to alternative embodiments, such as are illustrated elsewhere herein, the connector 100 may include a compression spring disposed within the body 122 between the slider 112 (in particular, the piston 200) and a flange or step formed near the second end 108 of the housing passage 104.

The connector 100 may also include an optional sealing structure 240 disposed near the second end 108 of the housing passage 104. The presence of the structure 240 in a particular embodiment of the connector 100 may depend, in part, on how fluid-tight the closure is between the seal 160 and the open end 182 of the slider passage 180. The cup-shaped structure 240 cooperates with a surface 242 of the seal 200 (as best seen in FIG. 3), to form a fluid-tight sealing relationship to limit the leakage of fluid through the slider passage 180. The structure 240 is supported on a plurality of legs 244 that are attached to the structure 240 and the body 122 and define a plurality of slots 246 therebetween in fluid communication with the end 108 of the passage 104; as illustrated, the structure 240 and the legs 244 may be formed integrally (i.e., as one piece) with the body 122.

As illustrated in FIGS. 1-3, the slider 112 has at least three states. It will be recognized that the second state illustrated in FIG. 2 is but merely exemplary of any number of states that exist between the first state illustrated in FIG. 1 and the third state illustrated in FIG. 3. The difference between the states in between the first and third state is one principally of degree, depending upon the distance that the slider 112 travels within the passage 104. It will be recognized that the first, second, and third states occur sequentially as the slider 112 is moved along the housing passage 104.

In the first state, illustrated in FIG. 1, the first end 106 of the passage 104 is sealed by the cooperation of the first seal 150 and the slider 112. In this state, it is possible for fluid to pass through the slider passage 180 between the second end 108 of the passage 104 and the port 110, with little or no dead space. However, it is intended that the passage of fluid through the first end 106 be limited, and preferably prevented.

FIG. 2 illustrates a second state. This state represents the condition of the connector 100 when a male Luer has been disposed into the first end 106 of the passage 104, and cooperates with the first end 170 of the slider to move the slider 112 in the direction of the second end 108 of the passage 104. In this state, the first end 106 of the passage 104 is in fluid communication with the male Luer lumen because of the fluid-tight seal formed between the male Luer stem exterior and surface 152 of the seal 150. As mentioned above, the surface 152 is sized to provide a seal against the male Luer stem exterior for the entire stroke length. Also, in this state, the male Luer lumen is in fluid communication with the second end 108 and the port 110, permitting use of the connector 100 as a 3-way stopcock.

To permit the male Luer and the end 170 of the slider 112 to cooperate with each other without limiting the passage of fluid from the male Luer, an embossment 260 may be formed in the end 170 of the slider 112 to space the male Luer from the surface 262 of the end 170 of the slider 112. Several configurations of embossment 260 may be possible which allow swabbing and disinfection of surface 262 with the slider 112 in the first state illustrated in FIG. 1, and which provide adequate flow rate with male Luer connected in the second and third states illustrated in FIGS. 2 and 3. Still further options are possible for the structure of the embossment 260 in an embodiment, similar to those illustrated in FIGS. 44-49, where a seal is disposed so as to completely cover the end 106 of the connector 100, access occurring through a slit in the seal. Such an arrangement may provide a continuous, swabable external surface, thereby removing the need for embossment 260 to be swabable and permitting further alternative embossment possibilities.

FIG. 3 illustrates the third state, wherein the first end 182 of the slider passage 180 is sealed by the second seal 160. In this state, medication may be administered to the patient through the port 110, which may be connected to an extension set in fluid communication with a catheter that has been placed into a patient's vein, for example. The first end 106 is in fluid communication with the port 110, again with little or no dead space. The medication will not pass through the second end 108 of the connector 100 because of the seal 160, and optionally the seal structure 240.

It will be recognized that the connector 100 is self-priming. That is, in the first state, a fluid path exists between the second end 108 of the passage 104 and the port 110. As a consequence, fluid is already in the distal section of the passage 104, which is proximate to the first end 106 of the passage 104 that may be used as the med/sample port.

Figure 5:
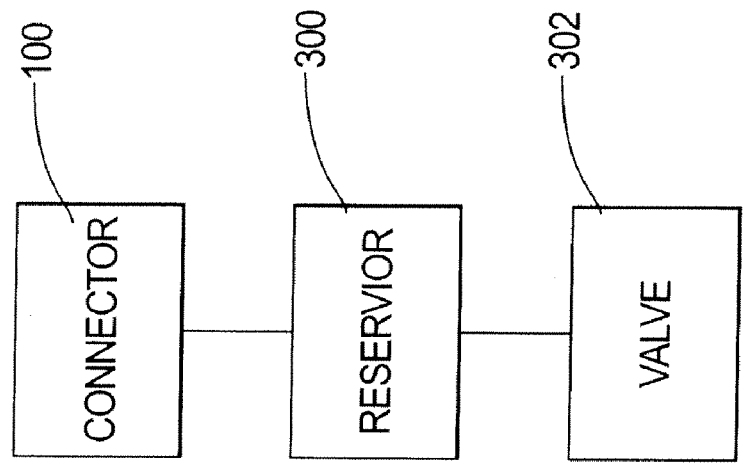
FIG. 5 is a schematic view of an automatic flush system incorporating the needleless connector of FIG. 1.
Figure 4:
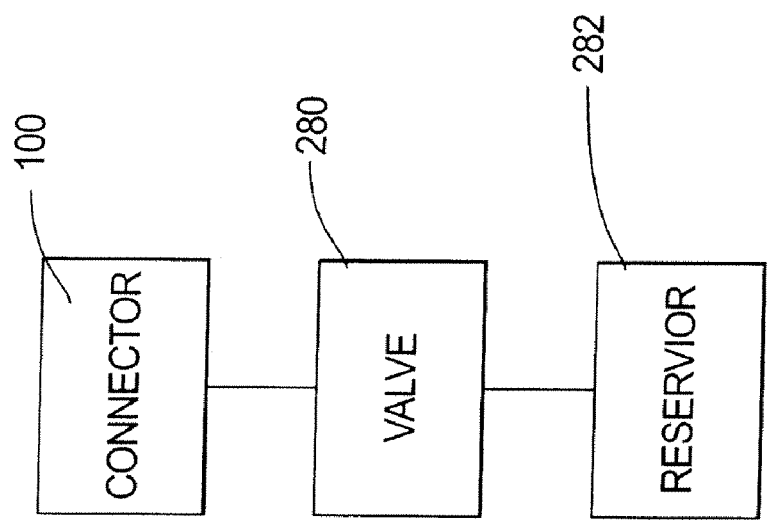
FIG. 4 is a schematic view of a manual flush system incorporating the needleless connector of FIG. 1.

Additionally, when the connector 100 returns to the first state from the third state, the connector 100 may be completely flushed without further access through the first end 106 of the connector 100 (i.e., the med/sample port). There is no dead space within the connector 100 between the seals 150, 160, and thus no chance for residue to remain in the connector 100 once flushed. Whether the flush is performed automatically or manual is an option dependent upon the other elements of the system. FIGS. 4 and 5 illustrate two flush systems, one for automatic flush and the other for manual flush.

FIG. 4 schematically illustrates an infusion system for use in manual flush of the connector 100 after removal of the male Luer from the first end 106. A manually-operated valve 280 is connected between a pressurized reservoir 282 filled with flush solution and the second end 108 of the passage 104 of the connector 100. Opening the valve 280 would permit the flow of fluid into the connector 100 to flush the connector 100.

FIG. 5 illustrates an infusion system for use in automatic flush of the connector 100 after removal of the male Luer from the first end 106. It will be recognized that when the slider returns to the first state from the third state, a reflux volume will be drawn into the connector 100 from the path of least resistance. If a valve is disposed upstream of the connector 100 between the connector 100 and any flush reservoir, the reflux volume may be drawn from the extension set and catheter via the port 110, depending on the relative resistances. However, by placing a reservoir 300 between the connector 100 and a check valve 302, the reflux volume may be drawn from the reservoir 300, permit flushing of the connector without action by the healthcare professional.

One advantage of the manual system just described over the automatic flush system is in regard to use of the first end 106 of the connector 100 as a sample port. By using a manual flush valve between the flush reservoir and the connector that may be opened or closed, the user may choose to have the reflux volume drawn from the patient. Accordingly, a syringe disposed through the end 106 of the passage 104 may be used to draw a series of samples from the patient. The connector 100 may be finally flushed only when the sampling is complete.

Selection and position of a manually-operated valve, as opposed to a fixed one-way valve, proximal to the second end 108 will depend on the intended therapy (infusion or sampling). For infusion therapy, a fixed one-way valve proximal to the second end 108 will force displacement of fluid in the passage 104 through the passage 140 during connection of the male Luer, effectively providing a catheter flush prior to medication infusion (the first saline flush in the SAS procedure). During removal of the male Luer, the passage 104 will re-fill with flush solution or blood depending on relative resistances of the end 108 relative to the port 110. Therefore, a low-cracking pressure check valve is desirable for the end 108 to minimize reflux of blood into the passages 140, 180, and 104 prior to flushing from the end 108. Adding a manually-operated valve would allow collection of more than one blood sample by serial connection of syringes.

It will be recognized that the connector 100, similar to other connectors described herein, may not be as useful in methods of blood sampling as other connectors. In particular, if a serial connection of a plurality of syringes was used to withdraw more than one sample, the connector 100 would cause dilution of the samples because of the automatic flush performed on connection and disconnection. As a consequence, the connector 100 may be most useful with a "vacuum tube adapter" method of blood sampling, because the male Luer of the vacuum tube adapter needs only one connection to the med/sample port to allow sampling using several sample tubes in series. However, connectors are described herein, for example in FIGS. 13-16, which may be used with other methods of blood sampling, such as may accommodate discard reinfusion.

It will be appreciated that the stationary and fixed seals may have formulation ingredients or coatings that either increase or decrease the coefficient of friction of the seal, for example, relative to particular materials. For instance, it may be desirable for the first stationary seal 150 to have a relatively higher coefficient of friction relative to materials typically used for male Luers (such as polycarbonate, polypropylene, ABS, etc.) and a relatively lower coefficient of friction relative to materials typically used for the slider 112. As a further example, it may be desirable for the moveable seal 200 to have a relatively low coefficient of friction relative to the material of the housing 102.

FIGS. 6-9 illustrate variants of the connector 100, wherein a chamber is provided that will flush the port 110 automatically upon insertion of a male Luer into the end 106 of the passage 104 and upon removal of the male Luer. As such, this configuration may provide an automated alternative to the SAS procedure performed conventionally using manual flushing with syringes. This insertion/removal flush may be supplemented with a flush using a manual system, such as is illustrated in FIG. 4, provided the pressure of the manual flush exceeds the crack pressures of the check valves used with the connectors, as explained in greater detail below.

Figure 6:
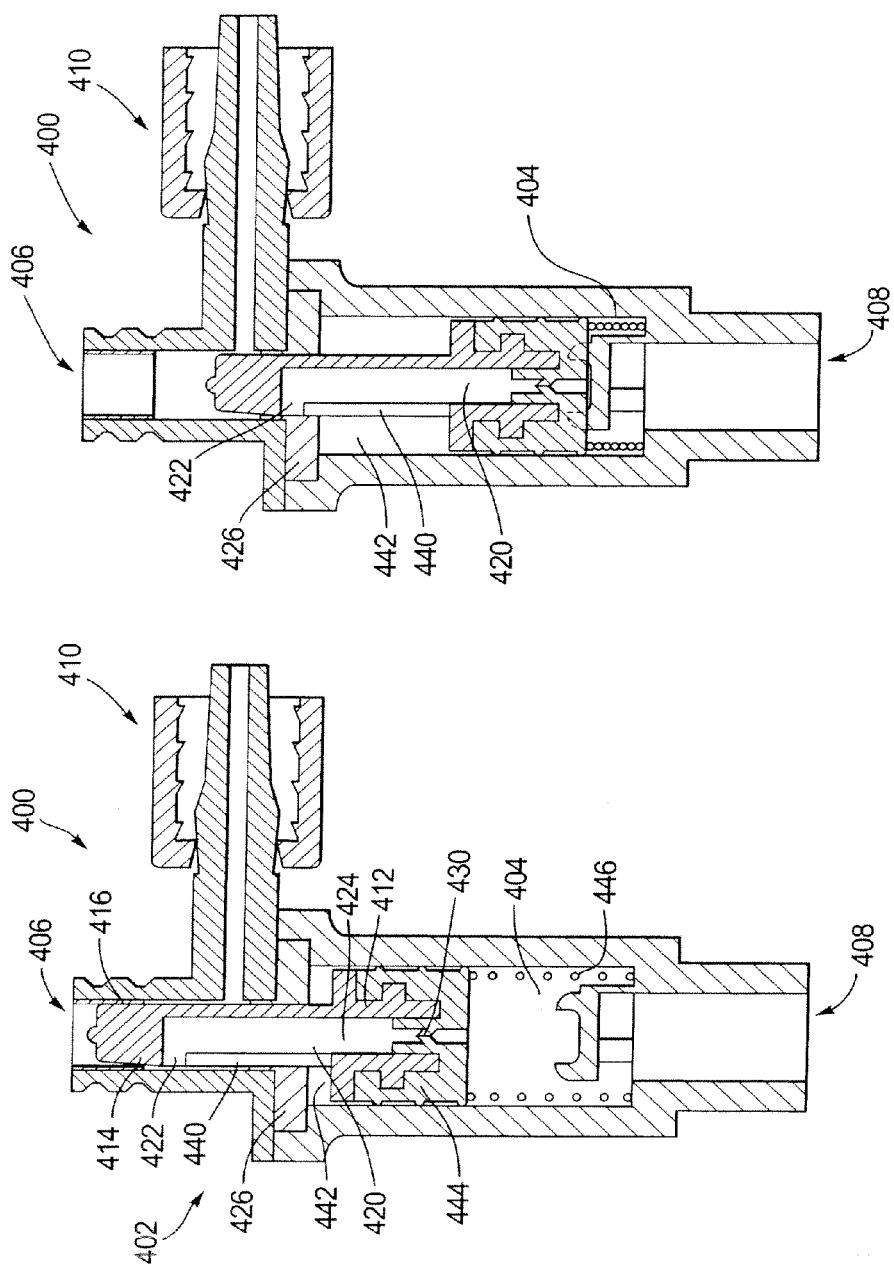
FIG. 6 is a cross-sectional view of a T-site needleless connector having insertion/removal flushing in a first state.

Referring first to FIG. 6, it will be recognized that many features of the connector 400 are shared in common with the connector 100. This will also be true of the connector 500 of FIGS. 8 and 9. Consequently, rather than repeat the entirety of the discussion relative to the similarities, the focus will be primarily on the differences between the variants, with discussion of the similar structures as is necessary to discuss the operational differences between the variants.

Figure 7:
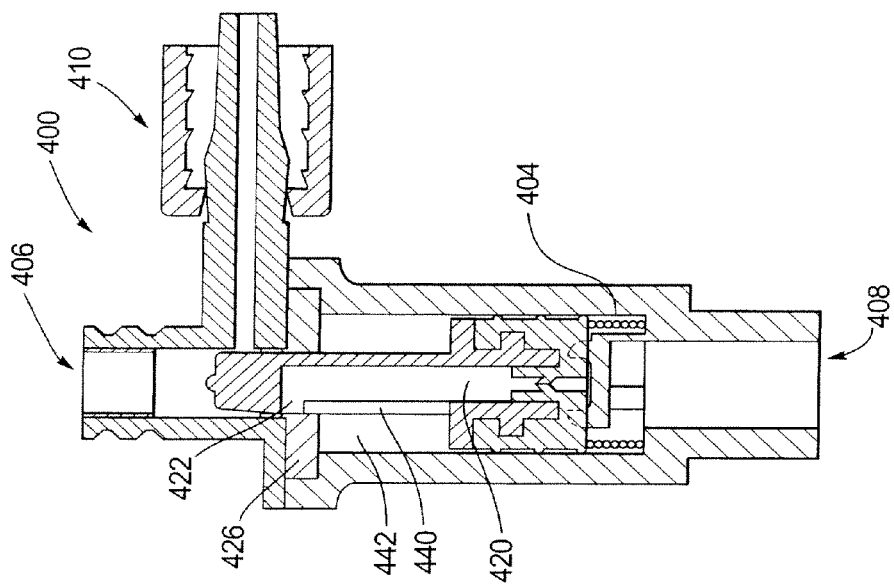
FIG. 7 is a cross-sectional view of the needleless connector of FIG. 6 in a second state.

As seen in FIG. 6, the connector 400 includes a housing 402 with a passage 404 having first and second ends 406, 408 and a side port 410. A slider 412 is disposed in the passage 404, and has a first end 414 that mates with a seal 416 to close the first end 406 of the passage 404. The slider 412 has a slider passage 420 therethrough with first and second ends 422, 424. The slider passage 420 places the second end 408 of the passage in fluid communication with the port 410 even when the first end 406 is sealed according to the mating of the first end 414 of the slider and the seal 416. The connector 400 also includes a seal 426 (in the form of a bushing) which forms a fluid tight seal with the first end 422 of the slider passage 420 to prevent fluid communication between the second end 408 of the connector 400 and the port 410, as seen in FIG. 7.

Unlike the connector 100, the slider 412 includes a check valve 430 disposed at the second end 424 of the slider passage 420. The check valve 430 limits flow in the direction of the second end 424 of the slider passage 420 from the first end 406 of the passage 404 and the port 410.

Also unlike the connector 100, the slider 412 includes a bypass 440. The bypass 440 is for use with a chamber 442 defined by the housing 402, the slider 412 and a seal 444 (in the form of a piston) attached to the slider 412. Preferably, the check valve 430 is molded integral to seal 444, and could therefore be referred to as an integral check valve 430.

In the embodiment according to FIGS. 1-3, a chamber similar to the chamber 442 was formed, but was sealed by the cooperation of the seal 160 and the slider 112. The bypass 440 permits fluid to enter the chamber 442 until the first end 422 of the slider passage 420 is closed (see FIG. 2) around the seal/bushing 426. Because no vacuum chamber is present to bias the slider 412 toward the first end 406 of the passage 404, a compression spring 446 is included.

It will be recognized that the connector 400 may also be used with an additional check valve proximal to the passage 404. To distinguish it from integral check valve 430, this additional check valve may be referred to as the proximal check valve. The proximal check valve could be incorporated into a tubing segment bonded to second end 408, or could be incorporated directly to end 408 without an intermediate tubing segment. The function of this additional check valve will be discussed during consideration of intended operation, below. Frankly, one advantage of connector 400 relative to the connector 100 is that both the integral check valve 430 and the proximal check valve may be designed to have relatively high cracking pressures, which may facilitate manufacturability. Because the connector 100 lacks a chamber such as the chamber 442, any check valve used with the connector 100 must have relatively low cracking pressure to prevent excessive blood reflux during male Luer withdrawal.

In operation, a male Luer (or similar instrument) is inserted into the first end 406 of the passage 404, causing movement of the slider 412 in the direction of the second end 408. As the slider 412 moves in the direction of the second end 408, the fluid already present in the passage 404 is discharged from the connector 400 through the port 410 and into the chamber 442 via the bypass 440 because of the presence of the proximal check valve. The relative percentages of the volume contained in the passage 404 that will discharge through the side port 410 (to the patient catheter) or into the chamber 442 may be influenced by chamber geometry. The volume of the pre-infusion flush (comparable with the first saline flush in the conventional SAS technique) can therefore be defined by the difference between the volume of the passage 404 and the volume of the chamber 442. When the slider 412 reaches the state in FIG. 7, the chamber 442 will be closed. Selecting the dimensions of the open end 422 such that it seals off only after complete male Luer connection may assist in minimizing "attachment reflux" of blood through the side port 410.

In the state illustrated in FIG. 7, the male Luer connected to first end 406 is in fluid communication with the side port 410. This allows medication infusion to the patient because the passage 420 and the bypass 440 are sealed off and the integral check valve 430 further prevents flow from the first end 406 to the second end 408. For that matter, sealing off the open end 422 may even be more important when taking blood (or other bodily fluid) samples, because the negative pressure required to draw a sample could open the integral check valve 430.

When the male Luer is withdrawn, the slider 412 moves in the direction of the first end 406, causing fluid to be discharged from the chamber 442 through the bypass 440 and the open end 422. The fluid discharged from the chamber 442 passes through the port 410, given the presence of the valve 430 preventing fluid flow through the end 424 of the slider passage 420. The volume of flush solution delivered during male Luer withdrawal (the second saline flush in the conventional SAS procedure) can be influenced by design of the volume of the chamber 442. At the same time, fluid is drawn through the end 408 of the housing passage 404 to fill the space between the slider 412 and the housing 402 according to the volume of the chamber/passage 404.

It will be recognized that the operation of this variant relies upon certain compliances, both as the chamber 442 is filled and as fluid is discharged from the chamber 442. The compliances during filling may be accommodated through the design of the seal 444 and the valve 430, for example. The compliances during discharge may also be accommodated through the design of the seal 444, as well as the seal 426.

At this point, it may be helpful to highlight certain distinctions between the connectors of the present disclosure, such as the connector 400, and existing connectors. Because of the inclusion of the integral and proximal check valves and the return mechanism for the piston 444 (in the form of the spring 446), it is not necessary to provide a driving pressure in or on the flush reservoir. As a consequence, the flush reservoir does not have to be disposed at a higher elevation than the connector 400 to take advantage of gravity. Nor does the flush reservoir have to include an elastomeric or other pumping mechanism. The pumping action integral to the connector 400 thus provides flexibility in the type and position of the flush reservoir. For example, the flush reservoir could be an inexpensive pouch carried by the patient on their person in the form of a belt attachment, rather than in the form of an expensive elastomeric reservoir or a conventional IV bag hung above the connector or connected to a pressure cuff. If the flush solution is not propelled by gravity, care must be taken to eliminate risk of air infusion by providing connector, extension set, and reservoir designs that facilitate complete priming. Alternatively, an air-eliminating filter could be included in the extension set.

It will also be recognized that with a connector, such as the connector 400, with an integral pumping action (caused by the introduction and removal of the male Luer), it may be necessary to further consider the initial priming of the connector and associated infusion or extension tubing. For example, where the connector and the extension set are be connected to the flush solution reservoir by the manufacturer, the set could be initially primed at the manufacturing facility. Where the medical professional connects the extension set to the flush reservoir, priming could be accomplished in a connector 400 configured as in FIGS. 6 and 7 by squeezing the flush reservoir to overcome the cracking pressure of the check valves and expel air (from the connector 400 and the set) prior to attachment of side port 410 to a catheter attached to the patient via the extension set.

It will be recognized that the method of initial priming may also be influenced by whether the connector is configured to be "normally open" or "normally closed." For the connector 400, in the state illustrated in FIG. 6, the fluid path from the flush reservoir (attached to the second end 408) to patient (attached to the side port 410) is normally open for the connector 400. In this state, a "freeflow" condition could occur if the patient inadvertently squeezed (or sat on) the associated flush reservoir. To prevent inadvertent freeflow, the dimensions of the seal 416 and the open end 422 may be selected to occlude flow even in the state of FIG. 6, irrespective of the state of an auxiliary manual tubing clamp. In such a case, the connector may be said to be "normally closed," and a priming cap, as illustrated in FIGS. 17 and 18, may be needed for the initial priming.

Figure 8:
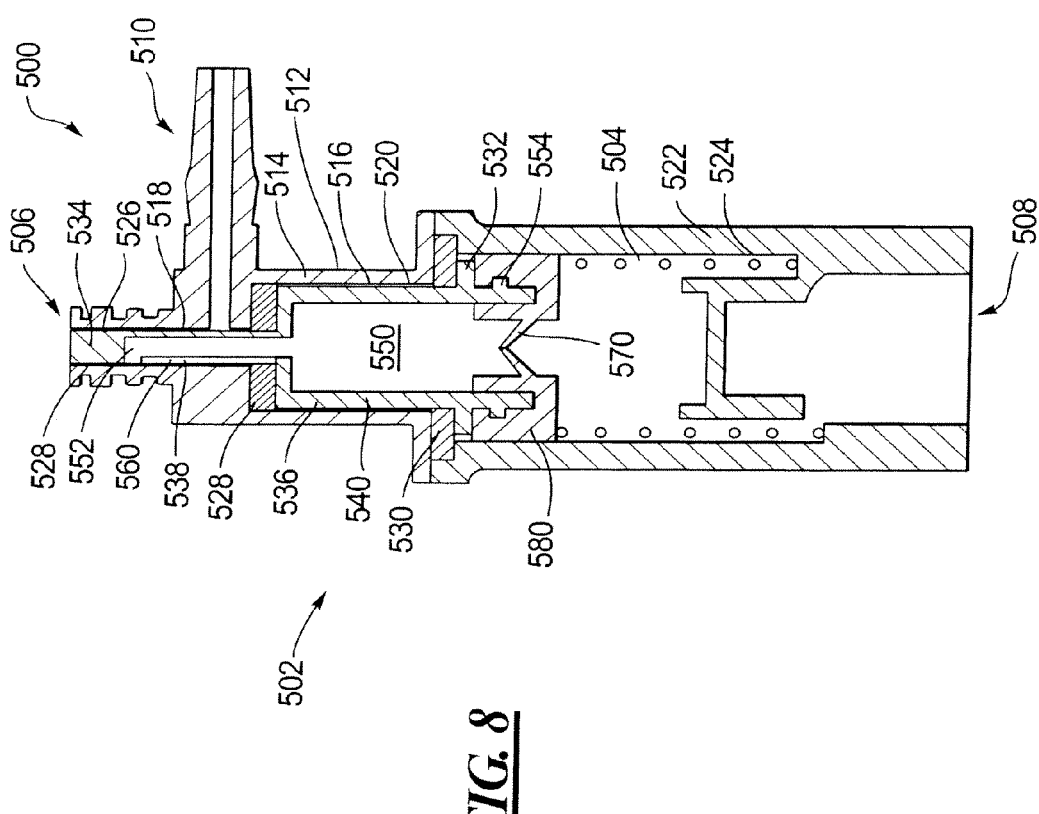
FIG. 8 is a cross-sectional view of another T-site needleless connector having insertion/removal flushing in a first state.
Figure 9:
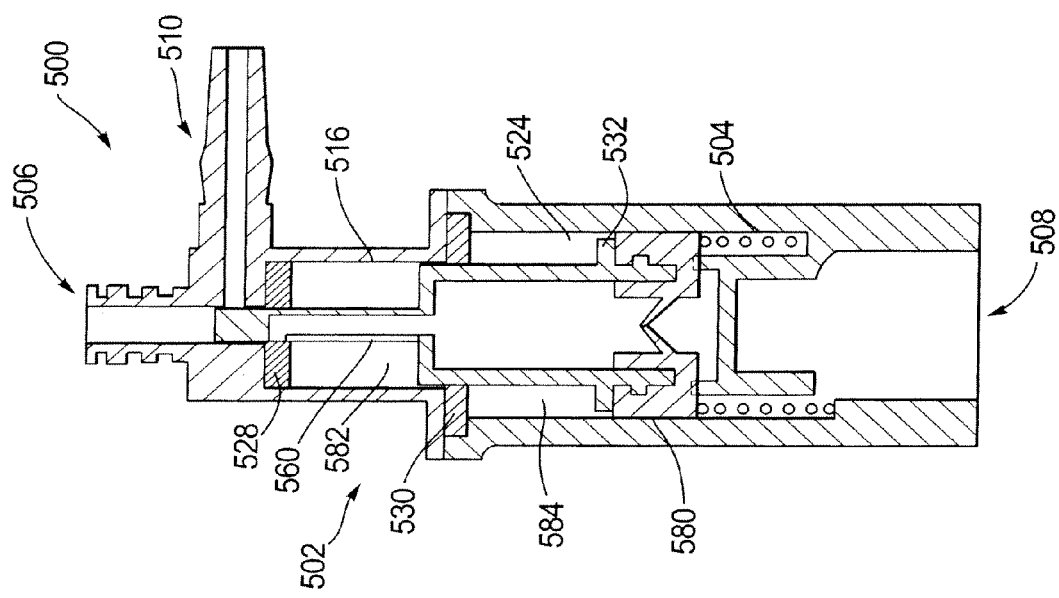
FIG. 9 is a cross-sectional view of the needleless connector of FIG. 8 in a second state.

A further variant of the connector is illustrated in FIGS. 8 and 9. As seen in FIG. 6, the connector 500 includes a housing 502 with a passage 504 having first and second ends 506, 508 and a port 510. Unlike the housings 102, 402 in the connectors 100, 400 of FIGS. 1-3 and 6-7, the housing 502 has a cap 512 with a stepped wall 514 defining a passage 516 with distal and proximal sections 518, 520 that are of different cross-sectional area (in a plane perpendicular to the plane of the page). The housing 502 also includes a body 522 having a passage 524, but similar to the embodiments above, the passage 524 is of a substantially constant cross-sectional area.

Three stationary seals are used in the connector 500. A first seal 526 is disposed at the first end 506 of the passage 504. A second seal 528 (in the form of a bushing) is disposed at the interface between the distal and proximal sections 518, 520 of the passage 516 in the cap 512. A third seal 530 (also in the form of a bushing) is disposed at the interface between the cap 512 and the body 522, and may be maintained in place through cooperation of the cap 512 and the body 522 when the cap 512 is joined (by ultrasonic welding, for example) to the body 522.

A slider 532 is disposed in the passage 504, and has a first end 534 that mates with a seal 526 to close the first end 506 of the passage 504. The slider 532 also has a stepped wall 536 that conforms to the passage 516 defined by the stepped wall 514 of the cap 512. That is, the slider 532 has distal and proximal sections 538, 540 that are of different cross-sectional area, similar to the distal and proximal sections 518, 520 of the passage 516 in which the slider 532 is disposed.

The slider 532 has a slider passage 550 therethrough with first and second ends 552, 554. The slider passage 550 places the second end 508 of the passage 504 in fluid communication with the port 510 even when the first end 506 is sealed according to the mating of the first end 534 of the slider 532 and the seal 526. The slider 532 also includes a bypass 560, which bypass permits flow around the seal 528, but not the seal 530.

Similar to the connector 400, the connector 500 includes a check valve 570 (or integral check valve) and a proximal check valve attached to the second end 508. The integral check valve 570 prevents flow through the second end 552 of the slider passage 550. The proximal check valve assists in providing the flush solution propulsion mechanism integral to the connector 500, which provides for the flexibility in type and location of flush solution reservoir as described above relative to the connector 400.

As a consequence of the stationary seals 526, 528, 530 and a moveable seal 580 (in the form of a piston), two separate chambers 582, 584 are formed, as best seen in FIG. 9. The first chamber 582 is defined by the housing 502, the slider 532, and the third seal 530. The chamber 582 may fill with fluid during the insertion of a male Luer into the end 506 of the housing passage 504, and discharge fluid during the return of the slider 532 in the direction of the first end 506. The second chamber 584 is defined by the housing 502, the slider 532, the third seal 530 and the moveable seal 580. The chamber 584, similar to the chamber of the connector 100 in FIGS. 1-3 is a vacuum chamber, and may be used to bias the slider 532 toward the first end 506 of the passage 504 instead of or in addition to a compression spring.

The connector 500 provides separate control of the volume to be discharged during the insertion of the Luer into the connector 500 and discharged during the removal of the Luer from the connector 500. That is, the cross-sectional area of the passage 524 (and thus the seal/stopper 580) and the length of the stroke (caused by the cooperation of the male Luer with the slider 532) will dictate the amount of fluid discharged into the chamber 582 and out of the port 510. Similarly, the cross-sectional area of the passage 516, the cross-sectional area of the distal section of the slider 532 and the length of the stroke will dictate the amount of fluid discharged from the chamber 582 during removal of the male Luer. Because the cross-sectional areas of the passages 516, 524 (and the slider 532) may be determined separately, unlike the embodiment of FIGS. 6 and 7, the discharged volumes may be varied as well.

An unillustrated variant of the connector 500 would involve removal of the third seal 530. The removal of the third seal 530 would permit the volumes of both chambers 582, 584 to be used for discharge during the removal of the male Luer. Use of both chambers 582, 584 may provide even additional possibilities for control of the volumes discharged through the port 510 during insertion and removal. However, because the chamber 584 would not be available for use as a vacuum chamber, a compression spring or the like would need to be provided to bias the slider 532 toward the first end 506 of the passage 504.

Figure 12:
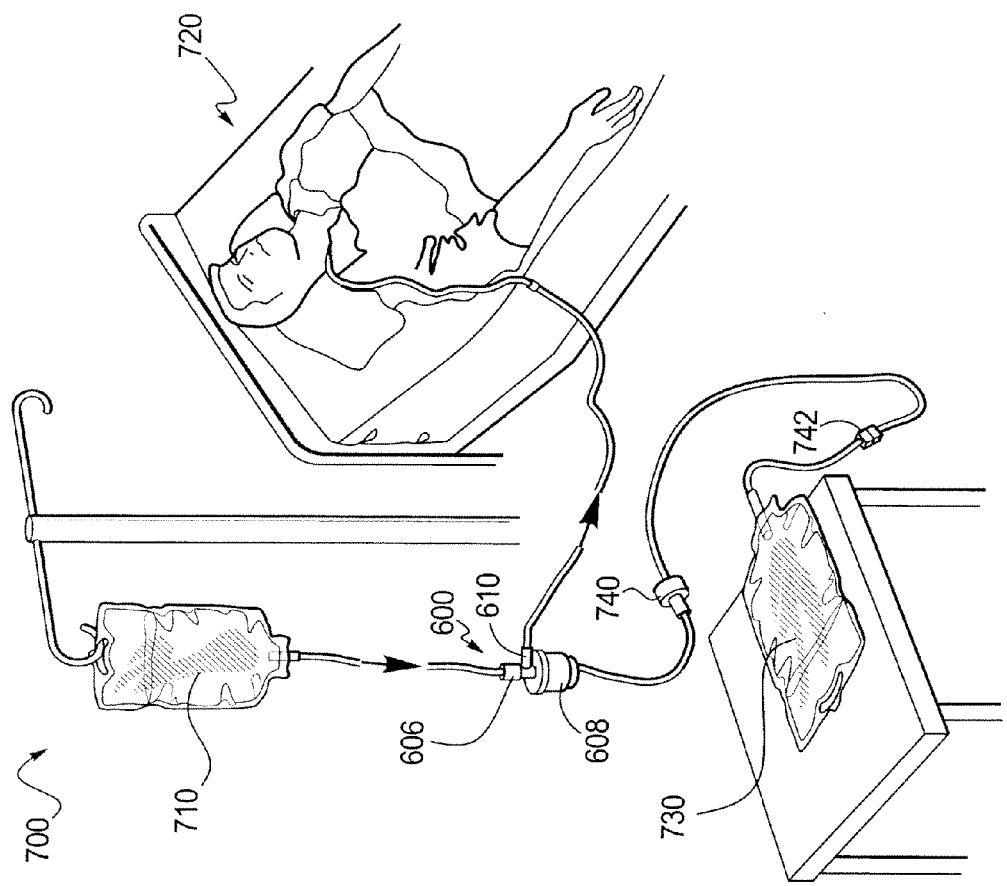
FIG. 12 is a perspective view of an infusion system including the connector of FIG. 11.

It will be recognized that still other variants are possible. FIGS. 10-16 illustrate certain of these additional variants. For instance, FIGS. 10-12 illustrate a variant with self-priming features and insertion/removal flushing features, but including a different slider design than is present in FIGS. 1-3 and 6-9. FIGS. 13-16 illustrate a variant that lacks self-priming features, but includes freeflow prevention, insertion/removal flushing features and an ancillary slider for serial blood sampling. Thus, it will be recognized that the self-priming, automatic flushing and insertion/removal flushing features may be present individually or in combination in a particular embodiment of the present disclosure, and may even be combined with still other features as well. However, self-priming and freeflow prevention may be mutually exclusive features.

Referring then first to FIGS. 10 and 11, a needleless connector 600 includes a housing 602 having a housing passage 604 with first and second open ends 606, 608 and a side port 610. A slider 612 is disposed in the passage 604 and moveable between the first and second ends 606, 608 of the housing passage 604.

As was the case with the variants discussed above, the housing 602 is formed of two pieces: the cap 620 and the body 622. The cap 620 includes a first passage 624 that defines a distal section of the passage 604. The first passage 624 is defined in a tubular extension 626 of the cap 620 that has threads 628 formed therein, and a second passage 630 is defined in a tubular conduit 632 that is disposed at right angles relative to the first passage 624. Unlike the variants above, the tubular conduit 632 is sized to receive a tube 634 that may be connected to a Luer, as opposed to being sized to accept a Luer directly. The generally cylindrical body 622 includes a passage 636 that defines a proximal section of the passage 604. The cap 620 is joined to the body 622 through the use of ultrasonic welding, for example.

A first stationary seal 650 is disposed between the first end 606 of the housing passage 604 and the side port 610, which seal 650 may be overmolded to the cap 620. A second stationary seal 660 (in the form of a bushing) is disposed between the side port 610 and the second end 608 of the housing passage 604. A moveable seal 670 (in the form of a piston) is attached to the slider 612, and is moveable therewith relative to the housing 602. Similar to the variants of FIGS. 8 and 9, the slider 612 also includes a bypass 680, a check valve 682, and a compression spring 684. Similar to the connectors 400 and 500, the connector 600 would also have a proximal check valve connected to the end 608 to allow flexibility in type and position of the flush solution reservoir connected thereto.

The connector 600 operates similar to the immediately preceding variants, in that an expandable chamber 690 is defined by the housing 602, the slider 612, and the moveable seal 670 and the bypass 680 permits fluid to enter and exit the chamber 690. However, the separate sealing structure is not present to close the slider passage 692, this passage 692 being closed through the cooperation between the seal 670 and a surface 694 of the housing 602. Moreover, the connector 600 illustrates that the relative sizes of the volumes used to self-flush the connector during the insertion and disconnection of a male Luer with the connector may be significant.

FIG. 12 illustrates one configuration of an infusion system 700 including the connector 600. As illustrated, the connector 600 has the first end 606 in fluid communication with a container 710 from which fluid is being infused to the patient 720. The port 610 is in fluid communication with the patient 720 via a catheter, for example. The second end 608 of the connector 600 is connected to a container 730 from which flush solution may be administered, the connection being formed via a check valve 740 and an on/off clamp 742. In such a configuration, the connector 600 may form part of an extension set connected to the catheter, and may be manually flushed (through the operation of the on/off clamp 742) once the container 710 has been disconnected from the end 606.

As noted above, it is not a requirement that the container 730 (the flush solution reservoir) be elevated above the connector 600 because of the integral pumping action provided. Additionally, the proximal check valve 740 may be positioned anywhere proximal to the integral check valve 682 depending on desired flush volumes and system compliance. Therefore, container 730 could be simpler and less expensive than conventional IV bags, and could be positioned to allow patient ambulation. Priming means for the system in FIG. 12 would be defined depending on the desire for integral free-flow prevention. Container 730 could be provided pre-filled or empty with a resealable medication port, which allows the user to customize flush solutions for certain patients.

Although the system of FIG. 12 is illustrated in use with a gravity-drip system, it will be recognized that the system illustrated in FIG. 12 could be advantageously used with an ambulatory patient, and in particular an ambulatory patient self-administering his or her own therapy. According to such a system, a syringe may be substituted for the illustrated container 710, the syringe being used to administer a bolus injection. Alternatively, an elastomeric reservoir may be substituted to provide a continuous infusion. According to either substitution, the patient could perform the required post-injection or post-infusion flush simply by disconnecting the container from the connector 600. In this ambulatory patient scenario, the patient could self-administer medication doses according to a prescribed schedule with a limited effort, additional connections, and flush syringes. Depending on the schedule, the flush reservoir may be replaced by a healthcare professional during periodic (e.g., weekly) examinations, although otherwise the system may permit self-administration with minimal intervention by the healthcare professional.

Figure 13:
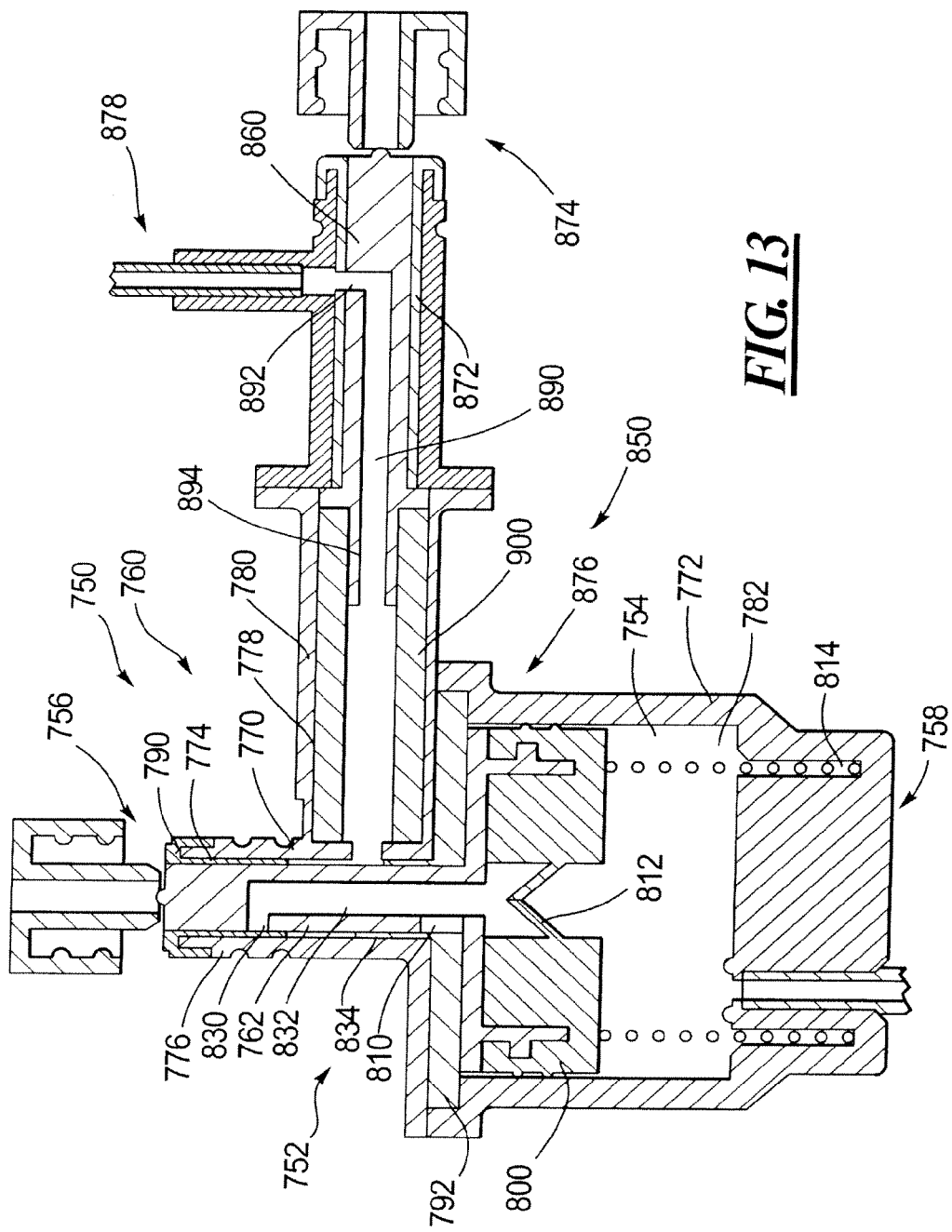
FIG. 13 is a cross-sectional view of a T-site needleless connector having an a primary and an ancillary slider with the primary slider in a first state and the ancillary slider in a first state.
Figure 14:
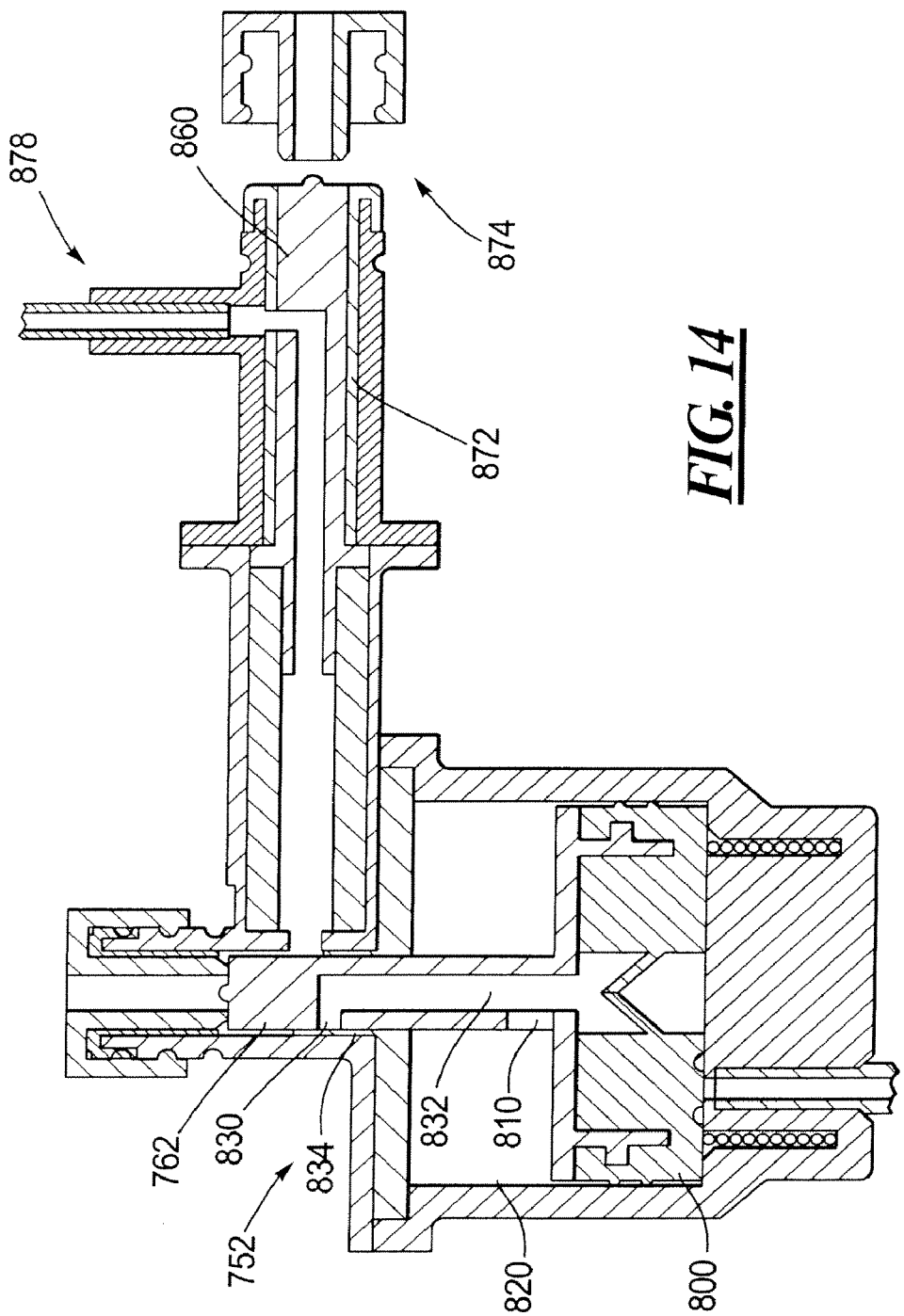
FIG. 14 is a cross-sectional view of the needleless connector of FIG. 13 with the primary slider in a second state and the ancillary slider in a first state.
Figure 15:
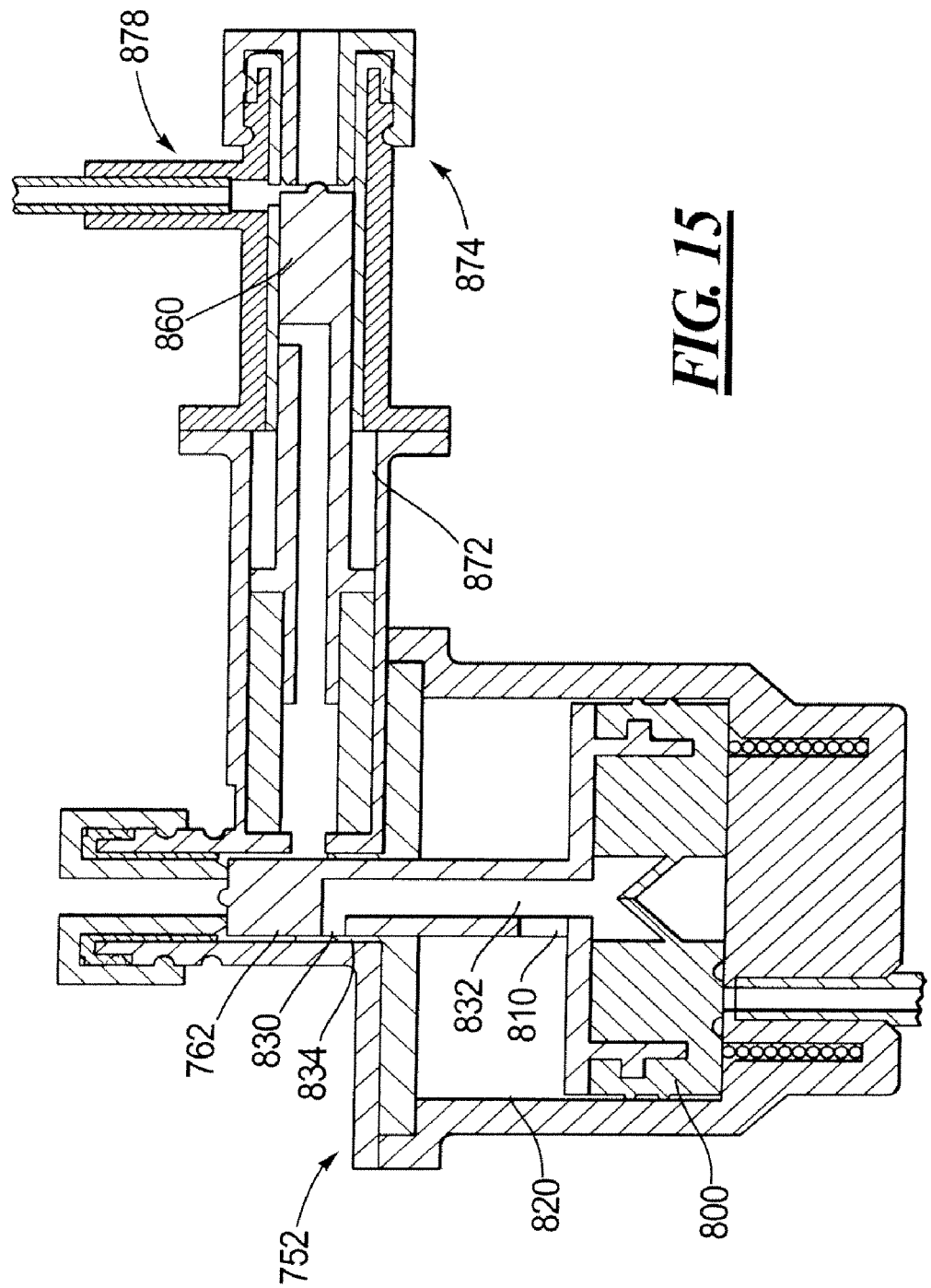
FIG. 15 is a cross-sectional view of the needleless connector of FIG. 13 with the primary slider in a second state and the ancillary slider in a second state.

While a useful configuration, the system 700 in FIG. 12 may be difficult to use where serial blood samples need to be taken by syringe. In such a setting, a different connector 750 may be used, as is illustrated in FIGS. 13-15. While the connector resembles that of FIGS. 10 and 11, the differences are important.

The needleless connector 750 has a housing 752 having a housing passage 754 with first and second open ends 756, 758 and a side port 760. The shape of the side port 760 is significantly different than that of FIGS. 10 and 11 as explained in greater detail below. A slider 762 is disposed in the passage 754 and moveable between the first and second ends 756, 758 of the housing passage 754.

As was the case with the variants discussed above, the housing 752 is formed of two pieces: the cap 770 and the body 772. The cap 770 includes a first passage 774 that defines a distal section of the passage 754. The first passage 774 is defined in a tubular extension 776, and a second passage 778 is defined in a tubular conduit 780 that is disposed at right angles relative to the first passage 774. The generally cylindrical body 752 includes a passage 782 that defines a proximal section of the passage 754. The cap 770 is joined to the body 772 through the use of ultrasonic welding, for example.

A first stationary seal 790 is disposed between the first end 756 of the housing passage 754 and the side port 760, which seal 790 may be overmolded to the cap 770. A second stationary seal 792 is disposed between the side port 760 and the second end 758 of the housing passage 754. A moveable seal 800 is attached to the slider 762, and is moveable therewith relative to the housing 752. The slider 762 also includes a bypass 810, a check valve 812, and a compression spring 814.

The connector 750 operates similar to the immediately preceding variants, in that an expandable chamber 820 is defined by the housing 752, the slider 762, and the moveable seal 800 and the bypass 810 permits fluid to enter and exit the chamber 820 (see FIGS. 14 and 15). However, in the state illustrated in FIG. 13, a first end 830 of a slider passage 832 is covered by the first stationary seal 790, and the bypass 810 is covered by an extension 834 of the second seal 792. Consequently, with the slider 762 fully advanced in the direction of the end 756, no fluid can enter the port 760 from the second end 758 of the connector 750. Thus, the first part of the connector 750 (controlled through the motion of the slider 762) is not self-priming. Rather, this configuration provides freeflow prevention.

As mentioned above, the port 760 is actually part of a housing 850 that houses a second slider 860 that provides for access to the fluid path in which the connector 750 is attached. In particular, the housing 850 includes a passage 872 having first open end 874, a second open end 876 (defined by the port 760), and a side port 878. The slider 860 is received within the passage 872 and is moveable therein between the first end 874 and the second end 876.

The slider 860 has a passage 890 with a first open end 892 and a second open end 894. As illustrated in FIG. 13, the first end 892 is aligned with the port 878 with the slider 860 advanced in the direction of the first end 874. The slider 860 is biased in this direction by a compression spring 900.

Figure 16:
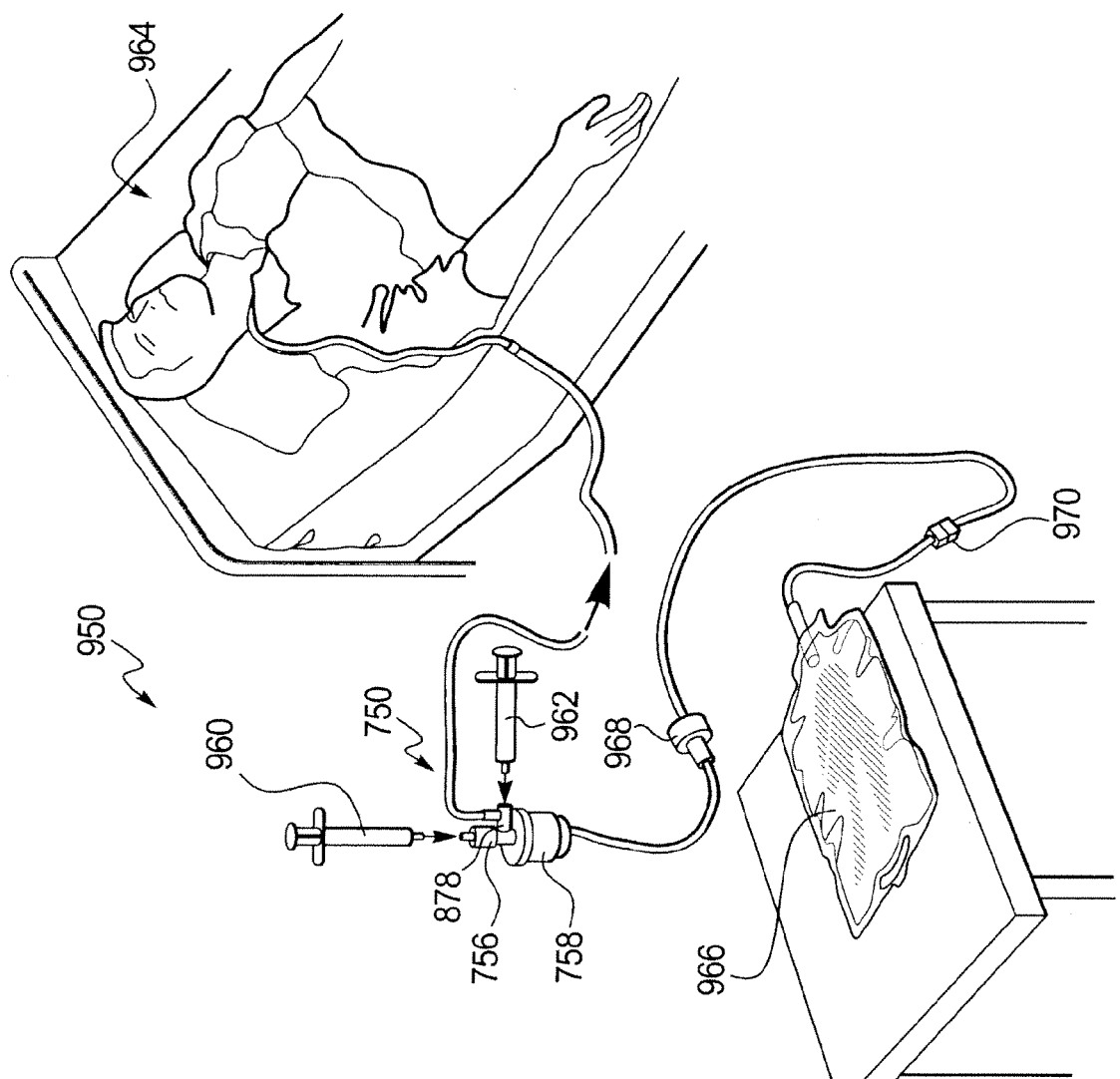
FIG. 16 is a perspective view of a sampling system including the connector of FIG. 13.
Figure 20:
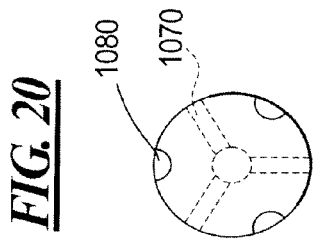
FIG. 20 is an end view of the slider used in the connector of FIG. 19.

The connector 750 may be incorporated into a system 950 as is illustrated in FIG. 16. A syringe 960 to be connected to the first end 756 of the housing passage 754 is illustrated. A second syringe 962 may be connected to the end 874 as also illustrated. As further illustrated, the connector 750 is connected to the patient 964 via a catheter connected to the fluid port 878. The second end 758 of the housing passage 754 is attached to a container 966 of flush solution via a check valve 968 and an on/off clamp 970.

Typically, when blood samples are taken from a patient through an IV catheter using a system like the system 950, a "clearing sample" or "discard sample" will be taken first to prime the connector with undiluted blood. Despite the name, the discard sample may be reinfused into the patient after the "undiluted" samples are taken, although not necessarily. A plurality of undiluted samples will then be drawn through the connector. After drawing the required number of undiluted samples, the connector is flushed to remove residual blood from the connector and catheter. To facilitate use of the connector 750 for syringe-based blood sampling and discard reinfusion, the end 756 may include a pink or blue band as the "discard port," and the port 878 may include a red band as the "sample port."

To prepare to take a fluid sample (such as a blood sample or other bodily fluid sample) from the patient 964, the empty syringe 960 may be advanced into the first end 756 of the passage 754 to a position between that illustrated in FIGS. 13 and 14. During this transition as the syringe 960 is attached to the connector 750, fluid enters the chamber 820 from the passage 754 via the bypass 810. The connector 750 is now prepared for an automatic flush from chamber 820 once the syringe 960 is withdrawn in the direction of the first end 756.

The syringe 960 may be advanced until the second stationary seal 792 closes the open end 830 of the slider passage 832. The connection of the empty syringe 960 to the discard port 756 thereby provides an automatic flush (with the volume determined according to connector geometry) and positions the slider 762 to allow withdrawal of the discard or clearing sample. Once the syringe 960 is attached to the discard port 756, the plunger can be pulled back to withdraw and hold the desired clearing sample volume.

The Luer stem associated with the syringe 962 or connected to a vacutainer, for example, has thus far not been advanced into the first end 874 of the housing 850. When the Luer stem of the syringe 962 is advanced into the end 874, the slider 860 travels a sufficient distance such that the port 878 is in fluid communication with the first end 874 of the passage 872. The undiluted blood sample may now be drawn from the patient 964 into the syringe 962. It will be recognized that a connector according to this variant will be particularly well suited for serial collection of blood samples, using either multiple syringes or a vacuum-tube adapter. After the desired number of undiluted blood samples are drawn and the syringe 962 is removed from the end 874, the syringe 960 attached to end 756 may be depressed to reinfuse the discard sample, if desired. After removal of the syringe 960, the solution in chamber 820 flushes the connector 750 and the associated catheter using a volume determined according to the geometry of chamber 820.

As mentioned above, the connector 750 is not self priming; stated in other terms, the connector 750 has freeflow prevention. As a consequence, a further device must be used in conjunction with the connector 750 to prime the connector 750 before use. As illustrated in FIGS. 17 and 18, this additional device, which may be referred to as a priming cap 980, may be pre-attached to the end 756 of the connector 750 (and thus also provide a sterile cover for the end 756). The priming cap 980 includes a first, connection segment 982, which may be threaded (at 984) so as to cooperate with the threaded section (at 776) of the end 756 to join the priming cap 980 to the end 756. The priming cap 980 may also include a second, plunger segment 986 that comes in contact with the slider 762 so as to move the slider 762 along the passage 754. The plunger segment 986 is attached to the connection segment 982 by a flexible membrane 988, which deforms when the user depresses the plunger segment 986 (i.e., moves the plunger segment 986 in the direction of the port 756). In operation, the user would depress the plunger segment 986 of the priming cap 980 at least once to prime the connector 750 before connecting the port 878 to the patient's catheter. Alternatively, the user could use a (sterile) syringe to prime the connector 750, which would require swabbing or disinfection of the end 756 prior to priming.

As mentioned above, the challenges of clearing material from the needleless connector are not limited to T-site connectors. It is also possible to have unwanted material present in in-line connectors as well. Consequently FIGS. 19-27 illustrate a number of in-line connectors that "purge" the connector upon attachment of a Luer or other instrument and upon removal, or disconnect.

FIGS. 19-23 illustrate a connector 1000 including a housing 1002 defining a passage 1004 having a first open end 1006 and a second open end 1008. A flexible slider 1010 (which may be referred to as a boot) is disposed with the passage 1004 and is moveable relative to the housing 1002 along the passage 1004 in the direction of the first open end 1006 and in the direction of the second open end 1008. Also disposed in the passage 1004 is a resilient member 1012 (which may also be referred to as a boot), the resilient member 1012 being disposed between the slider 1010 and the housing 1002. The resilient member 1012 does not move relative to the housing 1002 as much as it is compressed between the slider 1010 and the housing 1002.

The housing 1002 is formed of two pieces: the cap 1020 and the base 1022. The cap 1020 includes a first, stepped passage 1024 that defines a distal section of the passage 1004. A section 1026 of the cap 1020 may have threads 1028 formed therein, permitting use of the section 1026 as a female Luer. The base 1022 also includes a passage 1030 that defines a proximal section of the passage 1004. In particular, the passage 1030 may be defined by a tubular section 1032 of the base 1022. A distal surface 1034 of the base 1022 may be joined to a proximal surface 1036 of the cap 1020 through the use of ultrasonic welding, for example, to attach the two sections 1020, 1022 of the housing 1002 together.

The slider 1010 has first and second opposing ends 1040, 1042 and a side 1044 between the first and second ends 1040, 1042. As will be recognized, the side 1044 of the slider 1010 defines a surface 1046 that cooperates with an internal surface 1048 of the cap 1020 to seal the first end 1006 of the passage 1004 in the first state illustrated in FIG. 1.

The slider 1010 has a slider passage 1050 with a first and second open ends 1052, 1054. The first end 1052 of the slider passage 1050 is disposed along the side 1044 of the slider 1010. The second end 1054 of the slider passage 1050 is disposed at the second end 1042 of the slider 1010.

It will be recognized that the slider passage 1050 may have a number of open first ends 1052. For example, other embodiments of the slider 1010 may include two, three or more openings 1052 in the side 1044 of the slider 1010.

The first end 1052 of the slider passage 1050 is associated with a first section 1060 of the slider passage 1050, while the second end 1054 is associated with a second section 1062 of the slider passage 1050. While the first and second sections 1060, 1062 of the passage 1050 are illustrated at right angles to each other, this orientation need not be same in all embodiments.

The slider 1010 also includes a number of pinch valves 1070. These pinch valves 1070 are defined by passages that are disposed along a proximal surface 1072 of the slider 1010 as the second end 1042 (see FIG. 20). The passages 1070 are designed to collapse upon application of axial force to the first end 1040 of the slider 1010. While three pinch valves 1070 are shown, the number of pinch valves 1070 is not intended to be limited thereby.

The slider 1010 also includes three bypass passages or channels 1080. The bypasses 1080 are formed in the side 1044 of the slider 1010. Again, while three bypasses 1080 are illustrated, this is an exemplary number and not intended to limit the disclosure thereby.

Turning next to the resilient member 1012, the resilient member 1012 has a conical proximal section 1090 and an annular distal section 1092. The resilient member 1012 includes a passage 1094 defined through the sections 1090, 1092 in fluid communication with the slider passage 1050 and the passage 1030 in the base 1022. The resilient member 1012 elastically deforms between the state illustrated in FIG. 19 and the state illustrated in FIG. 23, and thus provides a biasing force to restore the slider 1010 to the position illustrated in FIG. 19 from that illustrated in FIG. 23.

The section 1092 cooperates with (e.g, abuts) an inner surface 1100 of the housing 1002, and in particular the cap 1020, to provide a fluid-tight seal therebetween; it will be recognized that the roles could be reversed wherein the slider 1010 is rigid and the cap (or a seal attached thereto) is flexible instead with a similar seal being formed. Moreover, there is a chamber (or reservoir) 1102 defined by the housing 1002, the slider 1010 and the distal section 1092, which may also be referred to as a movable or wiper seal. As the slider 1010 moves in the direction of the end 1008, the chamber 1102 expands, and when the slider 1010 moves in the direction of the end 1006, the chamber 1102 contracts (compare FIGS. 19 and 23, for example).

In fact, it will also be recognized that the distal section 1092 of the resilient member 1012 may be formed separately from the proximal section 1090, and mounted on the side 1044, for example, of the slider 1010. The operation of the connector 1000 would remain the same, and the proximal section 1090 of the member 1012 may be referred to still as the "resilient member." The distal section 1092 may in turn be referred to, as indicated above, as the moveable seal.

Figure 19:
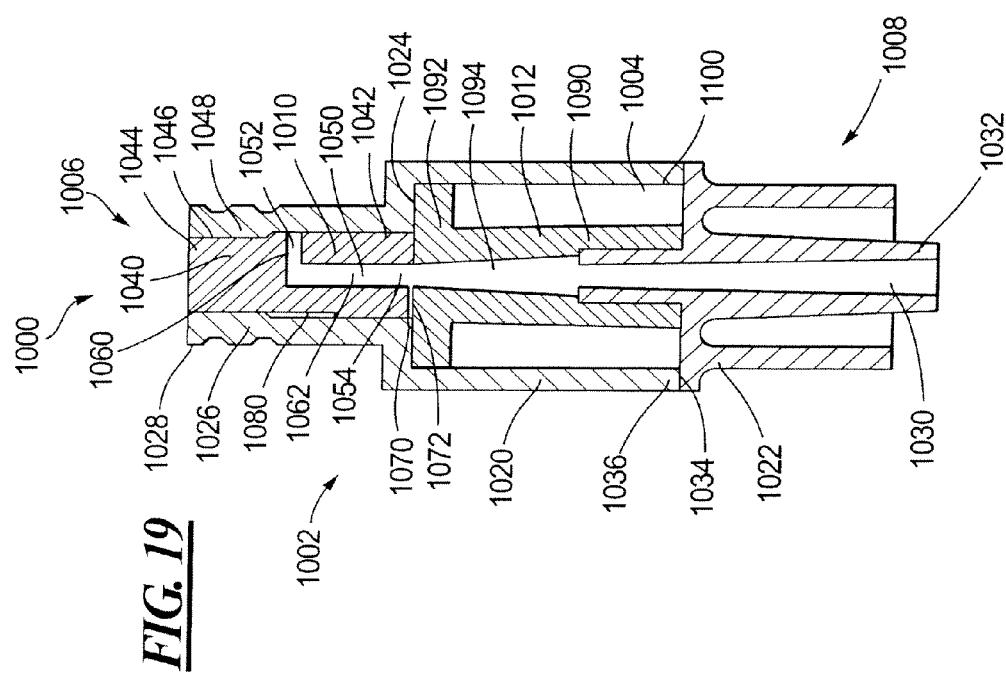
FIG. 19 is a cross-sectional view of a straight in-line connector in a first state.

In operation, force applied in the axial direction by contact between a male Luer and the first end 1040 of the slider 1010 causes the pinch valves 1070 to collapse (compare FIGS. 19 and 21). It will be recognized that the collapse and closure of the pinch valves 1070 will require the slider 1010 to have a modulus selected to deform to close the pinch valves 1070 before the slider 1010 begins to move.

As the slider 1010 continues to move in the direction of the end 1008 of the passage 1004, as illustrated in FIG. 22, a vacuum is created in the chamber 1102. The slider passage 1050 is sealed through the cooperation of the slider 1010 and the inner surface 1100 of the passage 1004, and the pinch valves 1070 which were closed upon initial application of force to the slider 1010. As a consequence, the movement of the slider 1010 in the direction of the end 1008 causes any fluid in the slider passage 1050 or the member passage 1094 to be discharged from the connector 1000.

Further movement of the slider 1010 results in the state illustrated in FIG. 22. In this state, the bypasses 1080 permit fluid communication between the chamber 1102 and the first end 1006 of the passage 1004. Fluid may be drawn from the male Luer into the chamber 1102 at this time. Still further movement of the slider as illustrated in FIG. 23 results in the open end 1052 of the slider passage 1050 being in fluid communication with the chamber 1102 as well. This movement may permit the fluid already drawn into the chamber 1102 from the male Luer to exit the through the slider passage 1050.

Fluid from the male Luer may now be infused via the path including the space between the first end 1040 of the slider 1010 and the housing 1002, the bypasses 1080, the chamber 1102, the open end 1052, the slider passage 1050 and the member passage 1094. Alternatively, aspiration of fluids may be made along the reverse path.

When the male Luer is removed, the slider 1010 moves back along the passage 1004 between the state illustrated in FIG. 23 and that illustrated in FIG. 19. However, as soon as the axial force is relieved from the slider 1010, the pinch valves 1070 are restored to the as-molded "open" position. That is, the slider 1010 may return from its previous deformation without any significant movement of the slider 1010 along the passage 1004, allowing fluid to exit the chamber 1102. As a practical matter, the opening of the valves 1070 may cause a slight siphoning into the chamber 1102, but this volume should be significantly less than the amount exiting through the valves 1070, the open end 1052 (for a limited male Luer return distance) and the slider passage 1050 as the slider 1010 travels in the direction of the end 1006 of the passage 1004.

Further movement of the slider 1010 will cause the closure of open end 1052 of the slider passage 1050, with all of the fluid from the chamber 1102 then being discharged from through the valves 1070. It may be possible for fluid to also discharge through the bypasses 1080 to the male Luer. However, the design of the bypasses 1080 may increase the flow resistance through the bypasses 1080 to the male Luer to such an extent that for practical purposes most of the flow is through the valves 1070. Stated another way, the flow resistance of the pinch valves 1070 should be relatively less than the flow resistance of the bypasses 1080 to reverse flow. In any event, when the slider 1010 moves to the state illustrated in FIG. 19, the cooperation of the slider 1010 and the inner surface 1100 limits further reverse flow to the male Luer.

It will be recognized that while the slider 1010 and the resilient member 1012 are illustrated as separate structures, the two structures 1010, 1012 may be formed integrally with each other (i.e., as one piece). In such a case, the pinch valves 1070 may be replaced with check valves formed, for example, from a slit in the wall of the single structure or a thin lumen tube. Even in such an embodiment, however, the distal section of the single structure may be referred to as the slider and the proximal section as the resilient member.

The combination of pinch valves 1070, bypasses 1080, slider 1010, and resilient member 1012 described above result in a connector 1000 which provides displacement of fluid (or flush solution) during both male Luer connection and withdrawal. This configuration is intended to address the "attachment reflux" observed with conventional positive displacement LAD's, which positively displace fluid during male Luer withdrawal, but reflux during male Luer connection. Chamber 1102 draws fluid from the flush syringe during connection, which is ejected during disconnection.

It will be further recognized that the pinch valves 1070 illustrated in the embodiment of FIGS. 19-23 are but one possible arrangement for opening and closing the particular flow path defined thereby. The connectors illustrated in FIGS. 24-27 illustrate alternatives to the pinch valves. The embodiment in FIGS. 24-25 utilizes a rigid cannula, while the embodiment in FIGS. 26-27 utilizes a flapper valve. As done elsewhere, we will focus primarily on the differences between the embodiments, rather than discussing the structures shared in common.

Figure 24:
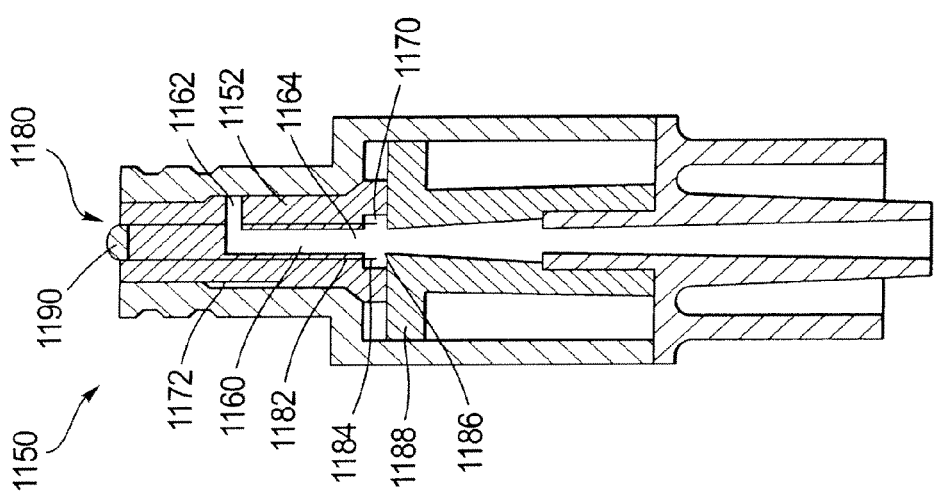
FIG. 24 is a cross-sectional view of another in-line connector in a first state.
Figure 25:
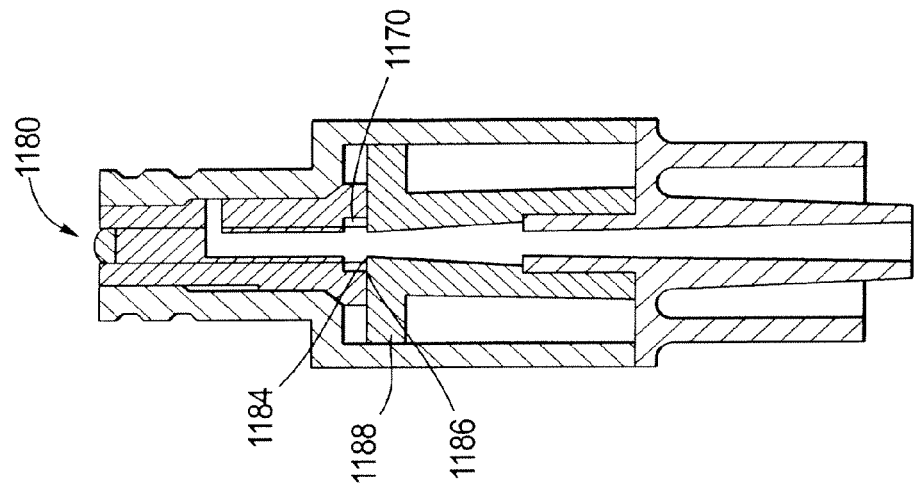
FIG. 25 is a cross-sectional view of the in-line connector of FIG. 24 in a second state.

Turning then first to the connector 1150 illustrated in FIGS. 24-25, the connector 1150 includes a slider 1152. Similar to the slider 1010, the slider 1152 includes a slider passage 1160 having a first end 1162 and a second end 1164, one or more passages 1170 and one or more bypasses 1172. However, unlike the embodiment of FIGS. 19-23, the passages 1170 do not collapse to prevent the passage of fluid through the passages 1170.

Instead, a rigid cannula 1180 passes through the slider 1152, which cannula 1180 is moveable relative to the slider 1152. The cannula 1180 has a wall 1182 with an edge 1184. The edge 1184 is spaced from a distal surface 1186 of a resilient member 1188 in a first state, illustrated in FIG. 24, to permit fluid flow through the passages 1170. The edge 1184 abuts the distal surface 1186 of the resilient member 1188 in a second state, illustrated in FIG. 25 to limit fluid flow through the passages 1170. To facilitate movement of the cannula 1180 in response to axial force applied by a male Luer, the cannula 1180 may be include a solid button 1190 that may cooperate with the male Luer to transmit the axial force to the cannula 1180 to move it relative to the slider 1152.

Figure 26:
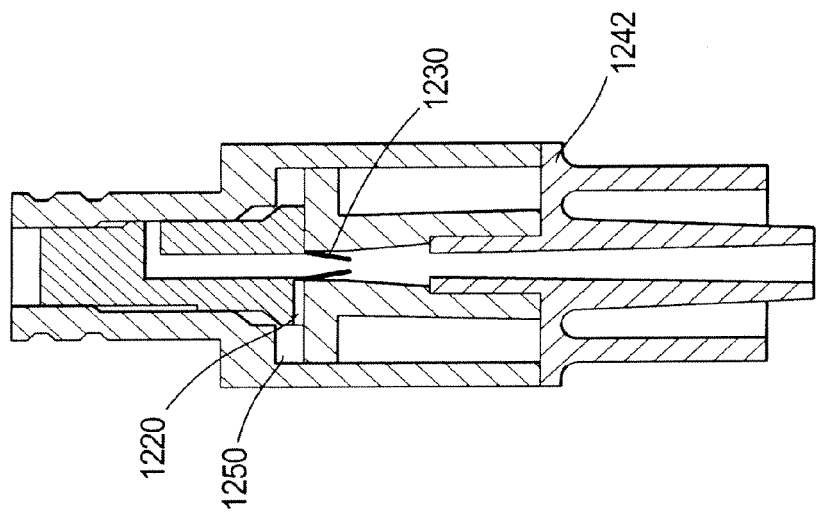
FIG. 26 is a cross-sectional view of a further in-line connector in a first state.
Figure 27:
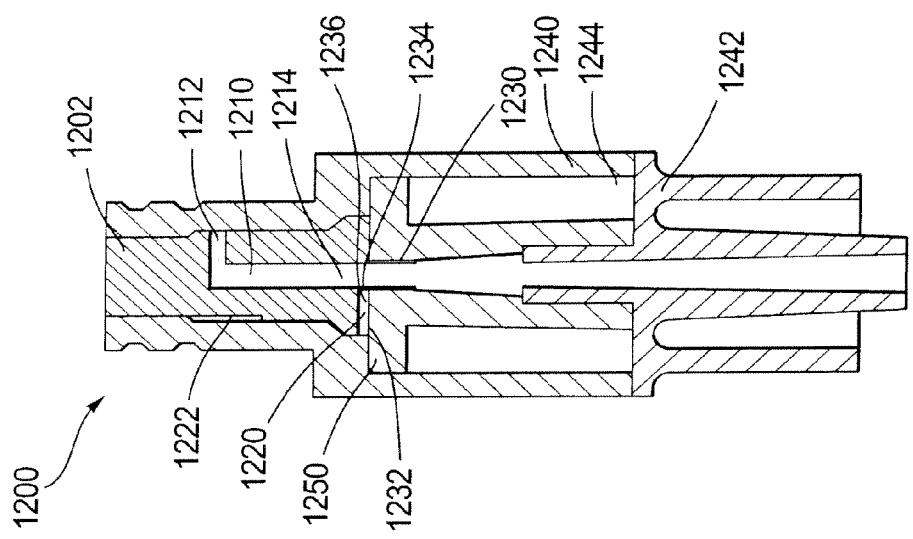
FIG. 27 is a cross-sectional view of the in-line connector of FIG. 26 in a second state.

Turning now to FIGS. 26-27, a connector 1200 is illustrated, the connector 1200 including a slider 1202. Similar to the slider 1010, the slider 1202 includes a slider passage 1210 having a first end 1212 and a second end 1214, one or more passages 1220 and one or more bypasses 1222. However, unlike the embodiment of FIGS. 19-23, the passages 1220 do not collapse to prevent the passage of fluid through the passages 1220.

Instead, the slider 1202 has a tubular extension 1230 that depends from a proximal surface 1232 of the slider 1202. The tubular extension 1230 includes a wall 1234 that occludes an end 1236 of the passages 1220 initially, and throughout the motion of the slider 1202 relative to a housing 1240 of the connector 1200 in the direction of an end 1242 of a housing passage 1244. However, when the motion of the slider 1202 is reversed, the pressure on the fluid retained above a moveable seal 1250 is such that the tubular extension 1230 is deformed inwardly, thereby permitting fluid to flow in the direction of the end 1242 (See FIG. 27).

It will be recognized that the connectors illustrated in the foregoing examples include either a vacuum chamber and/or a compression spring to bias the slider toward one end of the housing passage. However, it may also be possible to provide a tension spring attached to the slider as an alternative for biasing the slider and at the same time eliminating the need for the moveable or wiper seal present in a number of the connectors above. The connectors illustrated in FIGS. 28-35 include such tension springs.

Referring first to FIGS. 28 and 29, an embodiment of a connector 1300 for use with a T-site connector is illustrated. The connector 1300 includes a housing 1302 having a housing passage 1304 with first and second open ends 1306, 1308 and a side port 1310. A slider 1312 is disposed in the passage 1304 and moveable between the first and second ends 1306, 1308 of the housing passage 1304.

As will be noted, the housing 1302 is formed of at least two pieces: the cap 1320 and the body 1322. The cap 1320 includes a first passage 1324 that defines a distal section of the passage 1304. The first passage 1324 is partially defined in a tubular extension 1326 of the cap 1320 that has threads 1328 formed therein, permitting use of the extension 1326 as a female Luer. The generally cylindrical body 1322 includes a passage 1330 that defines a proximal section of the passage 1304. A distal end 1332 of the body 1322 is joined to a proximal end 1334 of the cap 1320 through the use of ultrasonic welding, for example, to attach the two sections 1320, 1322 of the housing 1302 together.

A stationary seal 1340 is disposed between the first end 1306 of the housing passage 1304 and the side port 1310. In particular, the first stationary seal 1340 may be overmolded to the tubular extension 1326 of the cap 1320. The seal 1340 provides a compression seal against the slider 1312. The seal 1340 also provides a compression seal against the outer surface of a male Luer disposed into the first end 1306 of the housing passage 1304; preferably, the seal 1340 is sized to provide a compression seal against the male Luer during the entire movement of male Luer into and out of the end 1306 of the passage 1304.

An elastomeric tension spring 1350 is partially disposed between the cap 1320 and the body 1322 and is attached to the slider 1312. The tension spring 1350 may be formed as a separate piece or overmolded to the slider 1312 or the body 1322. During fastening of the cap 1320 to the body 1322, the desired pre-load or tension can be supplied to the tension spring 1350. The tension spring 1350 is annular in shape, and has an outer edge 1352 and an inner edge 1354 disposed about a central passage 1356. The outer edge 1352 is disposed between opposing surfaces 1358, 1360 of the cap 1320 and the body 1322 to hold the outer edge 1352 fixed relative to the housing 1302.

In operation, the slider 1312 is moved in the direction of the end 1308 of the passage 1304 (compare FIGS. 28 and 29). As the slider 1312 moves, the spring 1350 stretches and is drawn through the passage 1330 in the body 1322. Given the point of attachment between the cap and body 1320, 1322 and the overmolding with the slider 1312, the spring 1350 also acts as a fluid-tight seal. As such, the single structure 1350 replaces the moveable seal and spring in the embodiments above, such as are shown in FIGS. 1-3, with a further consequence that the seal 1350 does not have a tendency to draw fluid down into the passage below the slider 1312 during the travel of the slider 1312.

FIGS. 30-35 illustrate in-line connectors incorporating tension springs. Turning first to the connector 1400 in FIGS. 30 and 31, the connector 1400 includes a housing 1402 having a housing passage 1404 with first and second open ends 1406, 1408. A slider 1412 is disposed in the passage 1404 and moveable between the first and second ends 1406, 1408 of the housing passage 1404.

As will be noted, the housing 1402 is formed of at least two pieces: the cap 1420 and the body 1422. The cap 1420 includes a first passage 1424 that defines a distal section of the passage 1404. The generally cylindrical body 1422 includes a passage 1426 that defines a proximal section of the passage 1304. A tubular extension 1428 at the proximal end 1430 of the cap 1420 is received in an annular recess 1432 at the distal end 1434 of the body 1422. An outer rim 1436 of the proximal end 1430 of the cap 1420 is joined through the use of ultrasonic welding, for example, to an outer rim 1438 of the distal end 1434 of the body 1422 to attach the two sections 1420, 1422 of the housing 1402 together.

A stationary seal 1440 is disposed at the first end 1406 of the housing passage 1404. In particular, the first stationary seal 1440 may be overmolded on the cap 1420. The seal 1440 provides a compression seal against the slider 1412.

An elastomeric tension spring 1450 (which may be referred to as a resilient member) is partially disposed between the cap 1420 and the body 1422 and is attached to the slider 1412. In particular, the tension spring 1450 is cup-shaped, with an U-shaped outer section 1452 and an annular inner second 1454. The outer edge 1452 is disposed between the tubular extension 1428 of the cap 1420 and the recess 1432 of the body 1422 to hold the outer edge 1452 fixed relative to the housing 1402. The inner edge 1454 is overmolded on the slider 1412, the slider 1412 having a groove 1456 formed therein to receive the inner edge 1454 of the spring 1450.

Figure 31:
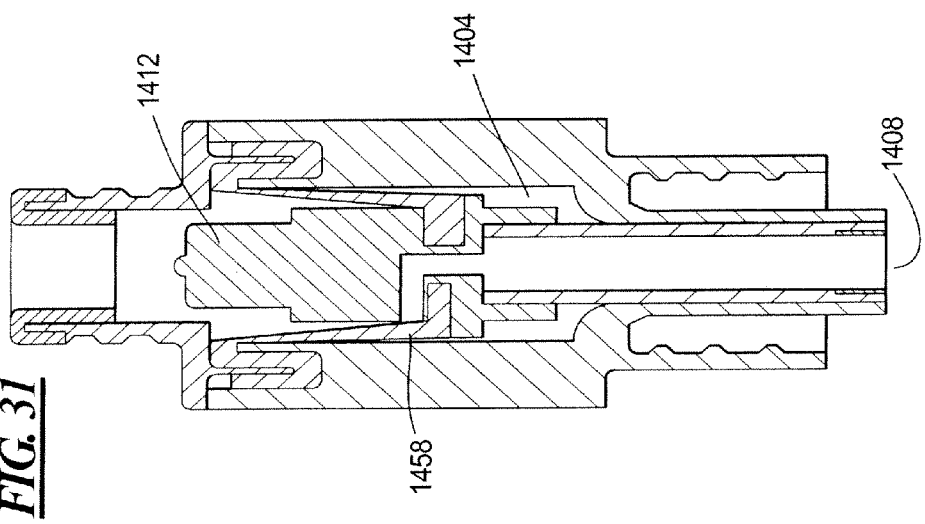
FIG. 31 is a cross-sectional view of the connector of FIG. 30 in a second state.
Figure 30:
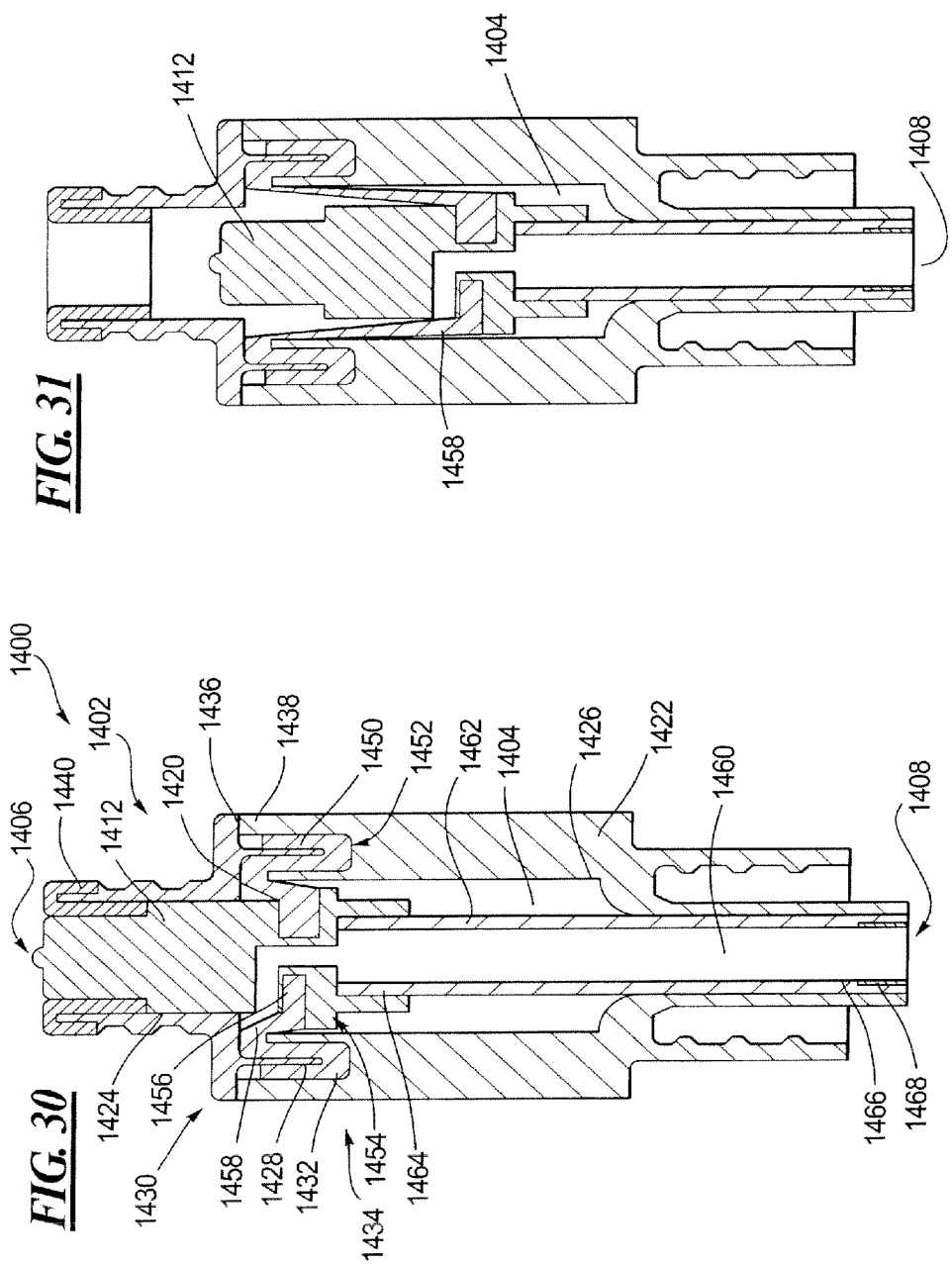
FIG. 30 is a cross-sectional view of a straight in-line connector with a tension spring in a first state.

The spring 1450 also includes an intermediate section 1458. The intermediate section 1458 connects the outer and inner sections 1452, 1454, and depends in the direction of the proximal end 1404. As illustrated in FIGS. 30 and 31, the stretching of the spring 1450 occurs mainly in the intermediate section 1458. As the slider 1412 advances in the direction of the end 1408 of the passage 1404, the intermediate section 1458 may decrease in thickness, as seen in FIG. 31.

To ensure that the fluid communication is maintained between a slider passage 1460 of the slider 1412 and the second end 1408 of the housing 1402, a tube 1462 is provided. The tube 1462 may be made of an elastomeric material having a first end 1464 attached to the slider 1412 and a second end 1466 attached to the housing 1402. Specifically, a bushing 1468 may be disposed within the second end 1466 of the tube 1462 to maintain the second end 1466 of the tube 1462 in the second end 1408 of the passage 1404. Alternatively, the tube may be overmolded to the slider 1412 as part of the spring 1450.

Figure 32:
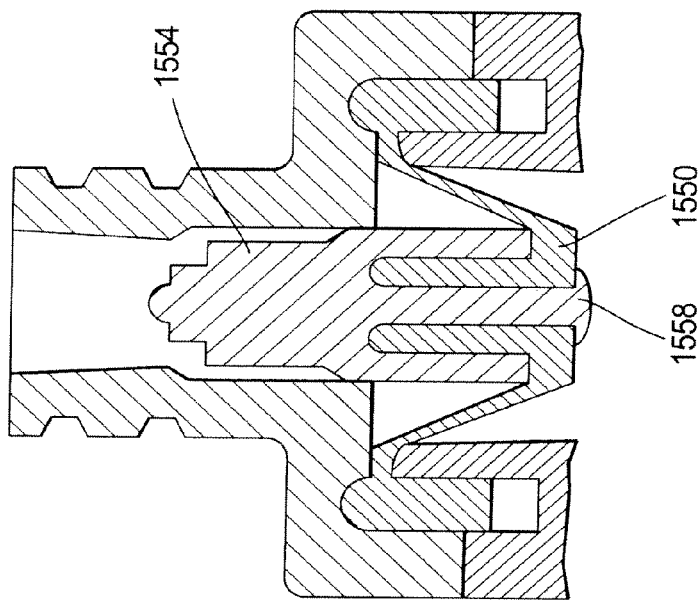
FIG. 32 is a cross-sectional view of a straight in-line connector with a tension spring in a first state.
Figure 33:
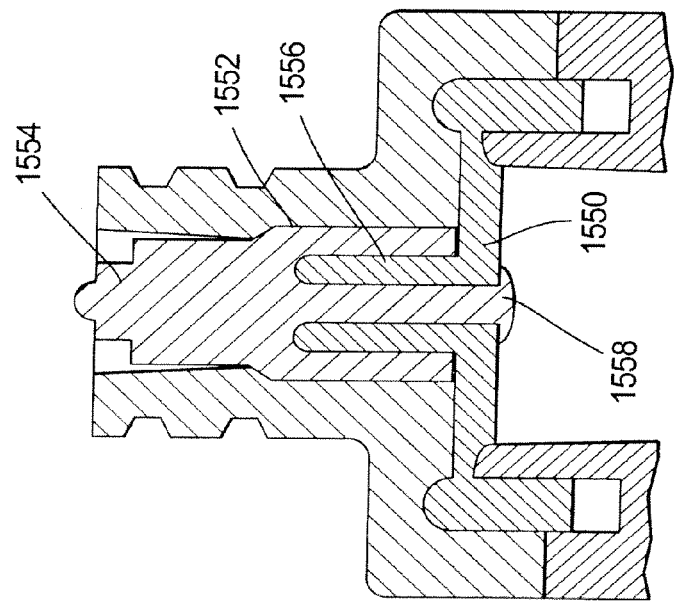
FIG. 33 is a cross-sectional view of the connector of FIG. 32 in a second state.

A further variant of a tension spring 1550 is illustrated in FIGS. 32 and 33. Unlike the variant in FIGS. 30 and 31, the tension spring 1550 is overmolded to an end 1552 of a slider 1554. To facilitate the overmolding of the tension spring 1550 to the slider 1554, the slider 1554 has an annular recess 1556. Additionally, a boss or button 1558 is formed such that the tension spring 1550 extends behind the button 1558 to further secure the spring 1550 to the slider 1554.

Figure 35:
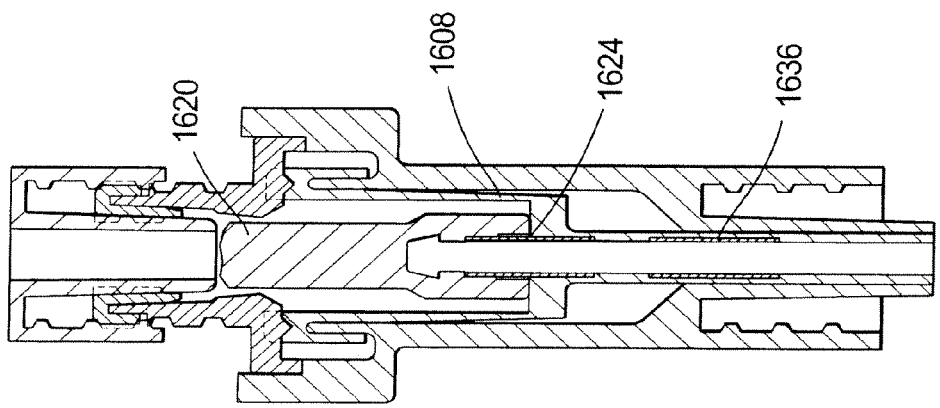
FIG. 35 is a cross-sectional view of the connector of FIG. 34 in a second state.
Figure 34:
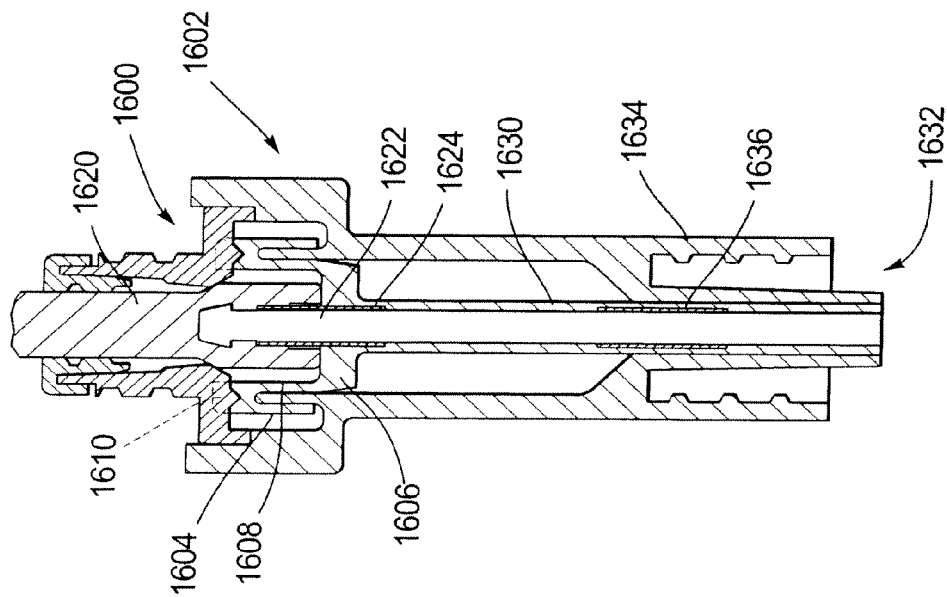
FIG. 34 is a cross-sectional view of a straight in-line connector with a tension spring in a first state.

A variant of the tension spring 1600 illustrated in FIGS. 32 and 33 is illustrated in FIGS. 34 and 35. According to this embodiment, the tension spring 1600 is similar to the tension spring 1550 in that the tension spring 1600 is cup-shaped at a distal end 1602 thereof. The distal end 1602 of the tension spring 1600 includes a U-shaped outer section 1604, an annular inner section 1606 and an intermediate section 1608 that connects the outer section 1604 to the inner section 1606. As illustrated, the intermediate section 1608 joins the outer section 1604 and the inner section 1608 at approximately right angles at shoulders 1610, 1612. As such, the intermediate section 1508 is tubular in shape.

Unlike the tension spring 1550, the inner section 1606 is not overmolded to slider 1620. Instead, the inner section 1606 is attached to the slider 1620 through the use of a bushing 1622, the bushing 1622 depending into the slider 1620 and a passage 1624 formed through the inner section 1606. Also unlike the tension spring 1550, the tension spring 1600 is formed integrally (i.e., as one piece) with the elastomeric tube 1630 that connects the passage 1624 and an open end 1632 of housing 1634. Similar to the inner section 1606, the tube 1630 is attached to the open end 1632 of the housing 1634 using a bushing 1636.

Taking the idea of a tension spring a step further, an additional set of embodiments are illustrated in FIGS. 36-40. This set of variants has certain similarities with the tension springs just discussed. The structure that defines the spring is formed integrally with a tube used to define the flow path through the connectors. Further, similar to the later tension spring variants above, the slider is disposed at least partially within the structure that performs the biasing of the slider. However, this further set of variants, which may be referred to as the "tube sock variants," also has several points of distinction as well.

Referring then first to the connector 1650 of FIG. 36, the connector 1650 includes a housing 1652 having a housing passage 1654 with first and second open ends 1656, 1658. A slider 1660 is disposed in the passage 1654 and moveable between the first and second ends 1656, 1658 of the housing passage 1654.

As will be noted, the housing 1652 is formed of at least two pieces: the cap 1670 and the base 1672. The cap 1670 includes a first passage 1674 that defines a distal section of the passage 1654. The first passage 1674 is partially defined in a tubular extension 1676 of the cap 1670 that has threads 1678 formed therein, permitting use of the extension 1676 as a female Luer. The generally cylindrical base 1672 includes a passage 1680 that defines a proximal section of the passage 1654. A distal end 1682 of the base 1672 is joined to a proximal end 1684 of the cap 1670 through the use of opposing surfaces 1686, 1688. In particular, the cap 1670 has an retainer 1690 having a leg 1692 with a hook 1694 formed at one end 1696, the hook 1694 defining the surface 1686, and the base 1672 has a shoulder 1698 that defines the surface 1688. In the alternative, the cap 1670 and the base 1672 may be joined through the use of ultrasonic welding, for example.

According to this variant, the structure that biases the slider 1660 toward the first end 1656 of the passage 1654 also replaces a stationary or moveable seal as illustrated above and includes a tube that defines the flow path through the passage 1654. However, the structure also is formed integrally (i.e., as one piece) with the stationary seal disposed at the first end 1656 to limit fluid flow from the connector 1650 in the state illustrated in FIG. 36. The structure 1700 (which may be referred to as a "tube sock") thus has a distal sealing section 1702, an intermediate resilient biasing section 1704 and a proximal tubular section 1706. Herein, the separate sections 1702, 1704, 1706 may be referred to as the seal, resilient member, and tube respectively.

Starting then with the seal 1702, the seal 1702 may be overmolded on the cap 1670. The seal 1702 may have an inwardly-depending, annular flange (or lobe) 1710 that abuts with an outwardly depending structure 1712 formed on a side 1714 of the slider 1660 at a first, distal end 1716 of the slider 1660. The structure 1712 may be referred to as a plurality of tabs, and according to at least one embodiment may include four tabs disposed with a uniform (or equal) spacing between the tabs. The lobe 1710 and the tabs 1712 have opposing surfaces 1718, 1720 that cooperate with each other to limit the movement of the slider 1660 in the direction of the end 1656 of the passage 1654. Surfaces 1722, 1724 of the seal 1702 and slider 1660 also cooperate to form a fluid-tight compression seal to limit passage of fluids through the first end 1656 of the passage 1654 in the embodiment illustrated FIG. 36.

The slider 1660 may also include axial ribs disposed along the side 1714 to accommodate "neck-down" of tube-sock surface 1704 during male Luer connection. Without axial ribs 1714, neck-down of tube-sock surface 1704 may result in fluid reflux upon male Luer withdrawal because of the change in volume in the space around the slider 1660. Axial ribs disposed on surface 1714 limit the volume change so as to preserve neutral to positive displacement upon male Luer withdrawal.

The resilient member 1704 is formed integrally with the seal 1702, as mentioned above. The resilient member 1704 has a shoulder 1730 that cooperates with a proximal second end 1732 of the slider 1660. The cooperation between the shoulder 1730 and the end 1732 of the slider 1660, along with the stretching of the resilient member 1706, biases the slider 1660 in the direction of the first end 1656 of the passage 1654.

The tube 1708 is, in turn, formed integrally with the resilient member 1706. The tube 1708, similar to the tubes in the variants according to the immediately preceding set of tension springs, ensures a controlled flow path between the first and second ends 1656, 1658 of the passage 1654. The tube 1708 has an end 1740 that is joined to the base 1672 through the use of a bushing 1742 disposed within the tube 1708 at the second end 1658 of the passage 1654.

The tube 1708 is fastened to the second end 1658 of the passage 1654 in a state of tension so that when the male Luer is connected, the tube 1708 will not collapse or kink. The state of tension must therefore be on the order of or greater than the axial displacement caused by the insertion of the male Luer. It will be recognized that by placing the tube 1708 into a state of tension reduces the initial wall thickness of the tube 1708 by the neck-down mechanism described by Poisson's ratio. When the male Luer is connected, the wall thickness of the tube 1708 returns to a value closer to the as-formed or original state, and the internal volume may increase. Upon male Luer withdrawal, the tube 1708 stretches and necks down, reducing the internal volume and contributing to positive displacement.

A brief digression is taken with reference to FIGS. 37 and 38 to discuss a variation of the slider, which variation is taken not only relative to FIG. 36, but also with the sliders reference even in FIGS. 1-3, above. It will be noted in the embodiment of FIG. 36, the end 1716 of the slider 1660 has an irregular profile in cross-section, the profile being formed to prevent the opening of the male Luer used with the slider 1660 from being sealed by the surface 1750. However, it will be recognized that an irregular profile may present certain challenges relative to the swabability of the surface 1750, which procedure is commonly used to remove microbes from the surface 1750.

The embodiment of FIGS. 37 and 38 illustrated a slider 1770 having a surface 1772 with a sloped profile 1774. In particular, the sloped profile 1774 has a first flat section 1776, an intermediate sloped section 1778, and a second flat section 1780. It is believed that a sloped profile 1774 will permit engagement of the slider 1770 by the male Luer, while at the same time limiting the possibility that the surface 1772 of the slider 1770 will significantly occlude or completely block the opening of the male Luer.

Figure 39:
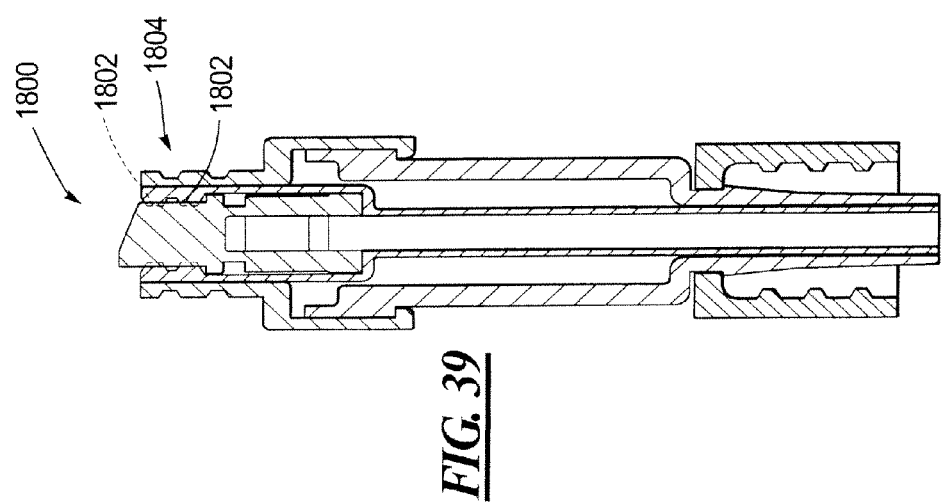
FIG. 39 is a cross-sectional view of a straight in-line connector with an integrated seal/biasing element/tube in a first state.

Turning now to FIG. 39, a variant is illustrated with reference to the connector 1650 above. A connector 1800 is provided, principally to illustrate that it is not necessary to have a single lobe to define the seal at the first end of the housing passage. Instead, the connector 1800 has two lobes 1802 that define the seal 1804. Consequently, it will be recognized that the number of lobes 1802 is not limited to the embodiments illustrated herein.

Figure 40:
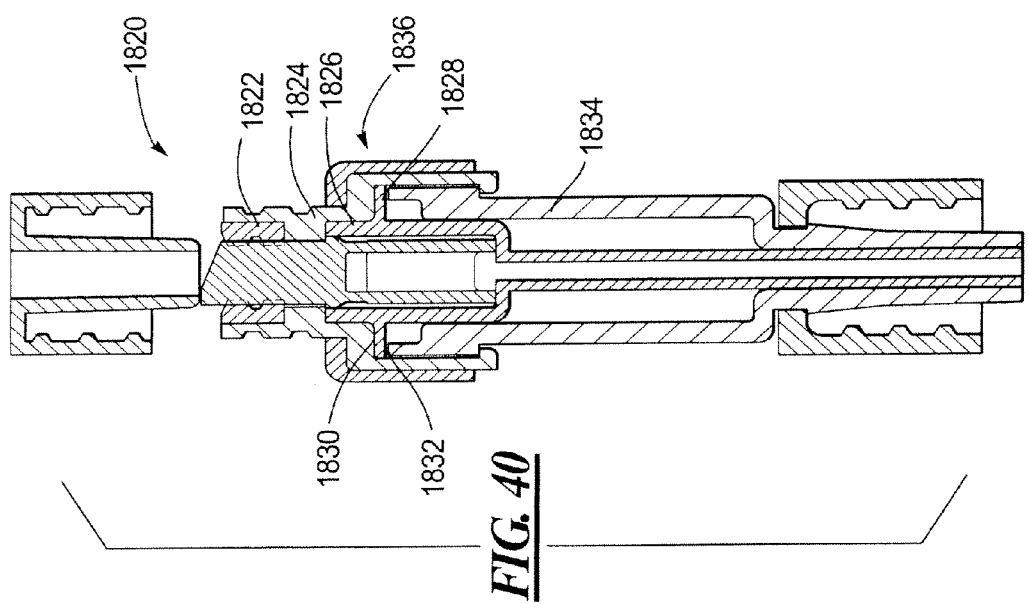
FIG. 40 is a cross-sectional view of a straight in-line connector with an integrated seal/biasing element/tube in a first state.

As a further variant, a connector 1820 is illustrated in FIG. 40. In particular, the connector 1820 illustrates that a seal 1822 may be overmolded separately to a cap 1824 than a resilient member 1826, while remaining within the scope of the present disclosure. Moreover, the overmolding of the resilient member 1826 may include a flange 1828 that is disposed between opposing surfaces 1830, 1832 of the cap 1824 and a base 1834. With the cap 1824 secured to the base 1834, the flange 1828 is trapped therebetween, which may improve the stability of the resilient member 1826 at a first end 1836.

A further set of variants is illustrated in FIGS. 41-49. These variants draw on different concepts from the preceding discussion, while adding further features.

With reference to FIGS. 41-43, a connector 1900 is illustrated therein. The connector 1900 includes a housing 1902 having a housing passage 1904 with first and second open ends 1906, 1908. A slider 1910 is disposed in the passage 1904 and moveable between the first and second ends 1906, 1908 of the housing passage 1904.

As will be noted, the housing 1902 is formed of at least two pieces: the cap 1920 and the body 1922. The cap 1920 includes a first passage 1924 that defines a distal section of the passage 1904. The first passage 1924 is defined in a tubular extension 1926 of the cap 1920 that has threads 1928 formed therein, permitting use of the extension 1926 as a female Luer. The generally cylindrical body 1922 includes a passage 1930 that defines a proximal section of the passage 1904. A distal end 1932 of the body 1922 is joined to a proximal end 1934 of the cap 1920 through the use of ultrasonic welding, for example, to attach the two sections 1920, 1922 of the housing 1902 together.

Overmolded on the cap 1920 is a seal 1940 and a tension spring 1942, the seal 1940 and the spring 1942 being formed integrally (i.e., as one piece). The tension spring 1942 includes a tubular extension that depends into the passage 1930 of the body 1922. The tension spring 1942 is joined to the slider 1910 through the use of a ring seal, for example. The tension spring 1942 biases the slider toward the first end 1906 of the passage 1904 and replaces the moveable seal illustrated in certain of the embodiments discussed above.

Also disposed within the passage 1930 is a compression spring 1950. In addition to assisting in biasing the slider 1910 in the direction of the first end 1906 of the passage 1904, the compression spring 1950 may limit the aerosol effect present in certain needleless connectors during disconnection. Thus, the compression spring 1950 may have a distal open end 1952 about which is an inwardly depending rim 1954 that defines a first seal and a proximal closed end 1956 with a preslit septum 1958. The slider 1910 has an extension 1960 with at least one aperture 1962 that is received in the compression spring 1950 in a region 1964 between the rim 1954 and the septum 1958.

As the slider 1910 is advanced in the direction of the second end 1908 of the passage 1904, the aperture 1962 moves within the spring 1950. Well after the male Luer becomes engaged by the seal 1940, the extension 1960 penetrates the septum 1958, exposing the aperture 1962. As the male Luer is removed, the extension 1960 is withdrawn into the sealed region between the rim 1954 and the septum 1958, thus placing the aperture 1962 in the region 1964. During male Luer withdrawal, negative pressure will be generated in chamber 1964, which is intended to prevent aerosolization of fluid (caused by positive pressure) during male Luer disconnection. Due to the negative pressure generated, the intended effect is the opposite of aerosolization: the male Luer will draw in ambient fluid as it clears seal 1940.

A different approach to the use of the slider is illustrated in the variants of FIGS. 44-51. Unlike the previous variants, wherein the slider was exposed to the environment before Luer insertion and after Luer disconnection, the slider is not exposed to the environment at any time. Instead, all of the variants of FIGS. 44-51 utilize a slit septum through which the Luer (or other instrument) is inserted before coming in contact with the slider.

Figure 44:
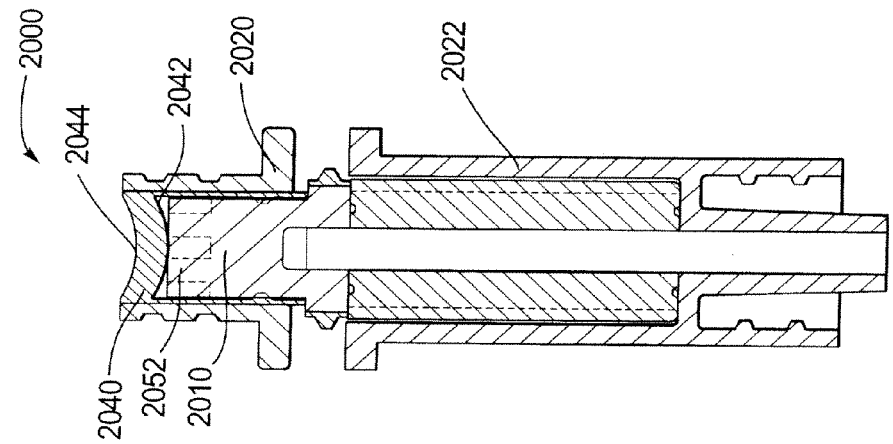
FIG. 44 is a cross-sectional view of a straight in-line connector with a slit septum and compression spring in an assembled state.
Figure 45:
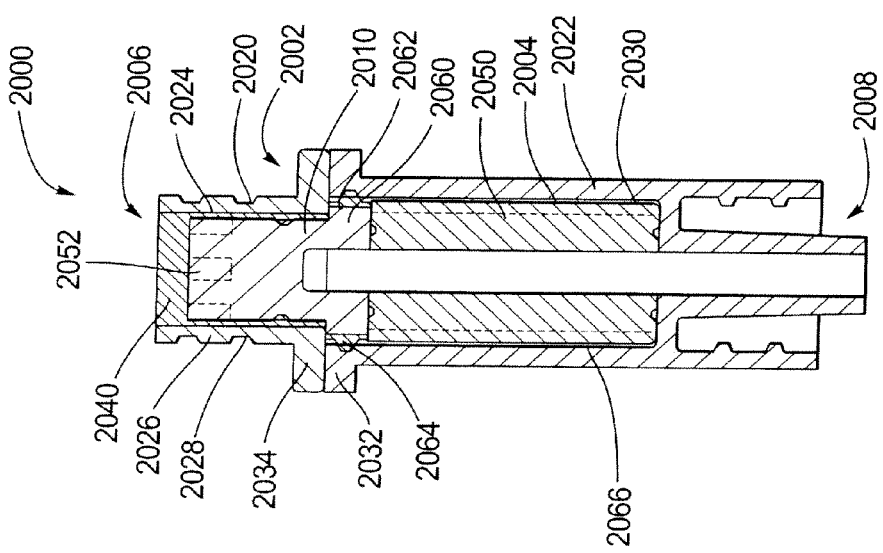
FIG. 45 is a cross-sectional view of the connector of FIG. 44 in an pre-assembled state.

The first variant is illustrated in FIGS. 44-45. A connector 2000 is illustrated therein. The connector 2000 includes a housing 2002 having a housing passage 2004 with first and second open ends 2006, 2008. A slider 2010 is disposed in the passage 2004 and moveable between the first and second ends 2006, 2008 of the housing passage 2004.

As will be noted, the housing 2002 is formed of at least two pieces: the cap 2020 and the body 2022. The cap 2020 includes a first passage 2024 that defines a distal section of the passage 2004. The first passage 2024 is defined in a tubular extension 2026 of the cap 2020 that has threads 2028 formed therein, permitting use of the extension 2026 as a female Luer. The generally cylindrical body 2022 includes a passage 2030 that defines a proximal section of the passage 2004. A distal end 2032 of the body 2022 is joined to a proximal end 2034 of the cap 2020 through the use of ultrasonic welding, for example, to attach the two sections 2020, 2022 of the housing 2002 together.

Overmolded on the cap 1920 is a slit septum 2040, which is thus disposed at the first end 2006 of the housing passage 2004. With reference to FIG. 45, it will be recognized that the inner and outer surfaces 2042, 2044 of the slit septum 2040 are concave prior to assembly. In particular, the inner surface 2042 and the outer surface 2044 have different radii of curvature, as illustrated. As is also illustrated, the radius of curvature, or simply "the curvature," of the outer surface 2044 is greater than the curvature of the inner surface 2042. It will be recognized that this is simply an embodiment according to the present disclosure, and that other septum shapes may be used as well, such as an embodiment wherein the inner and outer surfaces 2042, 2044 have similar radii of curvature, or where the differences in curvature are greater than are illustrated. The slit septum 2040 shaped as illustrated may be referred to as an inwardly-concave overmolded slit septum. An inwardly-concave overmolded slit septum has certain advantages relative to conventional slit septums.

Certain conventional slit septums rely on a compression seal between a rigid housing (which may be made of metal, glass or plastic, for example) and the septum. In particular, a separate, individually-fabricated, oversized septum is disposed into an entrance of the housing, the outer diameter of the septum being greater than the inner diameter of the entrance of the housing. The septum may be attached to the housing mechanically (crimping, swaging, or threading, for example) or through the use of an adhesive, which attachment mechanisms may contribute to the compression seal. However, mechanical attachment is a challenge because of the dimensional constraints defined in ISO 594, and adhesive attachment creates manufacturing reliability challenges, especially for steam-sterilized applications.

Conventional overmolded septums remove the requirement for mechanical or adhesive attachment, but present other challenges. In particular, while it is desired for the overmolded part to have a flat surface, because a flat surface is believed to aid in the disinfection of the surface prior to use, the tension in the material because of post-mold shrinkage may result in slit opening, or separation, and subsequent leakage at low pressures. That is, when the septum is slit during the manufacturing process, the residual tensions in a flat overmolded septum cause the slit to open, creating leak channels. While flexing of the separation at relatively high pressures may force the slit closed, leaks may form at low pressures. Furthermore, the separation at the slit may extend into the septum, or through the septum in certain circumstances, and may provide a place for microbes to collect and grow, despite diligent efforts to clean and disinfect the septum surface.

It has been found that the inwardly-concave slit septum 2040 permits use of overmolding, thus eliminating the need for mechanical or adhesive attachment, while limiting the tension created when a flat overmolded septum is used. In particular, the inwardly-concave septum reduces the slit opening effect from post-mold shrinkage by allowing shrinkage of septum material in the axis of the septum rather than only perpendicular to the axis. The result is a septum with less stored strain energy, resulting in a lesser degree of separation when the septum is slit.

However, further improvements may be possible when the inwardly-concave overmolded slit septum is supported and/or displaced axially from within by having a concave surface. Thus, as illustrated, a resilient member 2050 (in the form of a compression spring) biases a first end 2052 of the slider 2010 into engagement with the slit septum 2040. While appearing planar in FIGS. 44 and 45, the first end 2052 of the slider 2010 is concave, similar to the septum 2040 and particularly the inner surface 2042. The curvature of the first end 2052 may be substantially similar to the curvature of the inner surface 2042 so that the curvatures are mating. The engagement between the first end 2052 and the inner surface 2042 causes the flattening of the outer surface 2044 from its initial shape (of FIG. 45), which flattening has been shown to an exaggerated degree in FIG. 44. The distance of travel of the inner surface 2042 between the state illustrated in FIG. 45 and that illustrated in FIG. 44 may be referred to as the assembly flexing distance.

The flattening of the outer surface 2044 need not result in a planar surface. Some degree of curvature may remain. The flattening of the outer surface 2044 of the septum 2040 improves the ability of the septum 2040 to be cleaned prior to use by swabbing or disinfecting according to conventional techniques.

The cooperation of the slider 2010 and the septum 2040 may have other effects, other than simply causing the flattening the outer surface 2044. The flattening of the septum 2040 also may concentrate forces on the slit, assisting in establishing a compression seal on the slit. It will be recognized, that excessive force applied to the septum 2040 may actually result in spreading the septum, causing a separation to form along the slit, so there is a balance of forces and displacements involved. However, the cooperation of the slider 2010 and the septum 2040 may result in a seal that is resistant to high or low pressure from fluid within in the container.

As will be recognized, the other features of the slider 2010 are held in common with certain of the embodiments discussed above. For example, the slider 2010 has a second end 2060 and a side 2062 to which a moveable seal 2064 is attached, by overmolding, for example. The moveable seal 2064 moves relative to an inner surface 2066 of the body 2022 of the housing 2002, and cooperates with the housing 2002 and the slider 2010 to define an expandable chamber which provides positive displacement upon male Luer withdrawal.

Figure 46:
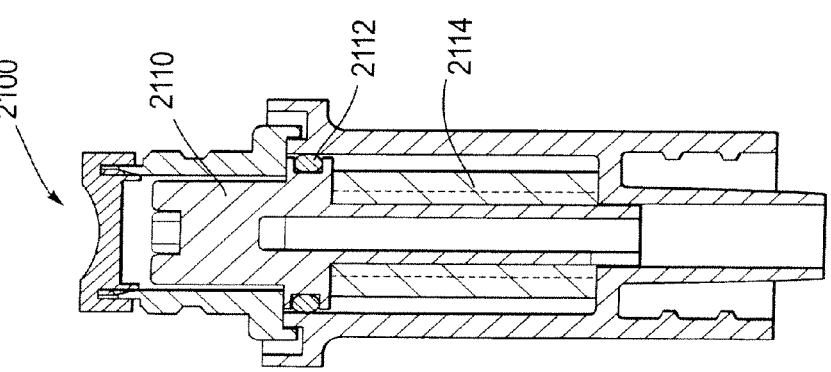
FIG. 46 is a cross-sectional view of a straight in-line connector with a slit septum and compression spring in a first state.

A variant of this connector is illustrated in FIG. 46. Of particular note, the connector 2100 replaces an o-ring 2102 for the overmolded moveable seal 2064 of the previous embodiment. Furthermore, the connector 2100 includes a slider 2110 that has a tubular extension 2112 that is received within the resilient member 2114, which tubular extension may assist in centering the slider on the resilient member 2114 and ensuring that the fluid path through the connector 2100 remains open during operation of the connector 2100.

Figure 47:
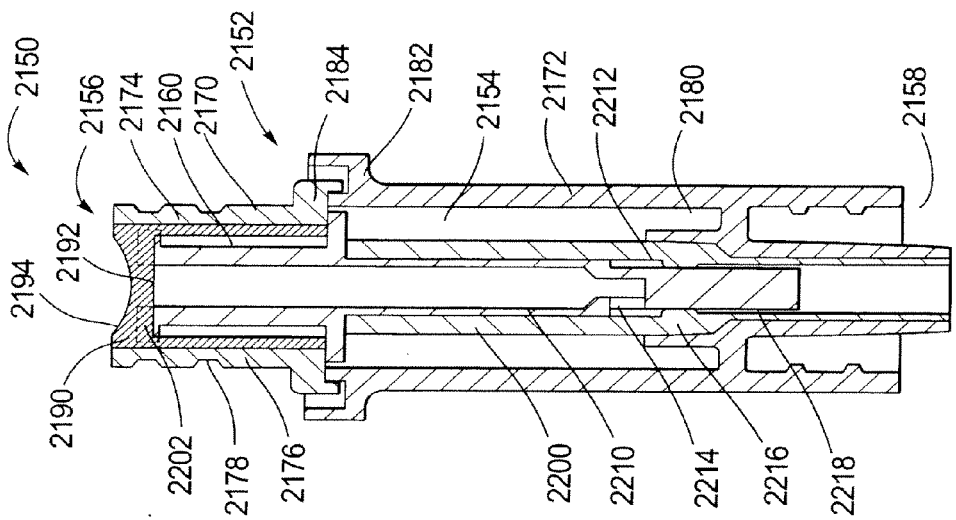
FIG. 47 is a cross-sectional view of a straight in-line connector with a slit septum and compression spring in a first state.
Figure 48:
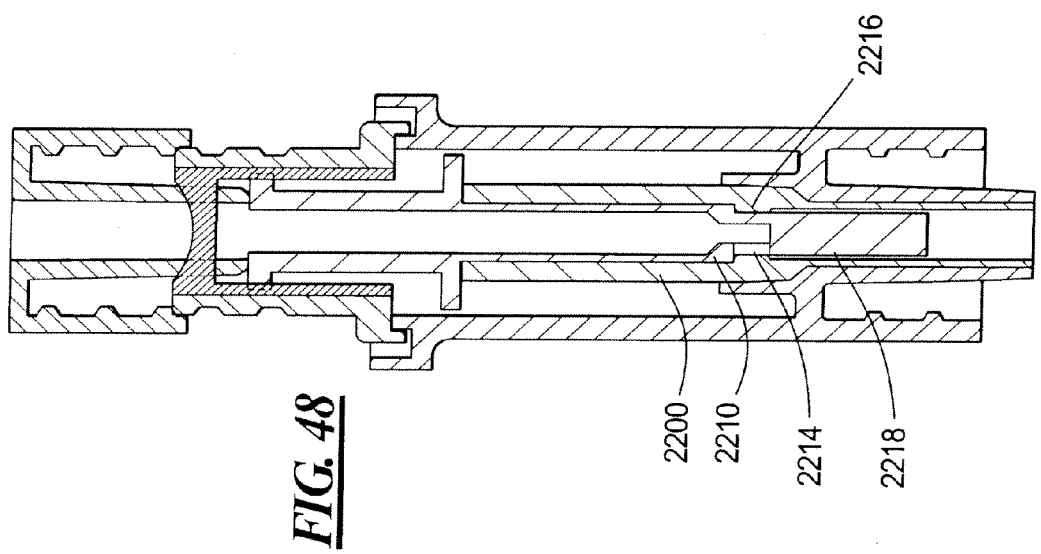
FIG. 48 is a cross-sectional view of the connector of FIG. 47 in a second state.
Figure 49:
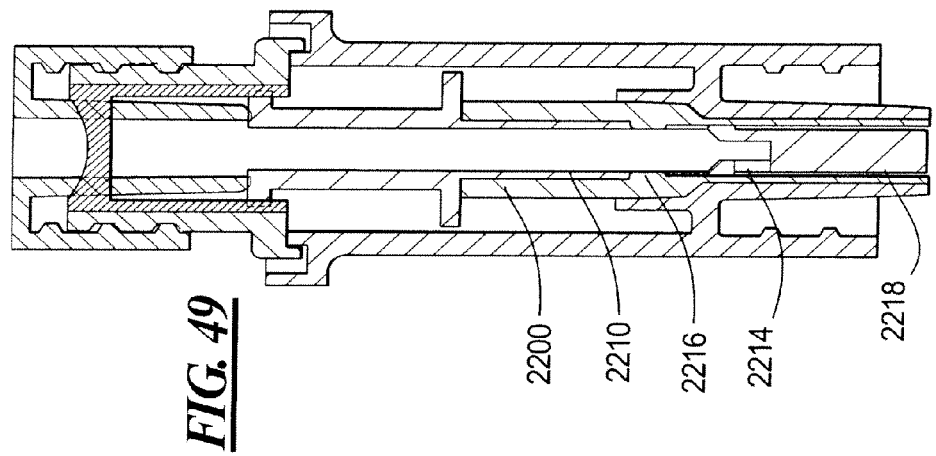
FIG. 49 is a cross-sectional view of the connector of FIG. 47 in a third state.

FIGS. 47-49 illustrate a still further variant of a connector 2150. The connector 2150 includes a housing 2152 having a housing passage 2154 with first and second open ends 2156, 2158. A slider 2160 is disposed in the passage 2154 and moveable between the first and second ends 2156, 2158 of the housing passage 2154.

As will be noted, the housing 2152 is formed of at least two pieces: the cap 2170 and the body 2172. The cap 2170 includes a first passage 2174 that defines a distal section of the passage 2154. The first passage 2174 is defined in a tubular extension 2176 of the cap 2170 that has threads 2178 formed therein, permitting use of the extension 2176 as a female Luer. The generally cylindrical body 2172 includes a passage 2180 that defines a proximal section of the passage 2154. A distal end 2182 of the body 2172 is joined to a proximal end 2184 of the cap 2170 through the use of ultrasonic welding, for example, to attach the two sections 2170, 2172 of the housing 2152 together.

Overmolded on the cap 2170 is a inwardly-concave overmolded slit septum 2190. As was the case with the embodiment of FIGS. 44-45, the inner and outer surfaces 2192, 2194 of the slit septum 2190 are concave prior to assembly, and may have different radii of curvature. The inwardly-concave overmolded slit septum 2190 is supported from within by the slider 2160 having a concave surface. In particular, a resilient member 2200 (in the form of a compression spring overmolded with the body 2172) biases a first end 2202 of the slider 2160 into engagement with the slit septum 2190.

While appearing planar in FIGS. 47-49, the first end 2202 of the slider 2160 is concave, similar to the septum 2190 and particularly the inner surface 2192. The curvature of the first end 2202 may be substantially similar to the curvature of the inner surface 2192 so that the curvatures are mating. The engagement between the first end 2202 and the inner surface 2192 causes the flattening of the inner and outer surfaces 2192, 2194 from their initial shape, which flattening has been shown to an exaggerated degree in regard to the inner surface in the drawings.

The slider 2160 includes a tubular extension 2210 extension that depends into a passage 2212 through the resilient member 2200. The tubular extension 2210 has an aperture 2214 that is selectively sealed and unsealed by the cooperation of the extension with an inwardly-directed seal 2216 attached to (as illustrated, formed integrally with) the resilient member 2200. In the state, illustrated in FIG. 46, the seal 2216 abuts an outer surface 2218 of the extension 2210, thus limiting passage of fluids through the aperture 2214 by placing a barrier between the aperture 2214 and the second end 2158 of the housing 2152. In the state illustrated in FIG. 49, the slider 2160 has been advanced so that the aperture 2214 is advanced past the seal 2216, thereby permitting fluid to flow through the aperture. FIG. 48 illustrates an embodiment between the state illustrated in FIG. 47 and the state illustrated in FIG. 49, where the aperture 2214 is just passing by the seal 2216.

Figure 50:
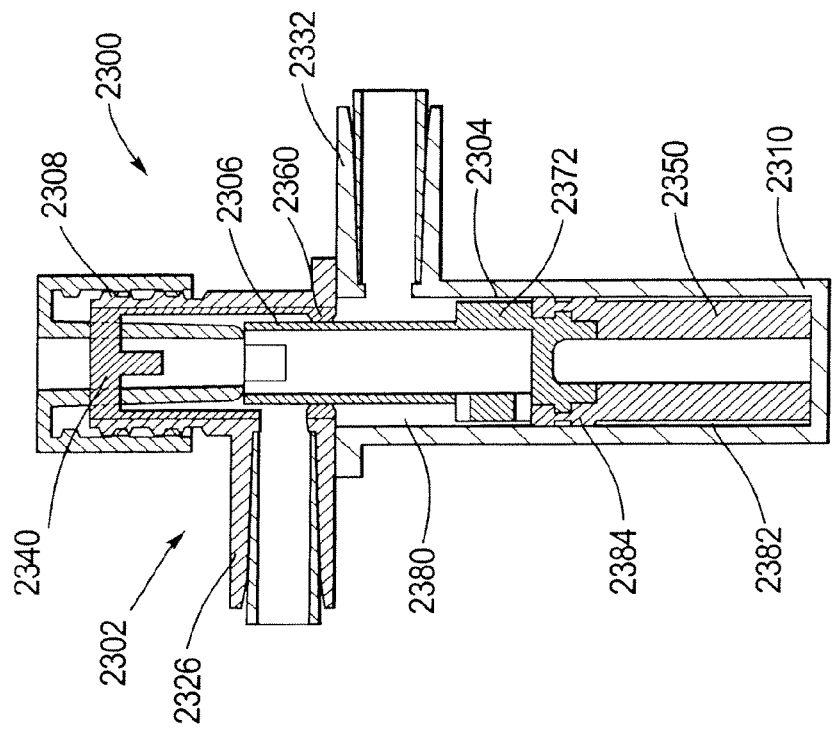
FIG. 50 is a cross-sectional view of a T-site connector with a slit septum and a compression spring in a first state.
Figure 51:
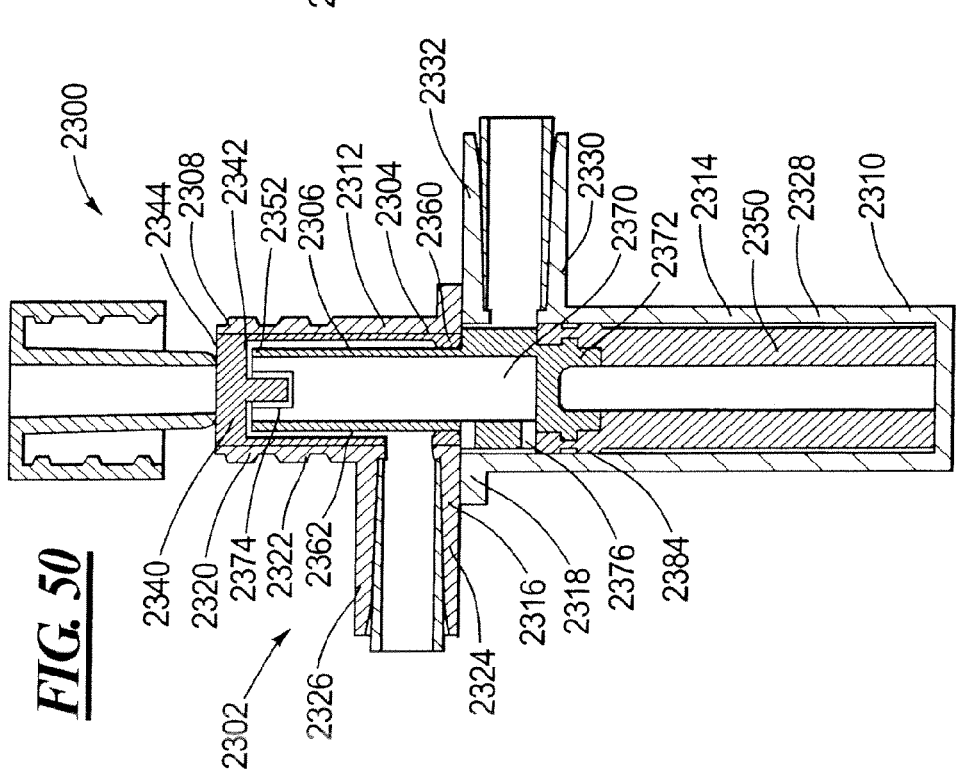
FIG. 51 is a cross-sectional view of the connector of FIG. 50 in a second state.

FIGS. 50-51 illustrate a yet another variant of a connector 2300. Similar to the connectors described in FIGS. 44-49, the connector utilizes a slit septum through which the Luer (or other instrument) is inserted before coming in contact with the slider. However, unlike the embodiments of FIGS. 44-49, the connector 2300 does not have first and second open ends, the fluid passing through the connector between the first and second ends. Instead, the connector 2300 has side ports in communication with an open end via a housing passage, thereby defining a "T" connector.

Turning first to FIG. 50, the connector 2300 includes a housing 2302 with a first housing passage 2304. A slider 2306 is disposed in the passage 2304 and moveable between a first open end 2308 and a second closed end 2310. It will be recognized that the second end 2310 may be vented according to other embodiments.

As will be noted, the housing 2302 is formed of at least two sections: a cap 2312 and a base 2314. A proximal end 2316 of the cap 2312 may be joined to a distal end 2318 of the base 2314 through the use of ultrasonic welding, for example, to attach the cap 2312 and the base 2314 of the housing 2302 together.

The cap 2312 defines a distal section of the passage 2304. The cap 2312 has a first tubular extension 2320 with threads 2322 formed therein, permitting use of the extension 2320 as a female Luer. The cap 2312 also has a second tubular extension 2324 that depends a right angles relative to the extension 2320 as shown, although this angle need not be a right angle according to all embodiments according to this disclosure. The extension 2324 defines a first side port 2326 to which a line may be connected.

The base 2314 defines a proximal section of the passage 2304. The base 2314 also includes a first tubular extension 2328 and a second tubular extension 2330. The first and second tubular extensions 2328, 2320, like the first and second tubular extensions 2320, 2324, are disposed at right angles relative to each other as illustrated, although other embodiments may have the extensions 2328, 2330 disposed at other angles relative to each other. The second extension 2330 defines a second side port 2332 to which a line may be connected; as illustrated, the second side port 2332 is not aligned with the first side port 2326.

Overmolded on the cap 2312 is a inwardly-concave slit septum 2340. As was the case with the embodiments above, the inner and outer surfaces 2342, 2344 of the slit septum 2340 are concave prior to assembly, and may have different radii of curvature. The inwardly-concave overmolded slit septum 2340 is supported from within by the slider 2306 having a concave surface. In particular, a resilient member 2350 (in the form of a compression spring) disposed in the closed end 2310 biases a first end 2352 of the slider 2306 into engagement with the slit septum 2340. When the first end 2352 of the slider 2306 abuts the slit septum 2340, a fluid-tight seal is formed across the septum 2340 to limit or prevent fluid from exiting the connector 2300 and to limit or prevent fluid or contaminants from entering the connector 2300.

In addition to the slit septum 2340, an inwardly-directed wiper (or stationary seal) 2360 may be overmolded onto the cap 2312. The wiper 2360 abuts an outer surface 2362 of the slider 2306. The wiper 2360 and the outer surface 2362 of the slider 2306 form a fluid-tight seal to prevent fluid from passing across the seal.

It will also be recognized that the slider 2306 has a passage 2370 that extends from the first end 2352 of the slider 2306 to the second end 2372. The passage 2370 may be generally aligned with a longitudinal axis of the passage 2304, and the passage 2370 may be centered relative to the slider 2306. Connected to the passage 2370 are one or more side passages 2374, 2376. The side passages 2376 are disposed at the first end 2352 of the slider 2306, while the side passages 2376 are disposed at the second end 2372 of the passage 2370. As illustrated, the side passages 2374, 2376 may be disposed at right angles to the passage 2370, although this need not be the case according to all embodiments. Further, the side passages 2376 may be disposed in the opposite direction relative to the side port 2332 to reduce or minimize the non-flushable spaces, although this need not be the case according to all embodiments.

In the state illustrated in FIG. 50, the slit septum 2340 limits or prevents fluid from entering the passage 2304. However, fluid may flow between the side port 2326 to the side port 2332. In particular, the fluid may enter the side port 2326, pass around the slider 2306 in an annular space between the slider 2306 and the housing 2302, pass through the side holes or passages 2374 into the central passage 2370, pass from the central passage 2370 into the side passages 2376, pass through an annular space between the slider 2306 and the housing 2302, and out of the side port 2332. It is also possible for fluid to follow the reverse path between the ports 2326, 2332. In either event, the arrangement of passages permit the connector 2300 to be self-priming. Embodiments of septum 2340 may include being formed with downwardly depending lips as shown or with a generally flat bottom surface. Considerations for such a design will include pressure retention requirements.

In operation, a Luer is inserted into the slit septum 2340 as illustrated in 51, forcing the slider 2306 against the resilient member 2350 in the direction of the second end 2310 of the passage 2304. Fluid flow may now occur between the side ports 2326, 2332 and between the Luer and either of the side ports 2326, 2332. That is, in the variant illustrated, there is no shut-off between the side ports 2326, 2332. Furthermore, as the slider 2306 advances along the passage 2304, fluid fills an expandable space (or chamber) 2380 between the wiper 2360 and the second end 2372 of the slider 2306. The passage of fluid into a space 2382 in which the resilient member 2350 is disposed is limited or prevented by a further moveable seal 2384 formed with the resilient member 2350 that abuts an inner surface of the housing 2302 that defines the passage 2304.

When the Luer is removed from the connector 2300, fluid in the space 2380 is forced out of the space 2380 by the movement of the slider 2306. The seal formed between the wiper 2360 and the slider 2306 limits or prevents the fluid from passing along the passage 2304 in one direction, while the seal formed by the wiper 2384 and the housing 2302 limits or prevents fluid from passing along the passage 2304 in the other direction. Depending upon the relative pressures, the fluid from the space 2380 will exit the connector 2300 through either the side passage 2326 or the side passage 2332. As a consequence, the connector 2300 is self-flushing, as well as self priming.

It will be recognized that the connector 2300 illustrated in FIGS. 50 and 51 is but one possible T-connector according to the present disclosure. Further variants are possible, wherein the housing and/or slider are reconfigured to permit shut-off, or to eliminate self-priming and/or self-flushing. In certain embodiments, one of the side ports may be removed, leaving the open end and a single side port. Elements that have been described as overmolded may be formed separately and then joined together. The slit septum may be replaced by one of the other variants described above wherein the first end 2352 depends through the first end 2308 of the passage 2304 instead. Moreover the slider 2306 may be formed with a solid top so that the passages 2374 are formed as holes or may have a open top.

As an illustration of the numerous combinations possible, a connector 2400 is illustrated in FIGS. 52 and 53. Specifically, the variant connector 2400 illustrates how various aspects of the other embodiments may be incorporated within the context of a T-site connector, such as is illustrated in FIGS. 50 and 51.

Turning first to FIG. 52, the connector 2400 includes a housing 2402 with a first housing passage 2404. A slider 2406 is disposed in the passage 2404 and moveable between a first open end 2408 and a second closed end 2410, although unlike most of the sliders illustrated above, the slider 2406 lacks any passages therethrough. Further, the housing 2402 may include at least two sections: a cap 2412 and a base 2414. In this regard, the connector 2400 is similar to the connector 2300.

However, the cap 2412 defines not only the distal section of the passage 2404, but the side ports 2420, 2422 as well. Further, while the base 2414 defines the proximal section of the passage 2404, a tension spring 2424 (rather than a compression spring) is overmolded with the cap and receives the slider 2406 therein. As such, while the base 2414 may limit the movement of the slider 2406 in the direction of the end 2410, the tension spring 2424 preferably prevents fluid from entering the proximal section of the passage 2404.

Unlike the connector 2300, the connector 2400 does not include a slit septum. Instead the connector 2400 has a seal 2430 that is overmolded on the cap 2412 at the open end 2408 of the passage 2404. A side surface 2432 of the slider 2406 abuts the seal 2430, which may have a plurality of flanges, similar to the connectors of FIGS. 39-43. The slider 2406 has an angled end 2434 that depends from the open end 2408 of the passage 2404 that is contacted by a Luer to move the slider 2406 from a first state illustrated in FIG. 52 and a second state illustrated in FIG. 53.

In operation, the connector 2400 has no shut-off; fluid may pass around the slider 2406 between the side ports 2420, 2422 in the first state illustrated in FIG. 52 and between the open end 2408 and the side ports 2420, 2422 in the second state illustrated in FIG. 53. Because fluid is capable of moving between the side ports 2420, 2422 in the first state illustrated in FIG. 52, the connector 2400 is also self-priming. Moreover, it will be recognized that if one of the side ports 2420, 2422 was removed, the resulting structure could be used as a right-angle connector instead.

As a more general proposition, it will be recognized that the variants discussed above are exemplary in the context of the embodiments in which they are presented, and further combinations of the aspects of the illustrated embodiments are possible. For example, relative to the tension spring variants, the tension spring may be used in substitution for the vacuum chamber biasing or the compression spring present in other embodiments. Thus it will be recognized that the presence of a variant in the context of one embodiment should not be read as preventing its use with the features present in another embodiment, or limiting its use with only those features presented in that embodiment. Consequently, it is expressly disclosed herein that the variants may be used in such combinations as are illustrated, and also in combinations that are not illustrated but where the operation of the variants would not prevent there use in combination.

Further, use of the above-mentioned needleless connector, according to any of the various embodiments described herein, may provide one or more of the following advantages relative to conventional needleless connectors, even those that include a slider.

Those embodiments providing an automatic flush have certain advantages to known LADs that require a flush (or SASH or SAS therapy) before and after access to the med/sample port. By providing the automatic flush before and/or after medication infusion or injection, the number of accesses to the med/sample port is reduced, with an attendant reduction in the risk of infection. The automatic flush also eliminates the time requirement if a manual flush had been used instead. Still further, where the automatic flush is used in place of SASH, or even SAS, therapy, the savings in time and material may be even greater.

Further, by providing a connector with an integral pumping action activated by Luer insertion/removal, the need to rely on or to provide a supplemental fluid propulsion mechanism, such as gravity or an elastomeric reservoir for IV infusion, may be eliminated so as to provide greater flexibility for the patient and clinician. Additionally, in those configurations intended for blood sampling, the connector may have the additional advantages of reducing the number of steps required for discard reinfusion, as well as of reducing the number of accesses required.

Still further advantages may be obtained by impregnating the slider, the septum or the housing with an antimicrobial material or composition, or by coating the slider, the septum or the housing with such a material. For example, the antimicrobial material may include chemical disinfectants, for example, alcohols, such as isopropanol and ethanol. Biguanides may also be used, including chlorhexidine and its salts (e.g. chlorhexidine acetate, chlorhexidine gluconate, chlorhexidine hydrochloride and chlorhexidine sulfate). Further examples include, bisphenols, including triclosan, and halogen-releasing agents, including chlorine and iodine compounds. Silver and its salts (e.g. silver acetate, silver iodide, silver nitrate, silver sulfadiazine) may be included, as may copper and its salts. As a further alternative, quaternary ammonium compounds, including benzalkonium chloride, may be used. Still further exemplary alternatives include antimicrobial dyes, including acridines and crystal violet, boric acid, salicylic acid and N-halamines.

What is claimed is:

1. A needleless connector comprising:
a housing having a housing passage with an open end;
an inwardly-concave overmolded slit septum disposed at the open end of the housing passage;
a slider disposed in the housing passage and having a first and second opposing ends and a slider passage that extends from the first end to the second end of the slider; and
a resilient member disposed in the housing and biasing the slider toward the open end of the housing passage,
the inwardly-concave slit septum having an inner surface with a curvature, and the first end of the slider is concave and has a curvature that is similar to the curvature of the slit septum.

2. The needleless connector according to claim 1, wherein the slider comprises a moveable seal, the seal abutting an inner surface of the housing that defines the housing passage, the housing, the slider and the moveable seal defining an expandable chamber.

3. The needleless connector according to claim 2, wherein the moveable seal is overmolded to the slider.

4. The needleless connector according to claim 1, wherein:
the resilient member has a passage therethrough and the slider has a tubular extension that depends into the passage through the resilient member, and
the tubular extension has at least one aperture that the resilient member seals in a first state, and that is unsealed in a second state.

5. The needleless connector according to claim 4, wherein the resilient member comprises an inwardly-directed seal disposed along the passage in the resilient member, the inwardly-directed seal abutting an outer surface of the extension in the first state to limit the passage of fluids through the aperture.

6. The needleless connector according to claim 1, wherein the housing has at least one side port in communication with the housing passage.

7. The needleless connector according to claim 6, wherein the housing has two side ports in communication with the housing passage, the side ports being non-aligned.

8. The needleless connector according to claim 6, wherein the housing passage has a closed end opposite the open end, the resilient member being disposed in the closed end and having a moveable seal formed therewith that abuts an inner surface of the housing that defines the housing passage.

9. The needleless connector according to claim 8, comprising a stationary seal disposed in the housing passage between the open end and the moveable seal, the housing, the slider, the stationary seal and the moveable seal defining an expandable space.

10. The needleless connector according to claim 6, the slider comprising one or more side passages in communication with the slider passage, the side passages being disposed opposite the at least one side port.

11. The needleless connector according to claim 1, wherein the resilient member biases the slider to that the first end of the slider abuts an inner surface of the slit septum.

12. The needleless connector according to claim 11, wherein the resilient member comprises a compression spring.

13. A needleless connector comprising:
a housing having a housing passage with an open end;
a slit septum disposed at the open end of the housing passage;
a slider disposed in the housing passage and having a first and second opposing ends and a slider passage that extends from the first end to the second end of the slider; and
a resilient member disposed in the housing and biasing the slider toward the open end of the housing passage
wherein the slider comprises a side between the first and second ends, the slider passage having first and second open ends with the first end of the slider passage disposed along the side of the slider and the second end of the slider passage disposed at the second end of the slider.

* * * * *